(12) United States Patent
Beswick et al.

(10) Patent No.: US 9,115,132 B2
(45) Date of Patent: Aug. 25, 2015

(54) TETRAZOLE COMPOUNDS AS CALCIUM CHANNEL BLOCKERS

(75) Inventors: Paul Beswick, Cambridge (GB); Robert James Gleave, Cambridge (GB); Shuji Hachisu, Cambridge (GB); Sadie Vile, Cambridge (GB); Nicholas Bertheleme, Cambridge (GB); Simon E. Ward, Cambridge (GB)

(73) Assignee: Convergence Pharmaceuticals Limited, London (GB)

( * ) Notice: Subject to any disclaimer, the term of this patent is extended or adjusted under 35 U.S.C. 154(b) by 151 days.

(21) Appl. No.: 13/808,243

(22) PCT Filed: Jul. 8, 2011

(86) PCT No.: PCT/GB2011/051276
§ 371 (c)(1),
(2), (4) Date: Apr. 30, 2013

(87) PCT Pub. No.: WO2012/004604
PCT Pub. Date: Jan. 12, 2012

(65) Prior Publication Data
US 2013/0210796 A1    Aug. 15, 2013

Related U.S. Application Data

(60) Provisional application No. 61/362,712, filed on Jul. 9, 2010.

(51) Int. Cl.
| | | |
|---|---|---|
| A61K 31/41 | (2006.01) |
| C07D 401/14 | (2006.01) |
| C07D 403/06 | (2006.01) |
| C07D 413/06 | (2006.01) |
| C07D 417/06 | (2006.01) |
| C07D 471/04 | (2006.01) |
| C07D 471/10 | (2006.01) |
| C07D 487/04 | (2006.01) |
| C07D 487/08 | (2006.01) |
| C07D 491/08 | (2006.01) |
| C07D 513/04 | (2006.01) |
| C07D 257/04 | (2006.01) |
| C07D 257/06 | (2006.01) |

(52) U.S. Cl.
CPC .............. *C07D 471/10* (2013.01); *A61K 31/41* (2013.01); *C07D 257/04* (2013.01); *C07D 257/06* (2013.01); *C07D 401/14* (2013.01); *C07D 403/06* (2013.01); *C07D 413/06* (2013.01); *C07D 417/06* (2013.01); *C07D 471/04* (2013.01); *C07D 487/04* (2013.01); *C07D 487/08* (2013.01); *C07D 491/08* (2013.01); *C07D 513/04* (2013.01)

(58) Field of Classification Search
CPC .. C07D 401/14; C07D 403/06; C07D 413/06; C07D 417/06; C07D 471/04; C07D 471/10; C07D 487/04; C07D 487/08; C07D 491/08; C07D 513/04; C07D 257/04
USPC .......................................... 548/254; 514/382
See application file for complete search history.

(56) References Cited

U.S. PATENT DOCUMENTS

| | | |
|---|---|---|
| 2,470,084 A | 5/1949 | Harvill et al. |
| 5,466,823 A | 11/1995 | Talley et al. |
| 5,474,995 A | 12/1995 | Ducharme et al. |

(Continued)

FOREIGN PATENT DOCUMENTS

| | | |
|---|---|---|
| WO | WO-96/25405 | 8/1996 |
| WO | WO-97/14691 | 4/1997 |

(Continued)

OTHER PUBLICATIONS

Ugi et al. "Isontirles. II. Reaction of isonitriles with carbonyl compounds, amines, and hydrazoic acid", Chemishe Berichte, 1061, vol. 94, pp. 734-742.*

(Continued)

*Primary Examiner* — Kendra D Carter
(74) *Attorney, Agent, or Firm* — Foley & Lardner LLP

(57) ABSTRACT

The present invention relates to novel tetrazole compounds of Formula (I) wherein A is (II) or (III); to processes for their preparation; to pharmaceutical compositions containing the compounds; and to the use of the compounds in therapy to treat diseases for which blocking the Ca$_v$2.2 calcium channels is beneficial.

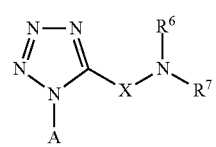

wherein A is

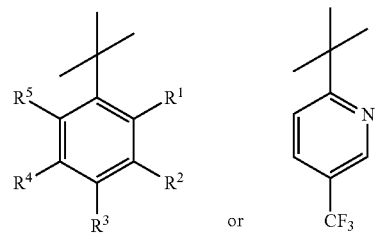

19 Claims, No Drawings

(56) References Cited

U.S. PATENT DOCUMENTS

| | | | |
|---|---|---|---|
| 5,633,272 | A | 5/1997 | Talley et al. |
| 6,291,523 | B1 | 9/2001 | Fujimoto et al. |
| 6,310,099 | B1 | 10/2001 | Fujimoto et al. |
| 2009/0163545 | A1 | 6/2009 | Goldfarb |

FOREIGN PATENT DOCUMENTS

| | | |
|---|---|---|
| WO | WO-97/38986 | 10/1997 |
| WO | WO-98/03484 | 1/1998 |
| WO | WO-99/12930 | 3/1999 |
| WO | WO-00/26216 | 5/2000 |
| WO | WO-00/38311 | 6/2000 |
| WO | WO-00/52008 | 9/2000 |
| WO | WO-01/58881 A1 | 8/2001 |
| WO | WO-02/18374 A1 | 3/2002 |
| WO | WO-2004/105750 A1 | 12/2004 |
| WO | WO-2006/086229 A1 | 8/2006 |
| WO | WO-2007/118323 A1 | 10/2007 |

OTHER PUBLICATIONS

Gross et al., "Tetrazole derivatives. IV. Some pharmacologic properties of aminomethyltetrazoles", Journal of Pharmacology and Experimental Therapeutics (1948), 92, 323-329.*

Berge, et al., "Pharmaceutical Salts," J. Pharma. Sci., (1977), 66(1):1-19.

Bowersox et al., "Selective N-Type Neuronal Voltage-Sensitive Calcioum Channel Blocker, SNX-111, Produces Spinal Antinociception in Rat Models of Acute, Persistent and Neuropathic Pain," Journal of Pharmacology and Experimental Therapeutics, (1996), 279(3):1243-1249.

Brose, et al., "Use of Intrathecal SNX-111, a Novel, N-Type, Voltage-Sensitive, Calcium Channel Blocker, in the Management of Intractable Brachial Plexus Avulsion Pain," The Clinical Journal of Pain, (1997), 13:256-259.

Kim et al., "Altered Nociceptive Response in Mice Deficient in the à$_{1B}$ Subunit of the Voltage-Dependent Calcium Channel," Mol. Cell. Neurosci., (2001),18(2):235-245.

Saegusa et al., "Suppression of inflammatory and neuropathic pain symptoms in mice lacking the N-type $Ca^{2+}$ channel," EMBO J., (2001), 20(10):2349-2356.

Scott et al., "Actions of intrathecal omega-conotoxins CVID, GVIA, MVIIA, and morphine in acute and neuropathic pain in the rat," Eur. J. Pharmacol., (2002), 451(3):279-286 (Abstract Only).

Smith et al. "The novel N-type calcium channel blocker, AM336, produces potent dose-dependent antinociception after intrathecal dosing in rates and inhibits substance P release in rate spinal cord slices," Pain, (2002), 96:119-127.

Winquist et al., "Use-dependent blockade of $Ca_v v2.2$ voltage-gated calcium channels for neuropathic pain," Biochemical Pharmacology, (2005), 70:489-499.

\* cited by examiner

TETRAZOLE COMPOUNDS AS CALCIUM CHANNEL BLOCKERS

CROSS-REFERENCE TO RELATED APPLICATIONS

This application is the U.S. national stage application of International Patent Application No. PCT/GB2011/051276, filed on Jul. 8, 2011, which claims priority to U.S. Provisional Application No. 61/362,712, filed on Jul. 9, 2010, each of which is incorporated herein by reference in its entirety.

TECHNICAL FIELD

The present invention relates to novel tetrazole compounds; to processes for their preparation; to pharmaceutical compositions containing the compounds; and to the use of the compounds in therapy to treat diseases for which blocking the $Ca_v2.2$ calcium channels is beneficial, i.e. in particular to treat pain.

BACKGROUND

Pre-synaptic $Ca_v2.2$ (N-type) voltage-gated calcium channels in the dorsal horn of the spinal cord modulate the release of key pro-nociceptive neurotransmitters such as glutamate, substance P (SP) and calcitonin-gene-related peptide (CGRP), indicating the potential therapeutic use of $Ca_v2.2$ calcium channel blockers as analgesics.

Peptidic ω-conotoxins, isolated from the venom of cone snails, have been shown to be selective for $Ca_v2.2$ calcium channels and can block SP release in the spinal cord (Smith et al. (2002) Pain, 96: 119-127). Moreover, they have been shown to be antinociceptive in animal models of chronic pain following intrathecal administration (Bowersox et al. (1996) Journal of Pharmacology and Experimental Therapeutics, 279: 1243-1249; Smith of al. (2002) supra), and have been shown to be effective analgesics in clinical use, particularly in the treatment of neuropathic pain (Brose et al. (1997) Clinical Journal of Pain, 13: 256-259).

Winquist et al. has shown that $Ca_v2.2$ channels may offer the potential to reduce neuronal signalling, thereby treating disorders such as pain. However, side effect issues may impact the success of such an approach (Winquist et al. (2005) Biochemical Pharmacology, 70: 489-499). A number of journal articles have been published on the effect of natural inhibitors of $Ca_v2.2$ channels (see Bowersox et al. (1996) Journal of Pharmacology and Experimental Therapeutics 279 (3):1243-1249; Scott et al. (2002) European Journal of Pharmacology 451(3):279-286). In addition, several journal articles have been published on the phenotypic characterisation of transgenic mice lacking the $Ca_v2.2$ gene (see Saegusa et al. (2001) EMBO J. 20(10):2349-2356; Kim et al. (2001) Mol. Cell Neurosci. 18(2):235-245.). These articles support the stance that tonic inhibition of $Ca_v2.2$ may result in cardiovascular (hypotension) and CNS (sedation) side effects at therapeutic concentrations.

Due to these drawbacks of tonic $Ca_v2.2$ inhibitors, it is the object of the invention to provide an alternative class of $Ca_v2.2$ antagonist: a state- or use-dependent Cav2.2 blocker, which has the potential to selectively inhibit highly active channels contributing to the pathophysiology of chronic pain whilst sparing the contributions of Cav2.2 to wider physiological levels of activity within the peripheral and central nervous system. Therefore, the object of the invention is to identify novel compounds for use in therapy that preferentially block $Ca_v2.2$ calcium channels under conditions of increased neuronal excitability, so-called use-dependent blockers, as is the case in chronic pain syndromes.

WO2006/086229 (Abbott Laboratories) relates to tetrazole derivatives for the treatment of neuropathic pain, chronic inflammatory pain, inflammation, neurodegeneration and of promoting neuroregeneration. US2009/0163545 (University of Rochester) describes tetrazole derivatives and relates to methods for altering the lifespan of eukaryotic organisms.

SUMMARY OF THE INVENTION

In a first aspect, there is provided a compound of formula (I), or a salt thereof:

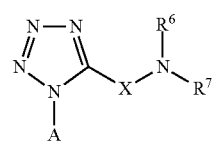

(I)

wherein
A is

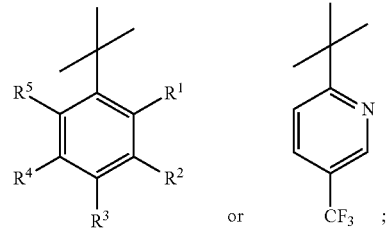

$R^1$ is hydrogen, methyl or chloro;
$R^2$ is hydrogen, trifluoromethyl, trifluoromethoxy, chloro or cyano;
$R^3$ is hydrogen, cyano, trifluoromethyl, trifluoromethoxy, difluoromethoxy, chloro, bromo, —S—$CH_3$, —$SO_2$—$C_{1-3}$alkyl or —$SF_5$;
$R^4$ is hydrogen, trifluoromethyl, trifluoromethoxy, chloro or cyano;
$R^5$ is hydrogen, methyl or chloro;
wherein at least one of $R^1$, $R^2$, $R^3$, $R^4$ or $R^5$ is a group other than hydrogen;
X is —$CH_2$—, —$CH_2$—$CH_2$— or —$CH(CH_3)$—;
wherein when $R^1$ is methyl, $R^5$ is hydrogen or chloro, and when $R^5$ is methyl, $R^1$ is hydrogen or chloro;
wherein when $R^2$ is chloro, $R^4$ is hydrogen, trifluoromethyl, trifluoromethoxy or cyano, and when $R^4$ is chloro, $R^2$ is hydrogen, trifluoromethyl, trifluoromethoxy or cyano;
$R^6$ is hydrogen and $R^7$ is $C_{1-5}$ alkyl or $C_{3-6}$cycloalkyl; or $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —$SO_2$—$C_{1-3}$alkyl, $C_{1-3}$haloalkyl and —CO—$C_{1-3}$alkyl;

with the proviso that the compound is not 4-{[1-(4-chlorophenyl)-1H-tetrazol-5-yl]methyl}morpholine, 4-({1-[3-(trifluoromethyl)phenyl]-1H-tetrazol-5-yl}methyl)morpholine hydrochloride, 4-({1-[3-(trifluoromethyl)phenyl]-1H-tetrazol-5-yl}methyl)morpholine, 4-{[1-(3,4-dichlorophenyl)-1H-tetrazol-5-yl]methyl}morpholine, 1-{[1-(4-chlorophenyl)-1H-tetrazol-5-yl]methyl}-4-(methylsulfonyl)piperazine, 1-{[1-(4-chlorophenyl)-1H-tetrazol-5-yl]methyl}-4-(propylsulfonyl)piperazine; 1-{[1-(3,4-dichlorophenyl)-1H-tetrazol-5-yl]methyl}piperidine; 4-{[1-(4-chlorophenyl)-1H-tetrazol-5-yl]methyl}morpholine; 1-{[1-(4-chlorophenyl)-1H-tetrazol-5-yl]methyl}-4-methylpiperidine; 1-{[1-(4-chlorophenyl)-1H-tetrazol-5-yl]methyl}piperidine; 1-{[1-(4-chlorophenyl)-1H-tetrazol-5-yl]methyl}-4-(ethylsulfonyl)piperazine; 1-{[1-(4-chlorophenyl)-1H-tetrazol-5-yl]methyl}-2-methylpiperidine; 1-{[1-(4-chlorophenyl)-1H-tetrazol-5-yl]methyl}piperazine; 1-(4-chlorophenyl)-5-(1-pyrrolidinylmethyl)-1H-tetrazole; 1-{[1-(4-chlorophenyl)-1H-tetrazol-5-yl]methyl}-4-methylpiperazine or 1-{[1-(4-chlorophenyl)-1H-tetrazol-5-yl]methyl}hexahydro-1H-azepine.

In a second aspect, there is provided a compound of formula (I), or a pharmaceutically acceptable salt thereof, for use in therapy, wherein
A is

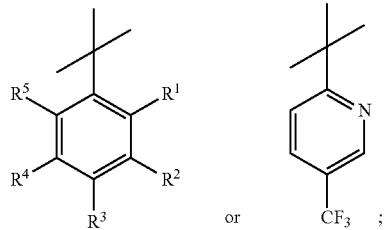

$R^1$ is hydrogen, methyl or chloro;
$R^2$ is hydrogen, trifluoromethyl, trifluoromethoxy, chloro or cyano;
$R^3$ is hydrogen, cyano, trifluoromethyl, trifluoromethoxy, difluoromethoxy, chloro, bromo, —S—CH$_3$, —SO$_2$—C$_{1-3}$alkyl or —SF$_5$;
$R^4$ is hydrogen, trifluoromethyl, trifluoromethoxy, chloro or cyano;
$R^5$ is hydrogen, methyl or chloro;
wherein at least one of $R^1$, $R^2$, $R^3$, $R^4$ or $R^5$ is a group other than hydrogen;
X is —CH$_2$—, —CH$_2$—CH$_2$— or —CH(CH$_3$)—;
wherein when $R^1$ is methyl, $R^5$ is hydrogen or chloro, and when $R^5$ is methyl, $R^1$ is hydrogen or chloro;
wherein when $R^2$ is chloro, $R^4$ is hydrogen, trifluoromethyl, trifluoromethoxy or cyano, and when $R^4$ is chloro, $R^2$ is hydrogen, trifluoromethyl, trifluoromethoxy or cyano;
$R^6$ is hydrogen and $R^7$ is C$_{1-5}$ alkyl or C$_{3-6}$cycloalkyl; or $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, C$_{1-3}$ alkyl, cyano, —SO$_2$—C$_{1-3}$alkyl, C$_{1-3}$haloalkyl and —CO—C$_{1-3}$alkyl.

According to a further aspect, there is provided the use of a compound as defined in the second aspect, or a pharmaceutically acceptable salt thereof, in the manufacture of a medicament for the treatment or prophylaxis of pain.

According to a further aspect, there is provided a method for the treatment or prophylaxis of pain in a human or animal in need thereof comprising administering to said human or animal a therapeutically effective amount of a compound as defined in the second aspect, or a pharmaceutically acceptable salt thereof.

According to a further aspect, there is provided a pharmaceutical composition comprising (a) a compound as defined in the second aspect, or a pharmaceutically acceptable salt thereof, and (b) a pharmaceutically acceptable excipient.

DESCRIPTION OF THE EMBODIMENTS

In a first aspect, there is provided a compound of formula (I), or a salt thereof:

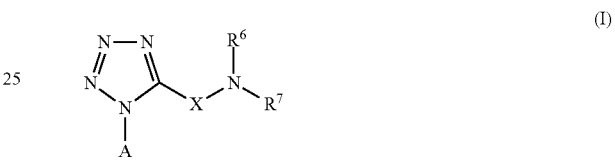

wherein
A is

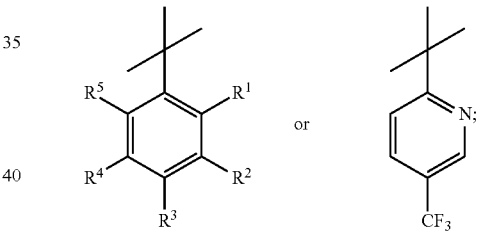

$R^1$ is hydrogen, methyl or chloro;
$R^2$ is hydrogen, trifluoromethyl, trifluoromethoxy, chloro or cyano;
$R^3$ is hydrogen, cyano, trifluoromethyl, trifluoromethoxy, difluoromethoxy, chloro, bromo, —S—CH$_3$, —SO$_2$—C$_{1-3}$alkyl or —SF$_5$;
$R^4$ is hydrogen, trifluoromethyl, trifluoromethoxy, chloro or cyano;
$R^5$ is hydrogen, methyl or chloro;
wherein at least one of $R^1$, $R^2$, $R^3$, $R^4$ or $R^5$ is a group other than hydrogen;
X is —CH$_2$—, —CH$_2$—CH$_2$— or —CH(CH$_3$)—;
wherein when $R^1$ is methyl, $R^5$ is hydrogen or chloro, and when $R^5$ is methyl, $R^1$ is hydrogen or chloro;
wherein when $R^2$ is chloro, $R^4$ is hydrogen, trifluoromethyl, trifluoromethoxy or cyano, and when $R^4$ is chloro, $R^2$ is hydrogen, trifluoromethyl, trifluoromethoxy or cyano;
$R^6$ is hydrogen and $R^7$ is C$_{1-5}$ alkyl or C$_{3-6}$cycloalkyl; or $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system;

c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, $SO_2$—$C_{1-3}$alkyl, $C_{1-3}$haloalkyl and —CO—$C_{1-3}$alkyl;
with the proviso that the compound is not 4-{[1-(4-chlorophenyl)-1H-tetrazol-5-yl]methyl}morpholine, 4-({1-[3-(trifluoromethyl)phenyl]-1H-tetrazol-5-yl}methyl)morpholine hydrochloride, 4-({1-[3-(trifluoromethyl)phenyl]-1H-tetrazol-5-yl}methyl)morpholine, 4-{[1-(3,4-dichlorophenyl)-1H-tetrazol-5-yl]methyl}morpholine, 1-{[1-(4-chlorophenyl)-1H-tetrazol-5-yl]methyl}-4-(methylsulfonyl)piperazine, 1-{[1-(4-chlorophenyl)-1H-tetrazol-5-yl]methyl}-4-(propylsulfonyl)piperazine; 1-{[1-(3,4-dichlorophenyl)-1H-tetrazol-5-yl]methyl}piperidine; 4-{[1-(4-chlorophenyl)-1H-tetrazol-5-yl]methyl}morpholine; 1-{[1-(4-chlorophenyl)-1H-tetrazol-5-yl]methyl}-4-methylpiperidine; 1-{[1-(4-chlorophenyl)-1H-tetrazol-5-yl]methyl}piperidine; 1-{[1-(4-chlorophenyl)-1H-tetrazol-5-yl]methyl}-4-(ethylsulfonyl)piperazine; 1-{[1-(4-chlorophenyl)-1H-tetrazol-5-yl]methyl}-2-methylpiperidine; 1-{[1-(4-chlorophenyl)-1H-tetrazol-5-yl]methyl}piperazine; 1-(4-chlorophenyl)-5-(1-pyrrolidinylmethyl)-1H-tetrazole; 1-{[1-(4-chlorophenyl)-1H-tetrazol-5-yl]methyl}-4-methylpiperazine or 1-{[1-(4-chlorophenyl)-1H-tetrazol-5-yl]methyl}hexahydro-1H-azepine.

In a second aspect, there is provided a compound of formula (I), or a pharmaceutically acceptable salt thereof, for use in therapy, wherein
A is

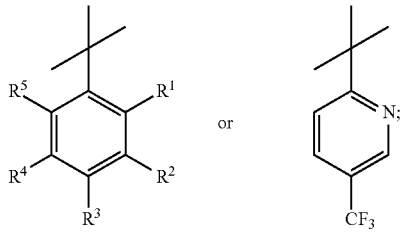

$R^1$ is hydrogen, methyl or chloro;
$R^2$ is hydrogen, trifluoromethyl, trifluoromethoxy, chloro or cyano;
$R^3$ is hydrogen, cyano, trifluoromethyl, trifluoromethoxy, difluoromethoxy, chloro, bromo, —S—$CH_3$, —$SO_2$—$C_{1-3}$alkyl or —$SF_5$;
$R^4$ is hydrogen, trifluoromethyl, trifluoromethoxy, chloro or cyano;
$R^5$ is hydrogen, methyl or chloro;
wherein at least one of $R^1$, $R^2$, $R^3$, $R^4$ or $R^5$ is a group other than hydrogen;
X is —$CH_2$—, —$CH_2$—$CH_2$— or —$CH(CH_3)$—;
wherein when $R^1$ is methyl, $R^5$ is hydrogen or chloro, and when $R^5$ is methyl, $R^1$ is hydrogen or chloro;
wherein when $R^2$ is chloro, $R^4$ is hydrogen, trifluoromethyl, trifluoromethoxy or cyano, and when $R^4$ is chloro, $R^2$ is hydrogen, trifluoromethyl, trifluoromethoxy or cyano;
$R^6$ is hydrogen and $R^7$ is $C_{1-5}$ alkyl or $C_{3-6}$cycloalkyl; or $R^6$ and $R^7$ together with the nitrogen atom to which they are attached form a saturated ring system B, where B is selected from a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —$SO_2$—$C_{1-3}$alkyl, $C_{1-3}$haloalkyl and —CO—$C_{1-3}$alkyl.

The term '$C_{1-3}$alkyl' and '$C_{1-5}$alkyl' as used herein as a group or a part of a group refers to a linear or branched saturated hydrocarbon group containing from 1 to 3 and 1 to 5 carbon atoms, respectively. Examples of $C_{1-3}$ alkyl include methyl, ethyl, n-propyl and isopropyl. Unless a particular structure is specified, the term propyl includes all straight and branched chain forms e.g. propyl includes n-propyl and iso-propyl.

The term $C_{3-6}$cycloalkyl as used herein refers to a saturated monocyclic hydrocarbon ring of 3 to 6 carbon atoms. Examples of such groups include cyclopropyl, cyclobutyl, cyclopentyl and cyclohexyl.

The term 'halogen' as used herein refers to a fluoro, chloro, bromo or iodo.

The term '$C_{1-3}$ haloalkyl' as used herein refers to a $C_{1-3}$ alkyl group as defined herein substituted with one or more halogen groups, e.g. $CF_3$, $CF_2H$ or $CF_3CH_2$.

The terms '4 to 7 membered monocyclic heterocyclic ring' and '5 to 6 membered heterocyclic ring' as used herein refer to a 4 to 6 membered saturated monocyclic ring and 5 to 6 membered saturated monocyclic ring, respectively, which contain 1 or 2 heteroatoms independently selected from oxygen, nitrogen and sulphur. Suitable examples of such rings include azetidine, pyrrolidine, piperidine, piperazine, morpholine and thiomorpholine.

The term '5 to 10 membered fused bicyclic ring system' as used herein refers to a '4 to 7 membered monocyclic heterocyclic ring' as defined hereinbefore wherein two neighbouring atoms (i.e. atoms bonded directly to each other) of the '4 to 7 membered monocyclic heterocyclic ring' form together a second monocyclic saturated ring which second ring contains 0, 1 or 2 heteroatoms independently selected from oxygen, nitrogen and sulphur.

The term 'bridged 4 to 7 membered monocyclic heterocyclic ring system' as used herein refers to a '4 to 7 membered monocyclic heterocyclic ring' as defined hereinbefore wherein two non-neighbouring carbon atoms (i.e. carbon atoms that are not bonded directly to each other) of the '4 to 7 membered monocyclic heterocyclic ring' are connected via a saturated —$(CH_2)_n$— carbon chain, where n is 1, 2 or 3. In one embodiment, n is 1 or 2. In a further embodiment, n is 1.

The term '7 to 11 membered spiro ring system' as used herein refers to a '4 to 7 membered monocyclic heterocyclic ring' as defined hereinbefore which is fused to a second 3 to 6 membered saturated ring via one single atom, and wherein the second ring contains 0, 1 or 2 heteroatoms independently selected from oxygen, nitrogen and sulphur.

In one embodiment of the first aspect, there is provided a compound of formula (Ia), or a salt thereof:

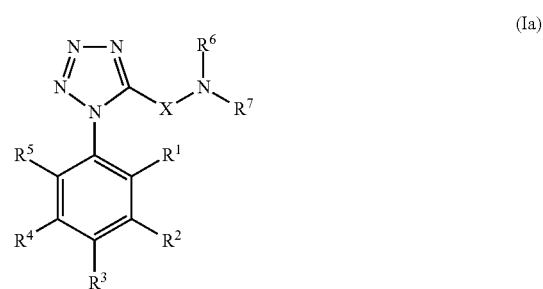

wherein
$R^1$ is hydrogen, methyl or chloro;
$R^2$ is hydrogen or trifluoromethyl;
$R^3$ is hydrogen, cyano, trifluoromethyl, trifluoromethoxy or chloro;
$R^4$ is hydrogen or trifluoromethyl;
$R^5$ is hydrogen, methyl or chloro;
X is —CH$_2$— or —CH$_2$—CH$_2$—;
wherein when $R^1$ is methyl, $R^5$ is hydrogen or chloro, and when $R^5$ is methyl, $R^1$ is hydrogen or chloro;
$R^6$ is hydrogen and $R^7$ is $C_{1-3}$ alkyl; or $R^6$ and $R^7$ together with the nitrogen atom to which they are attached form a 5 to 6 membered heterocyclyl ring or a 2,8-diazaspiro[4.5]decan-1-one group either of which is unsubstituted or substituted with 1 or 2 substituents independently selected from halogen, oxo and $C_{1-3}$ alkyl; with the proviso that the compound is not 4-{[1-(4-chlorophenyl)-1H-tetrazol-5-yl]methyl}morpholine, 4-({1-[3-(trifluoromethyl)phenyl]-1H-tetrazol-5-yl}methyl)morpholine hydrochloride or 4-({1-[3-(trifluoromethyl)phenyl]-1H-tetrazol-5-yl}methyl)morpholine.

In one embodiment of the second aspect, there is provided a compound of formula (Ia), or a pharmaceutically acceptable salt thereof, for use in therapy, wherein
$R^1$ is hydrogen, methyl or chloro;
$R^2$ is hydrogen or trifluoromethyl;
$R^3$ is hydrogen, cyano, trifluoromethyl, trifluoromethoxy or chloro;
$R^4$ is hydrogen or trifluoromethyl;
$R^5$ is hydrogen, methyl or chloro;
X is —CH$_2$— or —CH$_2$—CH$_2$—;
wherein when $R^1$ is methyl, $R^5$ is hydrogen or chloro, and when $R^5$ is methyl, $R^1$ is hydrogen or chloro;
$R^6$ is hydrogen and $R^7$ is $C_{1-3}$ alkyl; or $R^6$ and $R^7$ together with the nitrogen atom to which they are attached form a 5 to 6 membered heterocyclyl ring or 2,8-diazaspiro[4.5]decan-1-one group either of which is unsubstituted or substituted with 1 or 2 substituents independently selected from halogen, oxo and $C_{1-3}$ alkyl.

In one embodiment of the first or second aspect, $R^6$ is hydrogen and $R^7$ is $C_{1-5}$ alkyl or $C_{3-6}$ cycloalkyl; or $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —SO$_2$—C$_{1-3}$alkyl and $C_{1-3}$haloalkyl;
with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached forms a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —SO$_2$—C$_{1-3}$alkyl and $C_{1-3}$haloalkyl; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system; and
c) a bridged 4 to 7 membered monocyclic heterocyclic ring system;
which ring system B is unsubstituted or substituted with 1 to 3 substituents independently selected from halogen, oxo, $C_{1-3}$ alkyl, cyano, —SO$_2$—C$_{1-3}$alkyl and $C_{1-3}$haloalkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system; and
c) a bridged 4 to 7 membered monocyclic heterocyclic ring system;
which ring system B is unsubstituted or substituted with 1 to 3 substituents independently selected from halogen, oxo, $C_{1-3}$ alkyl, cyano, —SO$_2$—C$_{1-3}$alkyl and $C_{1-3}$haloalkyl; with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system; and
c) a bridged 4 to 7 membered monocyclic heterocyclic ring system;
which ring system B is unsubstituted or substituted with 1 to 3 substituents independently selected from halogen, oxo, $C_{1-3}$ alkyl, cyano, —SO$_2$—C$_{1-3}$alkyl and $C_{1-3}$haloalkyl;
with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
  pyrrolidine ring,
  morpholine ring,
  thiomorpholine ring,
  piperazine ring, and
  azetidine ring,
b) a 5 to 10 membered fused bicyclic ring system selected from
  octahydropyrrolo[1,2-a]pyrazine group,
  hexahydro-2H-isothiazolo[2,3-a]pyrazine group, and
  octahydro-pyrido[1,2-a]pyrazine group,
c) a bridged 4 to 7 membered monocyclic heterocyclic ring system selected from
  2-oxa-5-azabicyclo[2.2.1]heptane group, and
  2,5-diazabicyclo[2.2.1]heptane group;

which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
pyrrolidine ring,
morpholine ring,
thiomorpholine ring,
piperazine ring, and
azetidine ring,
b) a 5 to 10 membered fused bicyclic ring system selected from
octahydropyrrolo[1,2-a]pyrazine group,
hexahydro-2H-isothiazolo[2,3-a]pyrazine group, and
octahydro-pyrido[1,2-a]pyrazine group,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl;
with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
pyrrolidine ring,
morpholine ring,
thiomorpholine ring,
piperazine ring, and
azetidine ring,
b) a 5 to 10 membered fused bicyclic ring system selected from
octahydropyrrolo[1,2-a]pyrazine group,
hexahydro-2H-isothiazolo[2,3-a]pyrazine group, and
octahydro-pyrido[1,2-a]pyrazine group,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
pyrrolidine ring,
morpholine ring, and
piperazine ring, c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
pyrrolidine ring,
morpholine ring, and
piperazine ring,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
pyrrolidine ring,
morpholine ring, and
piperazine ring,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
pyrrolidine ring,
morpholine ring, and
piperazine ring,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from fluoro, oxo, methyl, ethyl, propyl, cyano, —$SO_2$—$CH_3$, —$SO_2$—$(CH_2)$$CH_3$, —$SO_2$—$(CH_2)_2CH_3$ and trifluoromethyl.

In one embodiment of the first or second aspect, $R^6$ and $R^7$ together with the nitrogen atom to which they are attached form a saturated ring system B, where B is selected from a) a 4 to 7 membered monocyclic heterocyclic ring selected from
  pyrrolidine ring,
  morpholine ring, and
  piperazine ring,
c) a bridged 4 to 7 membered monocyclic heterocyclic ring system selected from
  2-oxa-5-azabicyclo[2.2.1]heptane group, and
  2,5-diazabicyclo[2.2.1]heptane group;
which ring system B is unsubstituted or substituted with 1 to 3 substituents independently selected from fluoro, oxo, methyl, ethyl, propyl, cyano, —$SO_2$—$CH_3$, —$SO_2$—($CH_2$)$CH_3$, —$SO_2$—($CH_2$)$_2CH_3$ and trifluoromethyl; with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
  pyrrolidine ring,
  morpholine ring, and
  piperazine ring,
c) a bridged 4 to 7 membered monocyclic heterocyclic ring system selected from
  2-oxa-5-azabicyclo[2.2.1]heptane group, and
  2,5-diazabicyclo[2.2.1]heptane group;
which ring system B is unsubstituted or substituted with 1 to 3 substituents independently selected from fluoro, oxo, methyl, ethyl, propyl, cyano, —$SO_2$—$CH_3$, —$SO_2$—($CH_2$)$CH_3$, —$SO_2$—($CH_2$)$_2CH_3$ and trifluoromethyl; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, X is —$CH_2$—.

In one embodiment of the first or second aspect, $R^1$ is hydrogen or methyl, in particular hydrogen.

In one embodiment, $R^2$ is hydrogen, trifluoromethyl or chloro. In a further embodiment, $R^2$ is hydrogen or trifluoromethyl. In a still further embodiment, $R^2$ is hydrogen.

In one embodiment of the first or second aspect, $R^3$ is hydrogen, trifluoromethyl or cyano. In another embodiment of the first or second aspect, $R^3$ is trifluoromethyl or cyano. In a further embodiment of the first or second aspect, $R^3$ is trifluoromethyl.

In one embodiment of the first or second aspect, $R^2$ is trifluoromethyl and $R^3$ is cyano.

In one embodiment of the first or second aspect, $R^5$ is hydrogen or methyl. In a further embodiment, $R^5$ is hydrogen.

In one embodiment of the first or second aspect, $R^3$ is trifluoromethyl and $R^1$, $R^2$, $R^4$ and $R^5$ are hydrogen.

In one embodiment of the first or second aspect, $R^2$ is trifluoromethyl and $R^1$, $R^3$, $R^4$ and $R^5$ are hydrogen.

In one embodiment of the first or second aspect, $R^4$ is trifluoromethyl and $R^1$, $R^2$, $R^3$ and $R^5$ are hydrogen.

In one embodiment of the first or second aspect, $R^3$ is cyano and $R^1$, $R^2$, $R^4$ and $R^5$ are hydrogen.

In one embodiment of the first or second aspect, $R^2$ is trifluoromethyl, $R^3$ is cyano and $R^1$, $R^4$ and $R^5$ are hydrogen.

In one embodiment of the first or second aspect, $R^6$ is hydrogen and $R^7$ is $C_{1-5}$ alkyl or $C_{3-6}$cycloalkyl; or $R^6$ and $R^7$ together with the nitrogen atom to which they are attached forms a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—.

In one embodiment of the first or second aspect, $R^6$ is hydrogen and $R^7$ is $C_{1-5}$ alkyl or $C_{3-6}$cycloalkyl; or $R^6$ and $R^7$ together with the nitrogen atom to which they are attached forms a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ is hydrogen and $R^7$ is $C_{1-5}$ alkyl or $C_{3-6}$ cycloalkyl; or $R^6$ and $R^7$ together with the nitrogen atom to which they are attached forms a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system; and
c) a bridged 4 to 7 membered monocyclic heterocyclic ring system;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—.

In one embodiment of the first or second aspect, $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system; and
c) a bridged 4 to 7 membered monocyclic heterocyclic ring system;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that the compound is not
4-{5-[(3,4-dimethyl-1-piperazinyl)methyl]-1H-tetrazol-1-yl}benzonitrile dihydrochloride;
4-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system; and
c) a bridged 4 to 7 membered monocyclic heterocyclic ring system;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
　pyrrolidine ring,
　morpholine ring,
　thiomorpholine ring,
　piperazine ring, and
　azetidine ring,
b) a 5 to 10 membered fused bicyclic ring system selected from
　octahydropyrrolo[1,2-a]pyrazine group,
　hexahydro-2H-isothiazolo[2,3-a]pyrazine group, and
　octahydro-pyrido[1,2-a]pyrazine group,
c) a bridged 4 to 7 membered monocyclic heterocyclic ring system selected from
　2-oxa-5-azabicyclo[2.2.1]heptane group, and
　2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
　pyrrolidine ring,
　morpholine ring,
　thiomorpholine ring,
　piperazine ring, and
　azetidine ring,
b) a 5 to 10 membered fused bicyclic ring system selected from
　octahydropyrrolo[1,2-a]pyrazine group,
　hexahydro-2H-isothiazolo[2,3-a]pyrazine group, and
　octahydro-pyrido[1,2-a]pyrazine group,
c) a bridged 4 to 7 membered monocyclic heterocyclic ring system selected from
　2-oxa-5-azabicyclo[2.2.1]heptane group, and
　2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
　pyrrolidine ring,
　morpholine ring,
　thiomorpholine ring,
　piperazine ring, and
　azetidine ring,
b) a 5 to 10 membered fused bicyclic ring system selected from
　octahydropyrrolo[1,2-a]pyrazine group,
　hexahydro-2H-isothiazolo[2,3-a]pyrazine group, and
　octahydro-pyrido[1,2-a]pyrazine group,
c) a bridged 4 to 7 membered monocyclic heterocyclic ring system selected from
　2-oxa-5-azabicyclo[2.2.1]heptane group, and
　2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, $R^6$ and $R^7$ together with the nitrogen atom to which they are attached form a saturated ring system B, where B is selected from
$R^6$ and $R^7$ together with the nitrogen atom to which they are attached form a saturated ring system B, where B is selected from
a) a 4 to 7 membered monocyclic heterocyclic ring selected from
　pyrrolidine ring,
　morpholine ring, and
　piperazine ring,
c) a bridged 4 to 7 membered monocyclic heterocyclic ring system selected from
　2-oxa-5-azabicyclo[2.2.1]heptane group, and
　2,5-diazabicyclo[2.2.1]heptane group;

which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
 pyrrolidine ring,
 morpholine ring, and
 piperazine ring,
c) a bridged 4 to 7 membered monocyclic heterocyclic ring system selected from
 2-oxa-5-azabicyclo[2.2.1]heptane group, and
 2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

In one embodiment of the first or second aspect, $R^6$ and $R^7$ together with the nitrogen atom to which they are attached form a saturated ring system B, where B is selected from
a) a 4 to 7 membered monocyclic heterocyclic ring selected from
 pyrrolidine ring,
 morpholine ring, and
 piperazine ring,
c) a bridged 4 to 7 membered monocyclic heterocyclic ring system selected from
 2-oxa-5-azabicyclo[2.2.1]heptane group, and
 2,5-diazabicyclo[2.2.1]heptane group;
which ring system B is unsubstituted or substituted with 1 to 3 substituents independently selected from halogen, oxo, $C_{1-3}$ alkyl, cyano, —$SO_2$—$C_{1-3}$alkyl and $C_{1-3}$haloalkyl; $R^2$ is trifluoromethyl, $R^3$ is cyano, $R^1$, $R^4$ and $R^5$ are hydrogen, or $R^3$ is trifluoromethyl and $R^1$, $R^2$, $R^4$ and $R^5$ are hydrogen; X is —$CH_2$—; with the proviso that when $R^3$ is cyano and $R^6$ and $R^7$ together with the nitrogen atom to which they are attached form a piperazine ring, the piperazine ring is not solely substituted with $C_{1-3}$ alkyl.

In one embodiment of the first or second aspect, the compound is selected from
4-{5-[(1S,4S)-2-oxa-5-azabicyclo[2.2.1]hept-5-ylmethyl]-1H-tetrazol-1-yl}-2-(trifluoromethyl)benzonitrile;
4-({1-[3-(trifluoromethyl)phenyl]-1H-tetrazol-5-yl}methyl)morpholine;
4-{5-[(3,3-dimethyl-4-morpholinyl)methyl]-1H-tetrazol-1-yl}benzonitrile;
4-(5-{[(3R)-3-methyl-4-morpholinyl]methyl}-1H-tetrazol-1-yl)-2-(trifluoromethyl)benzonitrile;
1-(ethylsulfonyl)-4-({1-[3-(trifluoromethyl)phenyl]-1H-tetrazol-5-yl}methyl)piperazine;
(3R)-3-methyl-4-({1-[4-(trifluoromethyl)phenyl]-1H-tetrazol-5-yl}methyl)morpholine;
(3R)-3-methyl-4-({1-[3-(trifluoromethyl)phenyl]-1H-tetrazol-5-yl}methyl)morpholine;
and 3,3-Dimethyl-4-({1-[3-(trifluoromethyl)phenyl]-1H-tetrazol-5-yl}methyl)morpholine;
or a salt thereof.

In a further embodiment of the first or second aspect, the compound is selected from
4-{5-[(1S,4S)-2-oxa-5-azabicyclo[2.2.1]hept-5-ylmethyl]-1H-tetrazol-1-yl}-2-(trifluoromethyl)benzonitrile;
4-({1-[3-(trifluoromethyl)phenyl]-1H-tetrazol-5-yl}methyl)morpholine;
4-{5-[(3,3-dimethyl-4-morpholinyl)methyl]-1H-tetrazol-1-yl}benzonitrile;
4-(5-{[(3R)-3-methyl-4-morpholinyl]methyl}-1H-tetrazol-1-yl)-2-(trifluoromethyl)benzonitrile;
1-(ethylsulfonyl)-4-({1-[3-(trifluoromethyl)phenyl]-1H-tetrazol-5-yl}methyl)piperazine; and
(3R)-3-methyl-4-({1-[4-(trifluoromethyl)phenyl]-1H-tetrazol-5-yl}methyl)morpholine;
or a salt thereof.

Certain compounds as defined in the first or second aspect may in some circumstances form acid addition salts thereof. It will be appreciated that for use in medicine compounds as defined in the first or second aspect may be used as salts, in which case the salts should be pharmaceutically acceptable. Pharmaceutically acceptable salts include those described by Berge, Bighley and Monkhouse, J. Pharm. Sci., 1977, 66, 1-19. The term "pharmaceutically acceptable salts" includes salts prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Examples of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

It will be appreciated by those skilled in the art that certain protected derivatives of the compounds as defined in the first or second aspect, which may be made prior to a final deprotection stage, may not possess pharmacological activity as such, but may, in certain instances, be administered orally or parenterally and thereafter metabolised in the body to form compounds as defined in the first or second aspect which are pharmacologically active. Such derivatives may therefore be described as "prodrugs". All protected derivatives and prodrugs of compounds defined in the first or second aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds as defined in the first or second aspect. Therefore, in a further aspect, the invention provides a prodrug of a compound as defined in the first or second aspect.

It will be appreciated that certain compounds as defined in the first or second aspect, or their salts, may exist as solvates, such as hydrates. Where solvates exist, this invention includes within its scope stoichiometric and non-stoichiometric solvates.

It will be appreciated that certain compounds as defined in the first or second aspect, or their salts, may exist in more than one polymorphic form. The invention extends to all such forms whether in a pure polymorphic form or when admixed with any other material, such as another polymorphic form.

It will appreciated that certain compounds as defined in the first or second aspect, or their salts, may exist as tautomers. The invention also extends to any tautomeric forms and mixtures thereof.

Certain compounds as defined in the first or second aspect are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. In particular, there can be a chiral centre present within the compounds as defined in the first or second aspect when $R^6$ and $R^7$ together with the nitrogen atom to which they are attached form a saturated ring system B which is substituted.

The subject invention also includes isotopically-labelled compounds, which are identical to the compounds as defined in the first or second aspect, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$ and $^{18}F$.

Compounds as defined in the first or second aspect and salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds as defined in the first or second aspect and following of this invention can generally be prepared by carrying out the procedures disclosed in the Schemes and/or in the Examples below, by substituting a readily available isotopically labelled reagent for a non-isotopically labelled reagent. In one embodiment, compounds as defined in the first or second aspect or salts thereof are not isotopically labelled.

Throughout the specification, general formulae are designated by Roman numerals (I), (II), (III), (IV), etc. Subsets of these general formulae are defined as (Ia), (Ib), (Ic), etc. . . . (IVa), (IVb), (IVc), etc.

Compounds as defined in the first or second aspect may be prepared as set forth in the following Schemes and in the supporting compounds. The following processes form further aspects of the invention.

Compounds of formula (Ib) wherein X is —CH$_2$— or —CH$_2$(CH$_3$)— may be prepared according to Scheme 1:

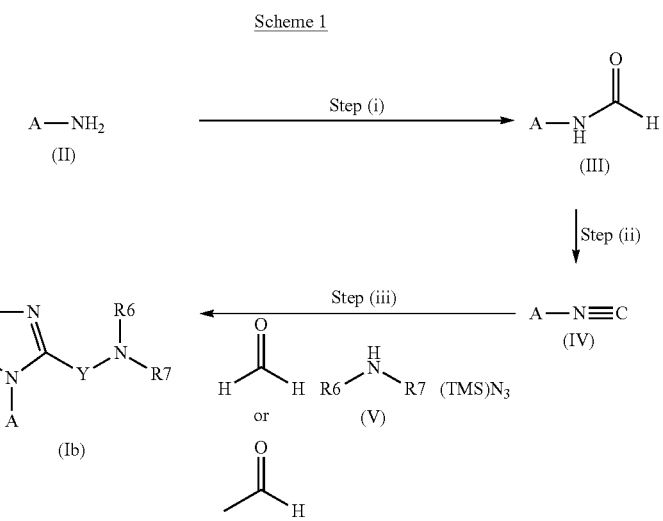

wherein A, $R^6$ and $R^7$ are as defined hereinbefore and Y is —CH$_2$— or —CH(CH$_3$)—.

Step (i): An intermediate of formula (III) may be prepared by reacting a compound of formula (II) with a formylating agent, for example 1H-1,2,3-benzotriazole-1-carbaldehyde, in a solvent, such as tetrahydrofuran. The reaction may be carried out at a temperature between ambient and elevated temperature (for example 70° C.). Compounds of formula (II) are either commercially available or may be prepared according to known methods.

Step (ii): The transformation of intermediate (III) to an isocyanide of formula (IV) may be achieved by treatment with a suitable dehydrating agent, for example phosphorous oxychloride, and a suitable base, for example potassium tert-butoxide, in a suitable solvent, such as tert-butanol, at a temperature between ambient and 35° C. Compounds of formula (IV) may also be commercially available.

Step (iii): Compounds of formula (Ib) may be prepared by reaction of an intermediate of formula (IV) with an amine of formula (V) and formaldehyde (37% aqueous) or acetaldehyde in the presence of trimethylsilylazide. The reaction may be carried out in a suitable solvent, for example methanol, at a suitable temperature, for example at ambient temperature.

Compounds of formula (V) are either commercially available, or may be prepared by known methods.

Compounds of formula (Ic) wherein X is —CH$_2$—CH$_2$— may be prepared according to Scheme 2:

tion with a compound of formula (V) in a suitable solvent, such as ethanol, in the presence of a suitable acid, for example acetic acid, or with the use of an acid salt of the amine of formula (V). The reaction may be carried out at a suitable temperature, for example at an elevated temperature such as 65° C. This transformation is followed by a reduction of the intermediate (X) to a compound of formula (Ic) which may be achieved with the use of a reducing agent, such as sodium triacetoxyborohydride, in an inert solvent, such as dichloromethane, at ambient temperature.

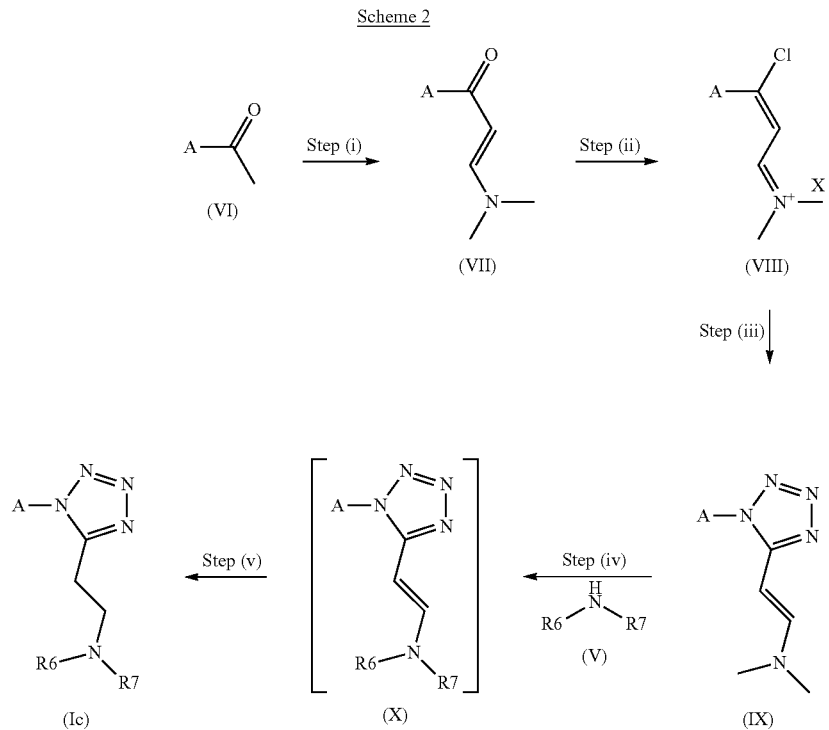

wherein A, R$^6$ and R$^7$ are as defined hereinbefore.

Step (i): An intermediate of formula (VII) may be prepared by reacting a compound of formula (VI) with dimethylformamide dimethylacetal (DMF-DMA). The reaction may be carried out at an elevated temperature (for example 100° C.). Compounds of formula (VI) are commercially available, or may be prepared by known methods.

Step (ii): The transformation of an intermediate of formula (VII) to a compound of formula (VIII) may be achieved by treatment with a chlorinating agent, for example phosphorous oxychloride, in an inert solvent, such as dichloromethane. This may be carried out at a suitable temperature between 0° C. and ambient. Compounds of formula (VIII) may be isolated as a salt, for example a perchlorate salt.

Step (iii): Compounds of formula (IX) are prepared by reaction of an intermediate of formula (VIII) with an inorganic azide, such as sodium azide, in a suitable solvent, for example methanol, at a suitable temperature, for example 60° C.

Step (iv): The transformation of an intermediate (IX) to a compound of formula (X) may be carried out through reac- Compounds of formula (Id) wherein X is —CH$_2$— may also be prepared according to the following Scheme 3:

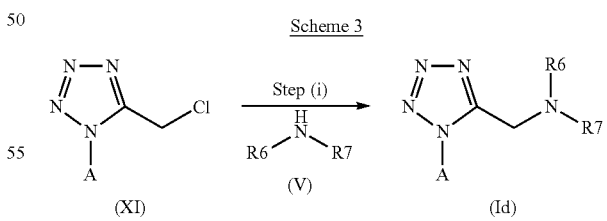

wherein A, R$^6$ and R$^7$ are as defined hereinbefore.

Step (i): A compound of formula (Id) may be prepared by the reaction of an amine of formula (V) with a compound of formula (XI), in a suitable solvent, such as acetonitrile, at a suitable temperature, for example at an elevated temperature such as 120° C. in a microwave reactor. Compounds of formula (XI) are commercially available, or may be prepared by methods known in the literature (for example as detailed in U.S. Pat. No. 2,470,084, Harvill et al.).

A compound of formula (If) wherein R³ is cyano may be prepared according to the following Scheme 4:

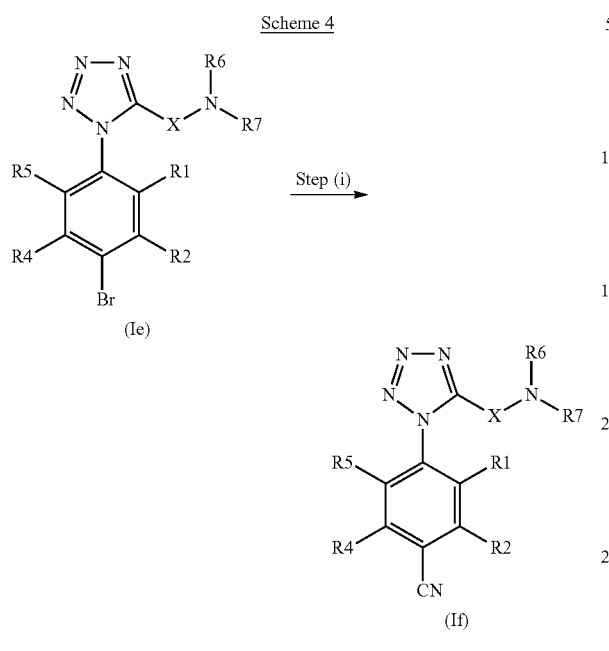

wherein X, R¹, R², R⁵, R⁶ and R⁷ are as defined hereinbefore.

Step (i): A compound of formula (Ie) may be converted to a compound of formula (If) by reaction with a metal cyanide, for example zinc cyanide, in the presence of a palladium catalyst and a suitable ligand, for example tris(dibenzlideneacetone)dipalladium(0) and 1,1'-bis(diphenylphosphino)ferrocene, in a suitable solvent, such as DMF, at elevated temperature, for example 120° C.

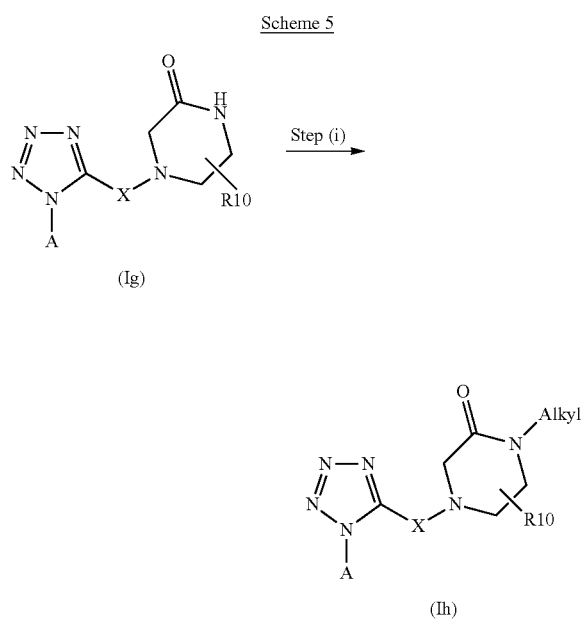

wherein X and A are as defined hereinbefore and R¹⁰ is a substituent as previously defined for compounds as defined in the first or second aspect.

Step (i): A compound of formula (Ig) may be converted to a compound of formula (Ih) with an additional N-alkyl substituent by treatment with a base, such as sodium hydride, followed by reaction with a suitable electrophile, such as an alkyl halide, in a solvent, such as DMF, at ambient temperature.

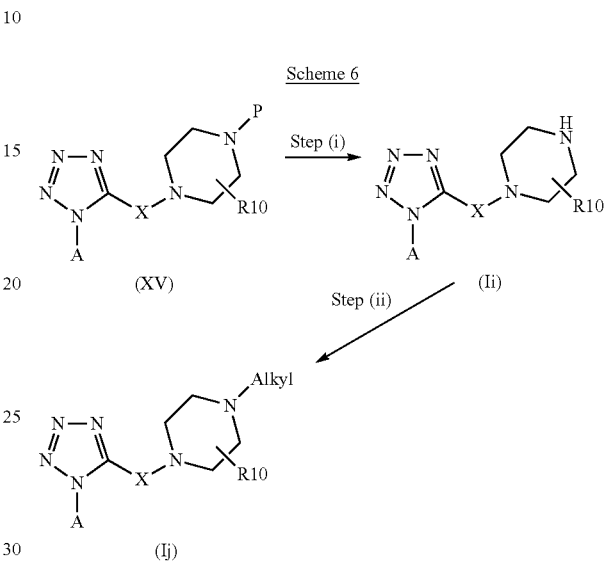

wherein X and A are as defined hereinbefore, R10 is a substituent as previously defined for compounds as defined in the first or second aspect and P is a suitable protecting group (for examples see 'Protective Groups In Organic Synthesis', T. Greene and P. Wuts, John Wiley and Sons Inc.), for example tert-butyloxycarbonyl (BOC).

Compounds of formula (XV) where R⁶ and R⁷ form a protected piperazine ring may be prepared according to Schemes 1, 2 or 3 using the corresponding protected piperazine.

Step (i): A compound of formula (XV) may be converted to a compound of formula (II) through a deprotection reaction, methods for which may be found in the literature for example in 'Protective Groups In Organic Synthesis', T. Greene and P. Wuts, John Wiley and Sons Inc. For example, if P is tert-butyloxycarbonyl (BOC), the deprotection step includes stirring in a suitable solvent, such as 1,4-dioxane, in the presence of a suitable acid, for example 4M HCl.

Step (ii): A compound of formula (II) may be converted to a compound of formula (Ij) with an additional N-alkyl substituent by treatment with a base, such as sodium hydride, followed by reaction with a suitable electrophile, such as an alkyl halide, in a solvent, such as DMF, at ambient temperature. Alternatively, a compound of formula (II) may be converted to a compound of formula (Ij) with an additional N-alkyl substituent by treatment with the relevant aldehyde or ketone, in the presence of a reducing agent, such as sodium triacetoxyborohydride, in a solvent, such as DCM, at ambient temperature.

Compounds of formula (XI) may also be prepared according to the following Scheme 7:

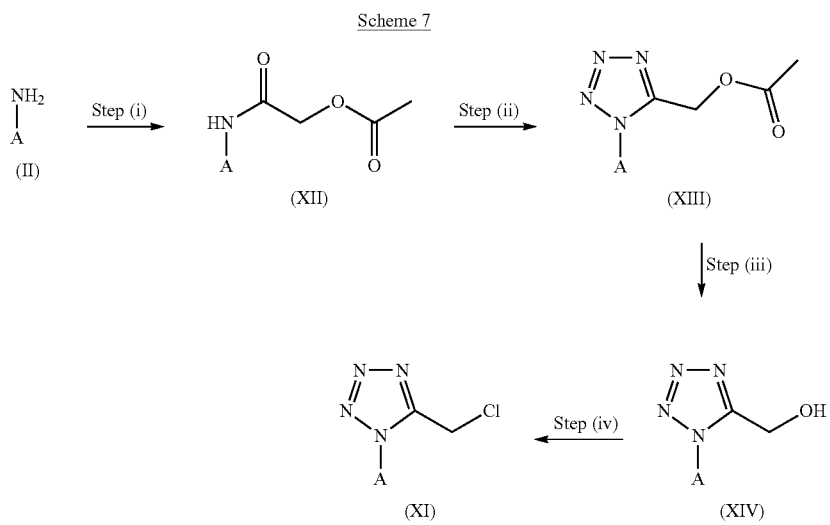

wherein A is as defined hereinbefore.

Step (i): An intermediate of formula (XII) may be prepared by reaction of a compound of formula (II) with 2-chloro-2-oxoethyl acetate in the presence of a base, such as triethylamine. The reaction may be carried out between 0° C. and ambient temperature in a solvent, such as dichloromethane.

Step (ii): An intermediate of formula (XIII) may be prepared from an intermediate of formula (XII) by treatment with triphenylphosphine, di-isopropyl azodicarboxylate and trimethylsilylazide in a solvent, such as tetrahydrofuran, at a temperature between ambient and elevated, for example ambient temperature.

Step (iii): An intermediate of formula (XIV) may be prepared from an intermediate of formula (XIII) by treatment with a source of hydroxide, for example lithium hydroxide, in a mixture of water and organic solvents, for example water, methanol and tetrahydrofuran, at a temperature between 0° C. and ambient temperature.

Step (iv): The transformation of an intermediate of formula (XIV) to an intermediate of formula (XI) may be achieved by treatment with a chlorinating agent, for example thionyl chloride, in a suitable solvent, such as a mixture of dichloromethane and N,N-dimethylformamide, at a temperature between 0° and ambient. Compounds of formula (XI) may also be commercially available.

Scheme 8

-continued wherein P is a suitable protecting group (for examples see 'Protective Groups in Organic Synthesis', T. Greene and P. Wuts, John Wiley and Sons Inc.), for example tert-butyloxycarbonyl (BOC), and R is a suitable group, for example p-toluene.

Step (i): An intermediate of formula (XVII) may be prepared by the reaction of a compound formula (XVI) with a suitable sulfonyl chloride (for example p-toluene sulfonyl chloride) in a suitable solvent, such as dichloromethane, in the presence of a base (for example triethylamine).

Step (ii): A compound of formula (XVII) may be converted to a compound of formula (XVIII) using a suitable base (for example sodium hydride) in a suitable solvent, such as N,N-dimethylformamide at a temperature between 0° C. and ambient temperature.

Step (iii): A compound of formula (XVIII) may be converted to a compound of formula (XIX) through a deprotection reaction, methods for which may be found in the literature. For example, if P is tert-butyloxycarbonyl (BOC), the deprotection step includes stirring in a suitable solvent, such as 1,4-dioxane, in the presence of a suitable acid, for example 4M HCl.

Scheme 9

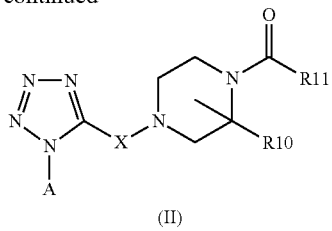

(II)

wherein X and A are defined as for compounds of the first or second aspect, R10 and R11 are substituent previously defined for compounds of the first or second aspect.

Step (i) A compound of formula (Ik) may be converted to a compound of formula (II) by treatment with an acid chloride in a suitable solvent, such as dichloromethane, in the presence of a base (for example triethylamine) at a temperature between 0° C. and ambient.

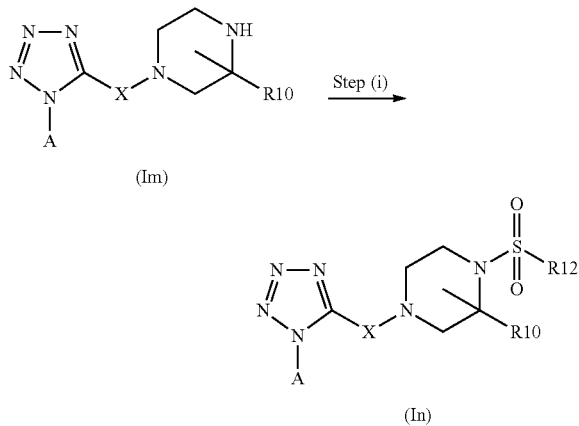

wherein X and A are defined hereinbefore, R10 and R12 are each a substituent as previously defined for compounds of the first or second aspect.

Step (i) A compound of formula (Im) may be converted to a compound of formula (In) by treatment with a sulfonyl chloride in a suitable solvent, such as dichloromethane, in the presence of a base (for example triethylamine) at a temperature between 0° C. and ambient.

The compounds as defined in the first or second aspect, or salts thereof, may be used to treat diseases for which blocking the $Ca_v2.2$ calcium channels is beneficial. Therefore, according to one aspect, the compounds as defined in the first or second aspect may be useful in the treatment or prophylaxis of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

'Chronic articular pain' conditions include rheumatoid arthritis, osteoarthritis, rheumatoid spondylitis, gouty arthritis and juvenile arthritis.

'Pain associated with functional bowel disorders' includes non-ulcer dyspepsia, non-cardiac chest pain and irritable bowel syndrome.

'Neuropathic pain' syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

'Inflammatory pain' conditions include skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastro esophageal reflux disease); organ transplantation; other conditions with an inflammatory component such as vascular disease, migraine, periarteritis nodosa, thyroiditis, aplastic anaemia, Hodgkin's disease, scleroderma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

Compounds as defined in the first or second aspect may also be useful in the treatment or prophylaxis of disorders treatable and/or preventable with anti-convulsive agents, such as epilepsy including post-traumatic epilepsy, obsessive compulsive disorders (OCD), bipolar disorders, sleep disorders (including circadian rhythm disorders, insomnia & narcolepsy), tics (e.g. Giles de la Tourette's syndrome), ataxias, muscular rigidity (spasticity), and temporomandibular joint dysfunction. "Epilepsy" is intended to include the following seizures: simple partial seizures, complex partial seizures, secondary generalised seizures, generalised seizures including absence seizures, myoclonic seizures, clonic seizures, tonic seizures, tonic clonic seizures and atonic seizures.

Another condition which could potentially be treated by compounds as defined in the first or second aspect is spasticity or muscular hypertonicity.

It is believed that compounds as defined in the first or second aspect are particularly useful in the treatment or prophylaxis of pain, more particularly neuropathic pain, inflammatory pain and migraine, and epilepsy.

Thus, in an embodiment of the second aspect, the therapy is to the treatment or prophylaxis of any of the disorders described herein, in particular pain. In one particular embodiment, the therapy is to the treatment of any of the disorders described herein, in particular pain.

According to a further aspect, there is provided a use of a compound as defined in the second aspect, or a pharmaceutically acceptable salt thereof, in the manufacture of a medicament for the treatment or prophylaxis of any of the disorders herein, in particular pain. More particularly, there is provided a use of a compound as defined in the second aspect, or a pharmaceutically acceptable salt thereof, in the manufacture of a medicament for the treatment of any of the disorders herein.

According to another aspect, there is provided a method of treatment or prophylaxis of any of the disorders herein, in particular pain in humans, which method comprises the administration to the human in need of such treatment or prophylaxis, an effective amount of a compound as defined in the second aspect, or a pharmaceutically acceptable salt thereof.

In the context of the present invention, the term "treatment" refers to symptomatic treatment and the term "prophylaxis" is used to mean preventing symptoms in an already afflicted subject or preventing recurrence of symptoms in an afflicted subject and is not limited to complete prevention of an affliction.

In order to use a compound as defined in the first or second aspect or a pharmaceutically acceptable salt thereof for the treatment or prophylaxis of humans and other mammals it is normally formulated in accordance with standard pharmaceutical practice as a pharmaceutical composition. Therefore in another aspect of the invention there is provided a pharmaceutical composition comprising a compound as defined in the first or second aspect, or a pharmaceutically acceptable salt thereof, adapted for use in human or veterinary medicine.

In order to use compounds as defined in the first or second aspect in therapy, they will normally be formulated into a pharmaceutical composition in accordance with standard pharmaceutical practice. The present invention also provides a pharmaceutical composition, which comprises a compound as defined in the first to fourth aspect, or a pharmaceutically acceptable salt thereof, and optionally a pharmaceutically acceptable excipient.

When used in the treatment or prophylaxis of pain, the compound as defined in the first or second aspect or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for Example sumatriptan, naratriptan, zolmitriptan, eletriptan, frovatriptan, almotriptan or rizatriptan; nicotinic acetyl choline (nACh) receptor modulators; glutamate receptor modulators, for Example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; additional COX-2 inhibitors are disclosed in U.S. Pat. No. 5,474,995, U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO00/52008, WO00/38311, WO01/58881 and WO02/18374.

The invention thus provides, in a further aspect, a combination comprising a compound as defined in the first or second aspect or a pharmaceutically acceptable salt thereof together with a further therapeutic agent or agents.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10% to 60% by weight, of the active material, depending on the method of administration. The dose of the compound as defined in the first or second aspect or a pharmaceutically acceptable salt thereof used in the treatment or prophylaxis of the aforementioned disorders will vary in the usual way with the seriousness of the disorders, the weight of the sufferer, and other similar factors. However, as a general guide suitable unit doses may be 0.05 to 1000 mg, more suitably 20 to 600 mg, and such unit doses may be administered more than once a day, for example two or three a day. Such therapy may extend for a number of weeks, months, years or even life.

A further aspect to the invention is a pharmaceutical composition comprising 0.05 to 1000 mg of a compound as defined in the first or second aspect or a pharmaceutically acceptable salt thereof, and 0 to 3 g more suitably 0 to 2 g of at least one pharmaceutically acceptable carrier.

All publications, including but not limited to patents and patent applications, cited in this specification are herein incorporated by reference as if each individual publication were specifically and individually indicated to be incorporated by reference herein as though fully set forth.

ABBREVIATIONS aq.: aqueous
DCM: dichloromethane
DMSO: dimethylsulfoxide
EtOAc: ethyl acetate
ES: electrospray
MS: mass spectrometry
MeCN: acetonitrile
MDAP: mass directed automated preparative liquid chromatography (for details see section 'Equipment').
MeOH: methanol
NMR: nuclear magnetic resonance
Rt: room temperature
sat.: saturated
SAX: strong anion exchange cartridge
SCX: strong cation exchange chromatography
SPE: solid phase extraction
THF: tetrahydrofuran
TMS: trimethylsilyl
Supporting Compounds The preparation of a number of supporting compounds as defined in the first or second aspect are described below. In the procedures that follow, after each starting material, reference to an intermediate is typically provided. This is provided merely for assistance to the skilled chemist. The starting material may not necessarily have been prepared from the batch referred to.

Intermediate 1:
[2-Chloro-4-(trifluoromethyl)phenyl]formamide

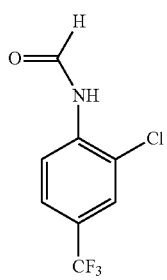 [SMILES: O=CNc1ccc(C(F)(F)F)cc1Cl]

To a solution of 2-chloro-4-(trifluoromethyl)aniline (500 mg, 2.56 mmol) in tetrahydrofuran (THF) (8 mL) was added 1H-1,2,3-benzotriazole-1-carbaldehyde (489 mg, 3.32 mmol, Sigma-Aldrich). The reaction mixture was heated to 70° C. and stirred for 18 hours. To the reaction mixture was added 1H-1,2,3-benzotriazole-1-carbaldehyde (1.16 mmol, 245 mg) and the reaction mixture heated to 70° C. for a further 5 hours. The reaction mixture was concentrated under vacuum and the residue partitioned between DCM (20 mL) and 2N HCl (10 mL). The organic layer was collected via a hydrophobic frit and the solvent removed under vacuum.

The crude product was purified by silica chromatography (Biotage SP4, eluting iso-hexane (5 column volumes) followed by a gradient from 0-20% EtOAc in iso-hexane (over 15 column volumes)) to yield the title compound as a solid (0.445 g)

$^1$H NMR (400 MHz, Chloroform-D) δ ppm 7.55 (m, 1H) 7.68 (d, J=1.5 Hz, 1H) 7.83 (br.s, 1H) 8.56 (d, J=1.3 Hz, 1H) 8.62 (d, J=8.6 Hz, 1H)

MS ES-ve m/z 222, 224 (M+H)

Intermediate 2: 3-(Dimethylamino)-1-[4-(trifluoromethyl)phenyl]-2-propen-1-one

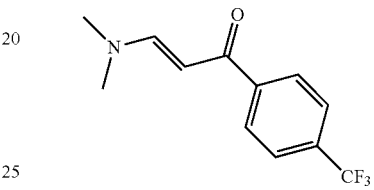

A solution of 1-[4-(trifluoromethyl)phenyl]ethanone (2 g, 10.63 mmol, Sigma-Aldrich) in dimethylformamide-dimethylacetal (5 ml, 37.3 mmol) was heated to 110° C. and stirred for 18 hours. The reaction mixture was cooled to room temperature then diluted with iso-hexanes (20 ml). The resulting precipitate was filtered then washed with a minimum of iso-hexane to yield the title compound as a yellow solid (1.29 g)

$^1$H NMR (400 MHz, Chloroform-D) δ ppm 2.95 (s, 3H) 3.18 (s, 3H) 5.68 (d, J=12.3 Hz, 1H) 7.67 (m, 2H) 7.84 (d, J=12.3 Hz, 1H) 7.98 (d, J=8.1 Hz, 2H)

Intermediate 3: N-{3-Chloro-3-[4-(trifluoromethyl)phenyl]-2-propen-1-ylidene}-N-methylmethanaminium perchlorate

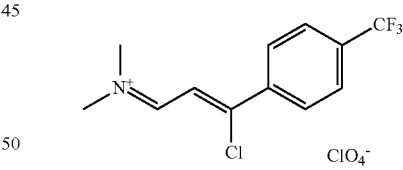

A solution of 3-(dimethylamino)-1-[4-(trifluoromethyl)phenyl]-2-propen-1-one (may be prepared as described in Intermediate 2) (1.49 g, 6.13 mmol) in dichloromethane (DCM) (6 ml) was cooled in an ice-water bath before the dropwise addition of POCl$_3$ (0.571 ml, 6.13 mmol). The ice-water bath was removed and the reaction mixture stirred at room temperature for 3 hours. The solvent was removed under vacuum to yield a solid. To the solid was then added to an ice-cold solution of sodium perchlorate (3.75 g, 30.6 mmol) in water (8 mL) and diethyl ether (2 mL). The resulting suspension was stirred in an ice-water bath for 20 minutes. The solid was then collected by filtration, washed with ice-cold water (4 mL), dried by suction for 40 minutes then dried overnight under vacuum to yield the title compound as a solid (2.39 g.

MS ES-ve m/z 222, 224 (M+H)
¹H NMR (400 MHz, DMSO-D6) δ ppm 3.71 (d, J=1.1 Hz, 3H) 3.80 (s, 3H) 7.85 (d, J=9.9 Hz, 1H) 8.00 (d, J=8.3 Hz, 2H) 8.28 (d, J=8.3 Hz, 2H) 9.06 (m, 1H)

Intermediate 4: Dimethyl(2-{1-[4-(trifluoromethyl)phenyl]-1H-tetrazol-5-yl}ethenyl)amine

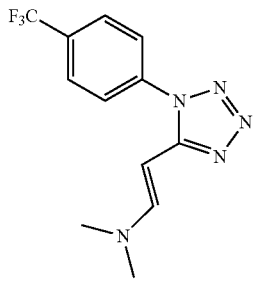 [SMILES: CN(C)/C=C/c1nnnn1-c1ccc(C(F)(F)F)cc1]

A suspension of sodium azide (0.698 g, 10.73 mmol) in methanol (15 ml) was heated to 60° C. before the portionwise addition of N-{3-chloro-3-[4-(trifluoromethyl)phenyl]-2-propen-1-ylidene}-N-methylmethanaminium perchlorate (may be prepared as described in Intermediate 3) (1.69 g, 4.67 mmol), allowing gas evolution to cease between additions. Upon complete addition, the reaction mixture was allowed to cool. Once at ambient temperature, the reaction mixture was diluted with water (10 mL) leading to precipitation. The suspension was filtered and the solid collected was washed with water (2×3 mL) then dried under vacuum overnight to yield the title compound as a solid (0.323 g).
¹H NMR (400 MHz, Chloroform-D) δ ppm 2.94 (s, 6H) 4.68 (d, J=12.9 Hz, 1H) 7.68 (d, J=8.1 Hz, 2H) 7.82 (d, J=12.9 Hz, 1H) 7.84 (d, J=8.3 Hz, 2H).

Intermediate 5: (2,4-Dichlorophenyl)formamide

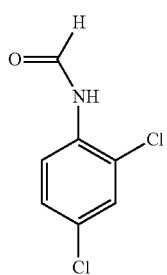 [SMILES: O=CNc1ccc(Cl)cc1Cl]

1H-1,2,3-benzotriazole-1-carbaldehyde (327 mg, 2.22 mmol, Sigma-Aldrich) was added to a solution of 2,4-dichloroaniline (300 mg, 1.85 mmol) in tetrahydrofuran (THF) (6 mL). The solution was heated to 60° C. and stirred for 22.5 h before concentrating in vacuo. The resulting solid was dissolved in DCM (30 ml), washed with 2M HCl (15 ml), the organic layer was passed through a hydrophobic frit and reduced in vacuo. Purification was carried out by silica column chromatography (Biotage SP4, gradient elution 0-100% EtOAc in iso-hexane) to yield the title compound (334 mg).
¹H NMR (400 MHz, DMSO-D6) δ ppm 7.43 (dd, J=8.9, 2.5 Hz, 1H) 7.68 (d, J=2.4 Hz, 1H) 8.14 (d, J=8.8 Hz, 1H) 8.36 (s, 1H) 9.99 (br.s, 1H)
MS ES-ve m/z 190 (M+H)

Intermediate 6: {4-[(Trifluoromethyl)oxy]phenyl}formamide

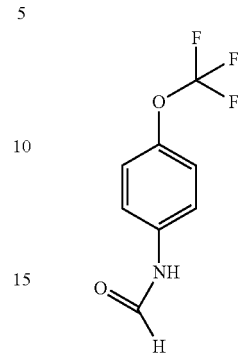

1H-1,2,3-benzotriazole-1-carbaldehyde (299 mg, 2.032 mmol, Sigma-Aldrich) was added to a solution of 4-[(trifluoromethyl)oxy]aniline (0.227 mL, 1.694 mmol) in tetrahydrofuran (THF) (6 mL). The solution was heated to 60° C. and stirred for 22.5 hours. 1H-1,2,3-benzotriazole-1-carbaldehyde (199 mg, 1.355 mmol) was added and the reaction mixture stirred for a further 20 hours before concentrating in vacuo. The resulting solid was dissolved in DCM (30 ml), washed with 2M HCl (15 ml), the organic layer was passed through a hydrophobic frit and reduced in vacuo. The crude material was purified by silica chromatography (Biotage SP4, eluting iso-hexane (5 column volumes) followed by a gradient from 0-20% EtOAc in iso-hexane (over 15 column volumes)) to yield the title compound as a white solid (0.338 g).
MS ES-ve m/z 206 (M+H)

Intermediate 7: 2-[(4-Cyanophenyl)amino]-2-oxoethyl acetate

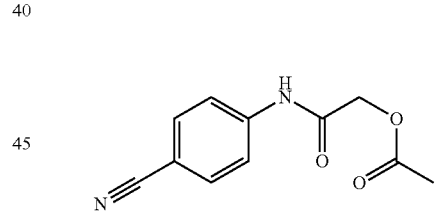

A solution of 4-aminobenzonitrile (5 g, 42.3 mmol) and triethylamine (7.08 mL, 50.8 mmol) in dichloromethane (DCM) (40 mL) was cooled in an ice-water bath before the dropwise addition of 2-chloro-2-oxoethyl acetate (5.46 mL, 50.8 mmol). The reaction mixture was allowed to warm to room temperature and stirred for 18 hours. The reaction mixture was diluted with DCM (50 mL) and the resulting solution washed with 2N HCl (50 mL). On mixing, precipitation occurred and the solid collected was filtered and dried under vacuum at 40° C. for 4 hours to yield a pale brown solid. The solid was dissolved in DCM (150 mL) and washed with 2N HCl (50 mL). The organic layer was collected via a hydrophobic frit and the solvent removed to yield the title compound as a cream solid (4.48 g).
¹H NMR (400 MHz, CHLOROFORM-d) δ ppm 2.25 (s, 3H) 4.72 (s, 2H) 7.64 (d, J=9.0 Hz, 2H) 7.71 (d, J=9.0 Hz, 2H) 8.02 (br. s., 1H)

Intermediate 8:
[1-(4-Cyanophenyl)-1H-tetrazol-5-yl]methyl acetate

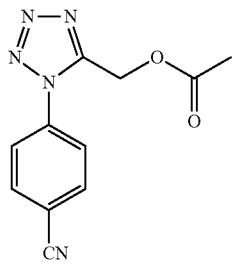 [SMILES: CC(=O)OCc1nnnn1-c1ccc(C#N)cc1]

To a solution of 2-[(4-cyanophenyl)amino]-2-oxoethyl acetate (3.48 g, 15.95 mmol, Intermediate 7) in tetrahydrofuran (THF) (200 mL) was added triphenylphosphine (8.37 g, 31.9 mmol), di-isopropyl azodicarboxylate (6.20 mL, 31.9 mmol) and trimethylsilylazide (4.23 mL, 31.9 mmol). The reaction mixture was stirred at room temperature for 18 hours. The majority of the solvent was removed under vacuum and the residue purified by silica chromatography (Biotage SP4, eluting 30% EtOAc in iso-hexane (5 column volumes) then a gradient from 30-40% ethyl acetate in iso-hexane (over 7 column volumes)) to yield the title compound as a white solid (2.68 g).

$^1$H NMR (400 MHz, CHLOROFORM-d) δ ppm 2.08 (s, 3H) 5.41 (s, 2H) 7.74 (d, J=8.8 Hz, 2H) 7.94 (m, J=8.8 Hz, 2H)

Intermediate 9:
4-[5-(Hydroxymethyl)-1H-tetrazol-1-yl]benzonitrile

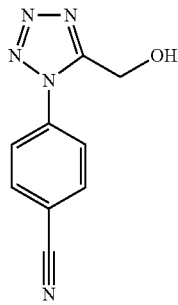 [SMILES: N#Cc1ccc(-n2nnnc2CO)cc1]

To a solution of [1-(4-cyanophenyl)-1H-tetrazol-5-yl]methyl acetate (2.48 g, 10.2 mmol, Intermediate 8) in water (15 mL), methanol (15 mL) and tetrahydrofuran (THF) (30 mL), cooled in an ice bath, was added lithium hydroxide (0.244 g, 10.2 mmol). The reaction mixture was stirred at 0-5° C. for 1.5 hours. The reaction mixture was acidified with the addition of 2N HCl (5.5 ml). The majority of the organic solvent was then removed from the reaction mixture under vacuum leading to precipitation of a white solid which was filtered then dried under vacuum at 40° C. for 18 hours to yield the title compound as a white solid (1.43 g)

$^1$H NMR (400 MHz, DMSO-$d_6$) δ ppm 4.85 (d, J=5.7 Hz, 2H) 6.03 (t, J=5.9 Hz, 1H) 8.00 (d, J=8.6 Hz, 2H) 8.17 (m, J=8.5 Hz, 2H)

Intermediate 10:
4-[5-(Chloromethyl)-1H-tetrazol-1-yl]benzonitrile

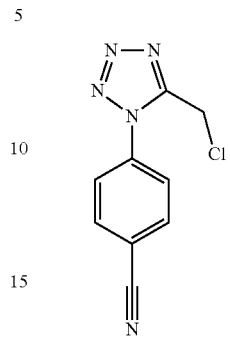

To a solution of 4-[5-(hydroxymethyl)-1H-tetrazol-1-yl]benzonitrile (1.43 g, 7.11 mmol, Intermediate 9) in dichloromethane (DCM) (20 mL) and N,N-dimethylformamide (DMF) (3 mL), cooled in an ice bath under argon, was added dropwise thionyl chloride (0.545 mL, 7.46 mmol). The reaction mixture was stirred at 0-5° C. for three hours.

To the reaction mixture was added water (20 mL) and DCM (20 mL) and the reaction mixture partitioned through a hydrophobic frit. The organic layer was evaporated to dryness under vacuum. The residue was purified by silica chromatography (Biotage SP4, eluting 20% EtOAc in iso-hexane (4 column volumes) then a gradient from 20-60% EtOAc in iso-hexane (over 11 column volumes)). Fractions containing the desired product were combined and the solvent removed to yield the title compound as a white solid (1.35 g).

$^1$H NMR (400 MHz, CHLOROFORM-d) δ ppm 4.86 (s, 2H) 7.82 (d, J=8.8 Hz, 2H) 7.96 (d, J=8.8 Hz, 2H)

Intermediate 11: 1,1-Dimethylethyl 2,2-dimethyl-4-({1-[3-(trifluoromethyl)phenyl]-1H-tetrazol-5-yl}methyl)-1-piperazinecarboxylate

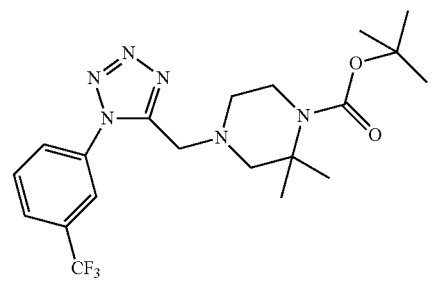 [SMILES: CC(C)(C)OC(=O)N1CCN(Cc2nnnn2-c2cccc(C(F)(F)F)c2)CC1(C)C]

To a solution of 5-(chloromethyl)-1-[3-(trifluoromethyl)phenyl]-1H-tetrazole (440 mg, 1.68 mmol, commercially available from Otava, Kiev, Ukraine) in acetonitrile (8 mL) was added 1,1-dimethylethyl 2,2-dimethyl-1-piperazinecarboxylate (359 mg, 1.68 mmol, commercially available, for example from ChemPacific Corp., Baltimore, USA) and triethylamine (0.701 mL, 5.03 mmol). The mixture was then heated to 120° C. for 20 minutes in a microwave reactor.

The product was concentrated in vacuo. The crude product was purified by silica chromatography (Biotage SP4), eluting with 10% ethyl acetate in hexane (3 column volumes) then a gradient from 10-40% ethyl acetate in hexane (15 column volumes) then 40% ethyl acetate in hexane (3 column volumes). The relevant fractions were combined and concentrated to yield the title compound as white crystals (567 mg).

MS ES+ve m/z 441 (M+H)

$^1$H NMR (400 MHz, DMSO-$d_5$) δ ppm 1.02 (s, 6H) 1.35 (s, 9H) 2.12 (s, 2H) 2.28-2.34 (m, 2H) 3.09 (m, 2H) 3.94 (s, 2H) 7.84-7.92 (m, 1H) 8.01 (d, J=7.9 Hz, 1H) 8.11 (d, J=8.1 Hz, 1H) 8.27 (s, 1H)

Intermediate 12: 3,3-Dimethyl-1-({1-[3-(trifluoromethyl)phenyl]-1H-tetrazol-5-yl}methyl)piperazine

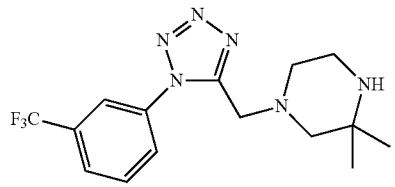 [SMILES: CC1(C)CN(Cc2nnnn2-c2cccc(C(F)(F)F)c2)CCN1]

To a solution of 1,1-dimethylethyl 2,2-dimethyl-4-({1-[3-(trifluoromethyl)phenyl]-1H-tetrazol-5-yl}methyl)-1-piperazinecarboxylate (567 mg, 1.287 mmol, Intermediate 11) in methanol was added 4M hydrogen chloride in 1,4-Dioxane (7 ml, 28.0 mmol). The reaction mixture was stirred at room temperature for 1 hour.

The reaction mixture was concentrated in vacuo. The crude product was poured onto a 5 g SCX cartridge, washed with methanol (2 column volumes) and eluted with ammonia in methanol (2 column volumes). The ammonia in methanol fractions were concentrated and the product dried in vacuo to yield the title compound as white crystals (410 mg).

MS ES+ve m/z 341 (M+H)

$^1$H NMR (400 MHz, METHANOL-$d_4$) δ ppm 0.93 (s, 6H) 2.17 (br. s., 2H) 2.36 (br. s., 2H) 2.72 (t, J=5.2 Hz, 2H) 3.35 (s, 1H) 3.86 (s, 2H) 7.83-7.89 (m, 1H) 7.94 (d, J=7.9 Hz, 1H) 8.07 (d, J=7.9 Hz, 1H) 8.25 (s, 1H)

Intermediate 13: 1,1-Dimethylethyl (3R)-3-methyl-1-piperazinecarboxylate

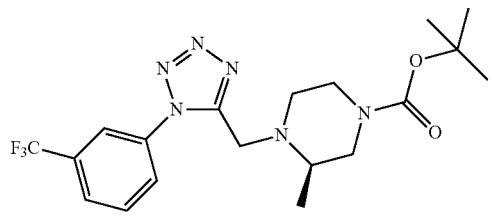

To a solution of 5-(chloromethyl)-1-[3-(trifluoromethyl)phenyl]-1H-tetrazole (500 mg, 1.90 mmol, commercially available from Otava, Kiev, Ukraine) in acetonitrile (7 mL) was added triethylamine (0.796 mL, 5.71 mmol) and 1,1-dimethylethyl (3R)-3-methyl-1-piperazinecarboxylate (419 mg, 2.094 mmol, commercially available, for example from Sigma Aldrich, St Louis, USA). The reaction mixture was heated for 20 min at 120° C. in a microwave reactor.

The product was concentrated in vacuo. The crude product was purified by silica chromatography (Biotage SP4), eluting with 10% ethyl acetate in hexane (3 column volumes) then a gradient from 10-40% ethyl acetate in hexane (over 15 column volumes) then 40% ethyl acetate in hexane (3 column volume). The relevant fractions were combined, concentrated and dried in vacuo to yield the title compound as a light yellow oil (527 mg).

MS ES+ve m/z 427 (M+H)

$^1$H NMR (400 MHz, METHANOL-$d_4$) δ ppm 0.92 (d, J=6.1 Hz, 3H) 1.43 (s, 9H) 2.18-2.28 (m, 1H) 2.42-2.51 (m, 1H) 2.54-2.63 (m, 1H) 2.79 (br. s., 1H) 2.98-3.07 (m, 1H) 3.36-3.49 (m, 2H) 3.82 (d, J=14.7 Hz, 1H) 4.22 (d, J=14.7 Hz, 1H) 7.85 (m, 1H) 7.97 (d, J=7.9 Hz, 1H) 8.00 (d, J=7.9 Hz, 1H) 8.23 (s, 1H)

Intermediate 14: (2R)-2-Methyl-1-({1-[3-(trifluoromethyl)phenyl]-1H-tetrazol-5-yl}methyl)piperazine

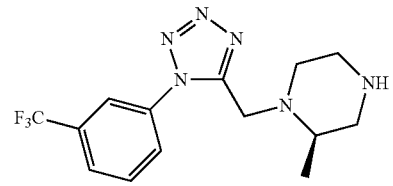 [SMILES: C[C@@H]1CNCCN1Cc1nnnn1-c1cccc(C(F)(F)F)c1]

To a solution of 1,1-dimethylethyl (3R)-3-methyl-4-({1-[3-(trifluoromethyl)phenyl]-1H-tetrazol-5-yl}methyl)-1-piperazinecarboxylate (527 mg, 1.236 mmol, Intermediate 13) in methanol was added 4M hydrogen chloride in 1,4-dioxane (7 mL, 28.0 mmol). The reaction mixture was stirred at room temperature for 1 hour. The reaction mixture was concentrated in vacuo to give white crystals. The crude product was poured onto a 5 g SCX cartridge, washed with methanol (2 column volumes) and eluted with ammonia in methanol (2 column volumes). The ammonia in methanol fractions were concentrated and dried in vacuo to yield the title compound as a yellow oil (389 mg).

MS ES+ve m/z 327 (M+H)

$^1$H NMR (400 MHz, METHANOL-$d_4$) δ ppm 0.88 (d, J=6.1 Hz, 3H) 2.18-2.30 (m, 2H) 2.34-2.43 (m, 1H) 2.47-2.56 (m, 2H) 2.69-2.77 (m, 2H) 3.35 (s, 1H) 3.74 (d, J=14.5 Hz, 1H) 4.28 (d, J=14.5 Hz, 1H) 7.82-7.89 (m, 1H) 7.96 (d, J=8.1 Hz, 1H) 7.99 (d, J=8.1 Hz, 1H) 8.24 (s, 1H)

Intermediate 15—1,1-Dimethylethyl 4-({1-[4-(trifluoromethyl)phenyl]-1H-tetrazol-5-yl}methyl)-1-piperazinecarboxylate

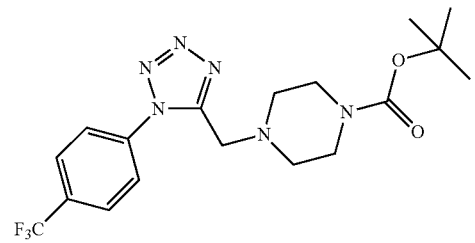

To a solution of 5-(chloromethyl)-1-[4-(trifluoromethyl)phenyl]-1H-tetrazole (500 mg, 1.90 mmol, commercially available from UkrOrgSynthesis, Kiev, Ukraine) in acetonitrile (10 mL) was added 1,1-dimethylethyl 1-piperazinecarboxylate (390 mg, 2.09 mmol) and triethylamine (0.796 mL, 5.71 mmol). The mixture was then heated to 120° C. for 20 min in a microwave reactor.

The reaction mixture was concentrated. The crude product was purified by silica chromatography (Biotage SP4), eluting with 20% ethyl acetate in hexane (3 column volumes) then a gradient from 20-50% ethyl acetate in hexane (15 column volumes) then 50% ethyl acetate in hexane (3 column volumes). The relevant fractions were combined and concentrated in vacuo to yield the title compound as white crystals (613 mg).

MS ES+ve m/z 413 (M+H)

$^1$H NMR (400 MHz, METHANOL-$d_4$) δ ppm 1.44 (s, 9H) 2.43-2.49 (m, 4H) 3.26-3.37 (m, 4H) 3.92 (s, 2H) 7.98 (d, J=8.6 Hz, 2H) 8.03 (d, J=8.6 Hz, 2H)

Intermediate 16: (3S)-3-Methyl-4-({1-[4-(trifluoromethyl)phenyl]-1H-tetrazol-5-yl}methyl)-2-piperazinone

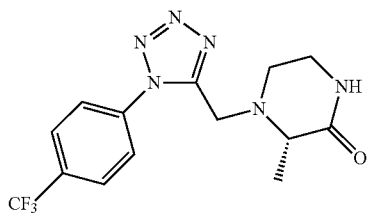

To a solution of 5-(chloromethyl)-1-[4-(trifluoromethyl)phenyl]-1H-tetrazole (500 mg, 1.90 mmol, commercially available from UkrOrgSynthesis, Kiev, Ukraine) in acetonitrile (8 mL) was added triethylamine (0.796 mL, 5.71 mmol) and (3S)-3-methyl-2-piperazinone (239 mg, 2.09 mmol, commercially available, for example from Sigma Aldrich, St Louis, USA). The reaction mixture was heated to 120° C. for 20 min. The reaction mixture was concentrated in vacuo and the crude product purified by reverse phase chromatography (Biotage SP4). The relevant fractions were combined, concentrated and dried in vacuo to yield the title compound as white crystals (349 mg).

MS ES+ve m/z 341 (M+H)

$^1$H NMR (400 MHz, METHANOL-$d_4$) δ ppm 1.20 (d, 3H, J=7 Hz) 2.55-2.65 (m, 1H) 2.86-2.95 (m, 1H) 3.05-3.25 (m, 3H) 4.05 (d, J=14.7 Hz, 1H) 4.25 (d, J=14.7 Hz, 1H) 7.93-8.00 (m, 4H)

Intermediate 17: 1,1-Dimethylethyl (1S,4S)-5-({1-[4-(trifluoromethyl)phenyl]-1H-tetrazol-5-yl}methyl)-2,5-diazabicyclo[2.2.1]heptane-2-carboxylate

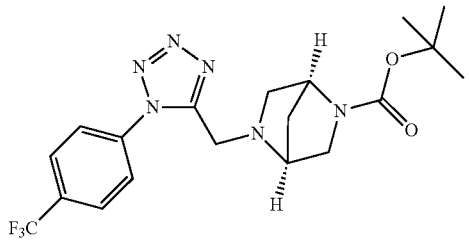

To a solution of 5-(chloromethyl)-1-[4-(trifluoromethyl)phenyl]-1H-tetrazole (500 mg, 1.90 mmol, commercially available from UkrOrgSynthesis, Kiev, Ukraine) in acetonitrile (10 mL) was added 1,1-dimethylethyl (1S,4S)-2,5-diazabicyclo[2.2.1]heptane-2-carboxylate (377 mg, 1.90 mmol, commercially available, for example from Sigma Aldrich Corporation) and triethylamine (0.796 mL, 5.71 mmol). The mixture was then heated to 120° C. for 20 min in a microwave reactor.

The reaction mixture was concentrated in vacuo to yield grey crystals. The crude product was purified by silica chromatography (Biotage SP4), eluting with 20% ethyl acetate in hexane (3 column volumes) then a gradient from 20-50% ethyl acetate in hexane (15 column volumes) then 50% ethyl acetate in hexane (3 column volumes). The relevant fractions were combined and concentrated in vacuo to yield the title compound as white crystals (480 mg).

MS ES+ve m/z 425 (M+H)

$^1$H NMR (400 MHz, METHANOL-$d_4$) rotameric mixture, δ ppm 1.43/1.45 (2×s, 9H) 1.67-1.76 (m, 1H) 1.78-1.84 (m, 1H) 2.63-2.70 (m, 1H) 2.80-2.89 (m, 1H) 3.13-3.18 (m, 1H) 3.33-3.39 (m, 1H) 3.47-3.54 (m, 1H) 4.11-4.20 (m, 2H) 4.28 (br. s., 1H) 7.97 (d, J=9.0 Hz, 2H) 8.00 (d, J=9.0 Hz, 2H)

Intermediate 18: (3R)-3-Methyl-4-({1-[4-(trifluoromethyl)phenyl]-1H-tetrazol-5-yl}methyl)-2-piperazinone

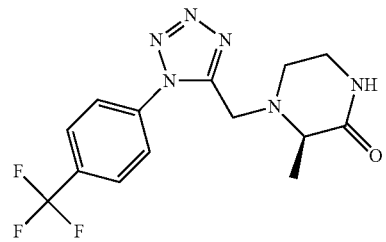

To a solution of 5-(chloromethyl)-1-[4-(trifluoromethyl)phenyl]-1H-tetrazole (500 mg, 1.90 mmol, commercially available from UkrOrgSynthesis, Kiev, Ukraine) in acetonitrile (8 mL) was added triethylamine (0.796 mL, 5.71 mmol) and (3R)-3-methyl-2-piperazinone (239 mg, 2.09 mmol, commercially available, for example from Sigma Aldrich, St Louis, USA). The reaction mixture was heated to 120° C. for 20 min.

The reaction mixture was concentrated in vacuo and the crude product purified by reverse phase chromatography (Biotage SP4). The relevant fractions were combined, concentrated and dried in vacuo to yield the title compound as white crystals (327 mg)

MS ES+ve m/z 341 (M+H)

$^1$H NMR (400 MHz, METHANOL-$d_4$) δ ppm 1.20 (d, J=7.0 Hz, 3H) 2.54-2.65 (m, 1H) 2.85-2.94 (m, 1H) 3.05-3.24 (m, 3H) 4.05 (d, J=14.7 Hz, 1H) 4.25 (d, J=14.9 Hz, 1H) 7.92-8.02 (m, 4H)

Intermediate 19: 1,1-Dimethylethyl 2,2-dimethyl-4-({1-[4-(trifluoromethyl)phenyl]-1H-tetrazol-5-yl}methyl)-1-piperazinecarboxylate

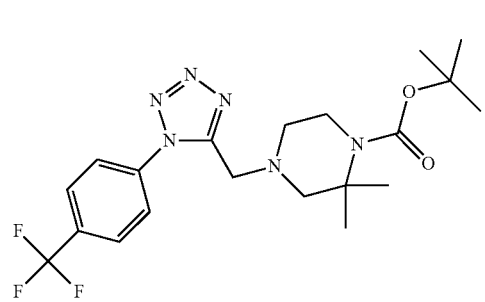

To a solution of formaldehyde (0.044 mL, 0.584 mmol) in methanol (2 mL) was added 1,1-dimethylethyl 2,2-dimethyl-1-piperazinecarboxylate (125 mg, 0.584 mmol, commercially available, for example from ChemPacific Corp., Baltimore, USA). The reaction mixture was stirred at room temperature for 1 hour before the addition of 4-(trifluoromethyl)phenylisocyanide (100 mg, 0.584 mmol, Fluorochem, Old Glossop, UK) and trimethylsilyl azide (0.092 mL, 0.701 mmol). The resulting reaction mixture was stirred at room temperature overnight.

The product was diluted with DCM (20 mL) and washed with water (10 mL). The aqueous phase was washed with DCM (2×10 mL) and all of the organic phases were combined and concentrated in vacuo. The crude product was purified by silica chromatography (Biotage SP4), eluting with 10% ethyl acetate in hexane (3 column volumes) then a gradient from 10-30% ethyl acetate in hexane (15 column volumes) then 30% ethyl acetate in hexane (3 column volumes). The relevant fractions were combined and concentrated to yield the title compound as a yellow oil (163 mg).

MS ES+ve m/z 341 (M-BOC+H)

¹H NMR (400 MHz, METHANOL-d₄) δ ppm 1.19 (s, 6H) 1.42 (s, 9H) 2.26 (s, 2H) 2.37-2.44 (m, 2H) 3.24-3.29 (m, 2H) 3.91 (s, 2H) 7.97 (d, J=8.6 Hz, 2H) 8.03 (d, J=8.6 Hz, 2H)

Intermediate 20: 1,1-Dimethylethyl 2-methyl-4-({1-[4-(trifluoromethyl)phenyl]-1H-tetrazol-5-yl}methyl)-1-piperazinecarboxylate

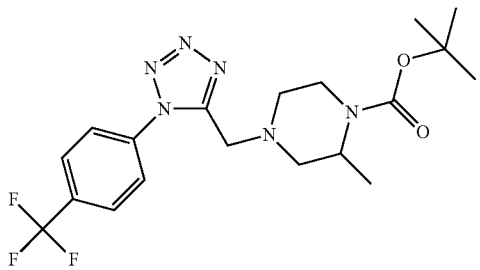

To a solution of formaldehyde (0.044 mL, 0.584 mmol) in methanol (2 mL) was added 1,1-dimethylethyl 2-methyl-1-piperazinecarboxylate (117 mg, 0.584 mmol). The reaction mixture was stirred at room temperature for 1 hour before the addition of 4-(trifluoromethyl)phenylisocyanide (100 mg, 0.584 mmol) and trimethylsilyl azide (0.092 mL, 0.701 mmol). The resulting reaction mixture was stirred at room temperature overnight.

The product was diluted with DCM (20 mL) and washed with water (10 mL). The aqueous phase was washed with DCM (2×10 mL) and all of the organic phases were combined and concentrated in vacuo. The crude product was purified by reverse phase chromatography (Biotage SP4). The relevant fractions were combined and concentrated in vacuo to yield the title compound as a colourless oil (129 mg).

MS ES+ve m/z 427 (M+H)

¹H NMR (400 MHz, METHANOL-d₄) δ ppm 0.90 (d, J=6.8 Hz, 3H) 2.08 (td, J=11.7, 3.5 Hz, 1H) 2.32 (dd, J=11.3, 3.8 Hz, 1H) 2.58 (d, J=11.2 Hz, 1H) 2.63-2.70 (m, 1H) 2.85 (td, J=12.8, 3.1 Hz, 1H) 3.68-3.76 (m, 1H) 3.89 (d, J=14.3 Hz, 1H) 3.95 (d, J=14.5 Hz, 1H) 4.09-4.17 (m, 1H) 7.97 (d, J=8.6 Hz, 2H) 8.03 (m, J=8.6 Hz, 2H)

Intermediate 21: 2-{[4-cyano-3-(trifluoromethyl)phenyl]amino}-2-oxoethyl acetate

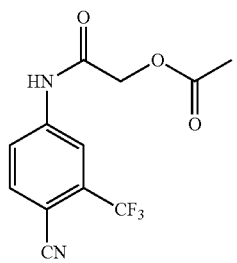 [SMILES: CC(=O)OCC(=O)Nc1ccc(C#N)c(C(F)(F)F)c1]

To a stirred solution of 4-amino-2-(trifluoromethyl)benzonitrile (commercially available, for example from Maybridge, Cornwall, United Kingdom, 85.0 g) in DCM (1 liter) at 0° C. was added triethylamine (92.2 g, 0.913 mol) and the reaction stirred for 15 minutes. Then acetoxyacetylchloride (74.5 g, 0.547 mol) was added at 0° C. and the reaction stirred for 4 hours at room temperature. The reaction mixture was diluted with DCM and washed with ice water followed by aqueous NaHCO₃. The organic layer was separated and washed with brine solution, dried over anhydrous Na₂SO₄ and concentrated under reduced pressure. The crude product was purified by triturating with diethyl ether (500 mL) to yield 2-{[4-cyano-3-(trifluoromethyl)phenyl]amino}-2-oxoethyl acetate (85.0 g).

MS ES-ve m/z 285 (M−H)

¹H NMR (400 MHz, Chloroform-d) δ ppm 2.26 (s, 3H) 4.74 (s, 2H) 7.8 (d, 1H) 8.0 (m, 2H), 8.33 (br.s., 1H)

Intermediate 22: {1-[4-cyano-3-(trifluoromethyl)phenyl]-1H-tetrazol-5-yl}methyl acetate

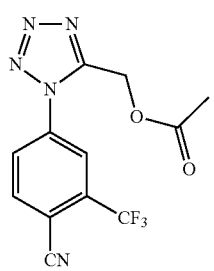 [SMILES: CC(=O)OCc1nnnn1-c1ccc(C#N)c(C(F)(F)F)c1]

To a solution of 2-{[4-cyano-3-(trifluoromethyl)phenyl]amino}-2-oxoethyl acetate (Intermediate 21, 65 g) in THF (300 mL) was added triphenylphosphine (161 g, 0.615 mol) and diisopropylazodicarboxylate (124 g, 0.615 mol) at 0° C. The reaction mixture was stirred for 30 minutes. Trimethylsilylazide (71.1 g, 0.615 mol) was added dropwise at room temperature and then heated to reflux for 4 hours. The reaction mixture was diluted with ethyl acetate and washed with ice-water. The organic layer was separated and washed with brine solution, dried over anhydrous Na₂SO₄ and concentrated under reduced pressure. The crude product was purified by column chromatography using an eluent of 20% ethyl acetate in petroleum ether to yield 1-[4-cyano-3-(trifluoromethyl)phenyl]-1H-tetrazol-5-yl}methyl acetate (45 g).

MS ES-ve m/z 310 (M−H)

Intermediate 23: 4-[5-(hydroxymethyl)-1H-tetrazol-1-yl]-2-(trifluoromethyl)benzonitrile

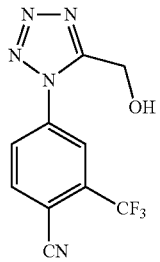

To a solution of 1-[4-cyano-3-(trifluoromethyl)phenyl]-1H-tetrazol-5-yl}methyl acetate (Intermediate 22, 45 g) in EtOH and water (2:1) was added LiOH (8.21 g, 0.342 mol) at 0° C. The reaction was stirred for 3 hours at room temperature. The solvent was removed under vacuum and the residue diluted with DCM, washed with ice-water, saturated aqueous NaHCO$_3$ and brine. The solution was dried over anhydrous Na$_2$SO$_4$ and the solvent removed under vacuum. The crude product was purified by triturating with ether (500 mL) to yield 4-[5-(hydroxymethyl)-1H-tetrazol-1-yl]-2-(trifluoromethyl)benzonitrile as a viscous oil (30 g).

MS ES-ve m/z 268 (M−H)

$^1$H NMR (400 MHz, Chloroform-d) δ ppm 3.1-3.2 (m, 1H) 5.0 (s, 2H) 8.1 (d, 1H) 8.2 (dd, 1H), 8.4 (s, 1H)

Intermediate 24: 4-[5-(chloromethyl)-1H-tetrazol-1-yl]-2-(trifluoromethyl)benzonitrile

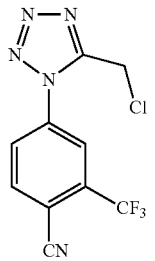 [SMILES: N#Cc1ccc(-n2nnnc2CCl)cc1C(F)(F)F]

To a solution of 4-[5-(hydroxymethyl)-1H-tetrazol-1-yl]-2-(trifluoromethyl)benzonitrile (Intermediate 23, 30.0 g) in toluene (500 mL) was added thionyl chloride (14.5 g, 0.122 mol) at room temperature. The reaction was heated to reflux and stirred for 2 hours. The reaction mixture was concentrated under vacuum and diluted with DCM. The resulting solution was washed with ice-water, followed by aqueous NaHCO$_3$. The organic was separated and washed with brine solution, dried over anhydrous Na$_2$SO$_4$ and concentrated under reduced pressure. The crude product was purified by triturating with ether (500 mL) and dried under vacuum to yield 4-[5-(chloromethyl)-1H-tetrazol-1-yl]-2-(trifluoromethyl)benzonitrile (23 g).

MS ES-ve m/z 286, 288 (M−H)

$^1$H NMR (400 MHz, Chloroform-d) δ ppm 5.25 (s, 2H) 8.32 (dd, 1H) 8.47 (d, 1H) 8.55 (d, 1H)

Intermediate 25: 1,1-dimethylethyl 4-({1-[4-cyano-3-(trifluoromethyl)phenyl]-1H-tetrazol-5-yl}methyl)-1-piperazinecarboxylate

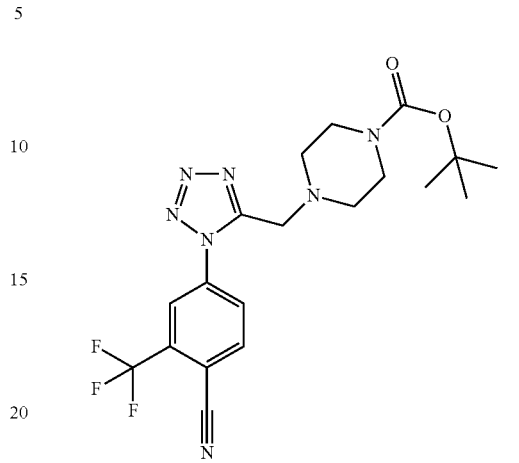

To a solution of 4-[5-(chloromethyl)-1H-tetrazol-1-yl]-2-(trifluoromethyl)benzonitrile (Intermediate 24, 575 mg, 2.00 mmol) in acetonitrile (10 mL) was added triethylamine (0.558 mL, 4.00 mmol) and 1,1-dimethylethyl 1-piperazinecarboxylate (410 mg, 2.20 mmol). The mixture was then heated to 120° C. for 20 min in a microwave reactor. The crude product was purified by silica chromatography (Biotage SP4, 40+S), eluting with 30% ethyl acetate in hexane (2 column volumes) then a gradient from 30-60% ethyl acetate in hexane (10 CV) then 60% ethyl acetate in hexane (2 column volumes). The relevant fractions were evaporated under vacuum to leave a white solid, 1,1-dimethylethyl 4-({1-[4-cyano-3-(trifluoromethyl)phenyl]-1H-tetrazol-5-yl}methyl)-1-piperazinecarboxylate (532 mg).

MS ES+ve m/z 338 (M+H-100)

$^1$H NMR (400 MHz, CHLOROFORM-d) δ ppm 1.47 (s, 9H), 2.57 (t, J=4.8 Hz, 4H), 3.44 (t, J=4.8 Hz, 4H), 3.85 (s, 2H), 8.12 (d, J=8.3 Hz, 1H), 8.29 (dd, J=8.3, 1.8 Hz, 1H), 8.79 (d, J=1.8 Hz, 1H).

Intermediate 26: 1,1-dimethylethyl 2-(hydroxymethyl)-5-({[(4-methylphenyl)sulfonyl]oxy}methyl)-1-pyrrolidinecarboxylate

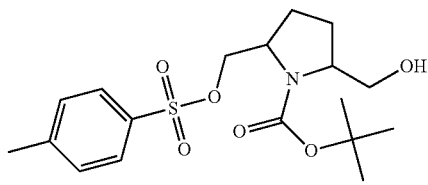 [SMILES: Cc1ccc(S(=O)(=O)OCC2CCC(CO)N2C(=O)OC(C)(C)C)cc1]

To a solution of 1,1-dimethylethyl 2,5-bis(hydroxymethyl)-1-pyrrolidinecarboxylate (commercially available, for example from J&W Pharmlab, 7.57 g, 32.7 mmol) in dichloromethane (200 mL) was added triethylamine (4.79 mL, 34.4 mmol), 4-dimethylaminopyridine (0.20 g, 1.64 mmol) and p-toluenesulfonyl chloride (6.55 g, 34.4 mmol). The reaction was stirred at room temperature for 18 hours. The reaction was diluted with DCM (200 mL) and the solution washed with water (200 mL). The organic layer was collected via a hydrophobic frit and the solvent removed under vacuum. The residue was purified by silica chromatography (Biotage SP4, eluting 30% EtOAc in iso-hexane (3 column volumes), a gradient from 30-50% (over 6 column volumes) then 50% EtOAc (3 column volumes)) to yield the title compound as a colourless gum (2.28 g).

$^1$H NMR (400 MHz, Chloroform-d) δ ppm 1.39 (s, 9H) 1.78-2.03 (m, 4H) 2.45 (s, 3H) 3.37-3.50 (m, 1H) 3.62-3.71 (m, 1H) 3.82-3.97 (m, 2H) 3.99-4.09 (m, 2H) 4.38-4.49 (m, 1H) 7.36 (d, J=8.1 Hz, 2H) 7.79 (d, J=8.3 Hz, 2H)

Intermediate 27: 3-oxa-8-azabicyclo[3.2.1]octane hydrochloride

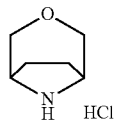

To a suspension of sodium hydride (60% dispersion in mineral oil) (0.284 g, 7.10 mmol) in N,N-Dimethylformamide (5 mL), cooled in an ice bath under argon, was added dropwise a solution of 1,1-dimethylethyl 2-(hydroxymethyl)-5-({[(4-methylphenyl)sulfonyl]oxy}methyl)-1-pyrrolidinecarboxylate (Intermediate 26, 2.28 g, 5.91 mmol) in N,N-Dimethylformamide (10 mL). The reaction was allowed to warm to room temperature and stirred for 5 hours. The reaction was cooled in an ice-water bath before the addition of sat. NH$_4$Cl (30 mL) and water (30 mL). The mixture was extracted with diethyl ether (3×60 mL). The ether layers were combined, washed with water:brine (1:1, 2×60 mL), passed through a hydrophobic frit and the solvent removed to yield a colourless gum, which was dried under vacuum for 18 hours to yield a white solid. The crude intermediate was dissolved in 1,4-Dioxane (5 mL) before the addition of HCl (4M in 1,4-dioxane) (14.8 mL, 59.1 mmol). The reaction was stirred at room temperature for 3 hours then the solvent was removed under vacuum to yield the title compound as a white solid (904 mg).

$^1$H NMR (400 MHz, Chloroform-d) δ ppm 2.11-2.23 (m, 2H) 2.23-2.35 (m, 2H) 3.67 (d, J=12.4 Hz, 2H) 3.94 (br. s., 2H) 4.24 (d, J=12.4 Hz, 2H) 9.84-10.29 (m, 2H)

Intermediate 28: 3-amino-5-(trifluoromethyl)benzonitrile

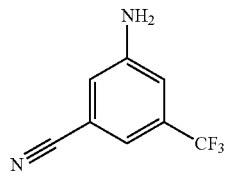 [SMILES: N#Cc1cc(N)cc(C(F)(F)F)c1]

A solution of 3-bromo-5-(trifluoromethyl)aniline (3.24 g, 13.5 mmol) in N,N-dimethylformamide (50 mL) was degassed by bubbling argon through the solution for 30 minutes. To the reaction was added zinc cyanide (0.872 g, 7.42 mmol) and tetrakis(triphenylphosphine)palladium(0) (0.624 g, 0.54 mmol). The reaction was heated to 80° C. and stirred for 20 hours. The solvent was removed from the reaction under vacuum and the residue purified by silica chromatography (Biotage SP4, eluting 15% EtOAc in iso-hexane (4 column volumes) then a gradient from 15-30% (over 6 column volumes)) to yield the title compound as a colourless oil (2.20 g).

$^1$H NMR (400 MHz, CHLOROFORM-d) δ ppm 3.98-4.29 (m, 2H) 7.04 (s, 1H) 7.07 (s, 1H) 7.24 (s, 1H)

Intermediate 29: 2-{[3-cyano-5-(trifluoromethyl)phenyl]amino}-2-oxoethyl acetate

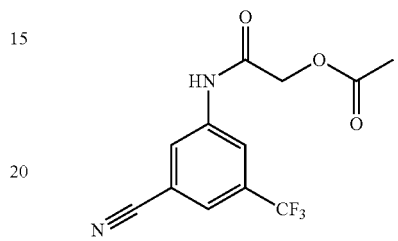

A solution of 3-amino-5-(trifluoromethyl)benzonitrile (Intermediate 28, 2.20 g, 11.82 mmol) and di-isopropylethylamine (2.27 mL, 13.0 mmol) in dichloromethane (40 mL) was cooled in an ice-water bath before the addition of 2-chloro-2-oxoethyl acetate (1.40 mL, 13.0 mmol) dropwise. The reaction was allowed to warm to room temperature and stirred for 4 hours. To the reaction was added 2-chloro-2-oxoethyl acetate (0.14 mL) and the reaction stirred at room temperature for a further 18 hours. The reaction was diluted with DCM (100 mL) and the solution washed with 2N HCl (75 mL) and NaHCO$_3$ (75 mL), collected via a hydrophobic frit and the solvent removed to yield the title compound as an orange oil (3.7 g)

MS ES+ve m/z 287 (M+H)

$^1$H NMR (400 MHz, CHLOROFORM-d) δ ppm 2.27 (s, 3H) 4.74 (s, 2H) 7.69 (s, 1H) 8.05 (s, 1H) 8.17 (br. s., 1H) 8.22 (s, 1H)

Intermediate 30: {1-[3-cyano-5-(trifluoromethyl)phenyl]-1H-tetrazol-5-yl}methyl acetate

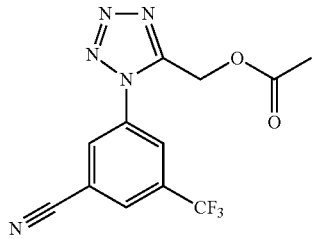 [SMILES: CC(=O)OCc1nnnn1-c1cc(C#N)cc(C(F)(F)F)c1]

To a solution of 2-{[3-cyano-5-(trifluoromethyl)phenyl]amino}-2-oxoethyl acetate (Intermediate 29, 3.38 g, 11.8 mmol) in tetrahydrofuran (100 mL) was added trimethylsilylazide (3.14 mL, 23.6 mmol), triphenylphosphine (6.20 g, 23.6 mmol) then di-isopropylazodicarboxylate (4.60 mL, 23.6 mmol). The reaction was warmed to 50° C. and stirred for 6 hours. The reaction was cooled and diluted with EtOAc (150 mL). The solution was washed with water (100 mL), passed through a hydrophobic frit and the solvent removed under vacuum. The residue was purified by silica chromatography (Biotage SP4, eluting 10% EtOAc in iso-hexane (4 column volumes) then a gradient from 10-35% EtOAc in iso-hexane (over 8 column volumes)) to yield the title compound as a yellow solid (3.33 g)

MS ES+ve m/z 312 (M+H)

Intermediate 31: 3-[5-(chloromethyl)-1H-tetrazol-1-yl]-5-(trifluoromethyl)benzamide

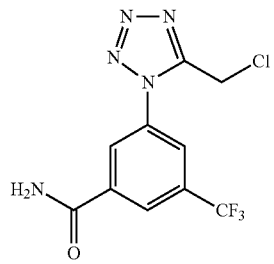 [SMILES: NC(=O)c1cc(-n2nnnc2CCl)cc(C(F)(F)F)c1]

A solution of {1-[3-cyano-5-(trifluoromethyl)phenyl]-1H-tetrazol-5-yl}methyl acetate (Intermediate 30, 3.33 g) in methanol (10.0 mL), tetrahydrofuran (20 mL) and water (10.0 mL) was cooled in an ice-water bath before the addition of lithium hydroxide monohydrate (0.449 g, 10.7 mmol). The reaction was stirred at 0-5° C. for 2 hours. The reaction was diluted with water (30 mL) and the organic solvent removed under vacuum. The suspension was extracted with ethyl acetate (3×50 mL). The organic layers were combined, dried and the solvent removed to yield a white solid. The solid was triturated with diethyl ether (2×25 mL), the solvent decanted and the residue dried under vacuum to yield the intermediate 3-[5-(hydroxymethyl)-1H-tetrazol-1-yl]-5-(trifluoromethyl)benzamide as a white solid (1.37 g).

To a suspension of 3-[5-(hydroxymethyl)-1H-tetrazol-1-yl]-5-(trifluoromethyl)benzamide (500 mg, 1.741 mmol) in toluene (5 mL) was added thionyl chloride (0.140 mL, 1.92 mmol) and the reaction heated to reflux for 4 hours. The reaction was allowed to cool and the solvent removed under vacuum. The residue was partitioned between DCM (20 mL) and water (10 mL). The organic layer collected via a hydrophobic frit and the solvent removed under vacuum. The residue was purified by silica chromatography (Biotage SP4, eluting 10% EtOAc in iso-hexane (5 column volumes) then a gradient from 10-100% EtOAc in iso-hexane (over 10 column volumes)) to yield the title compound as a pale yellow gum (360 mg).

MS ES+ve m/z 306 (M+H)
$^1$H NMR (400 MHz, DMSO-$d_6$) δ ppm 5.22 (s, 2H) 7.87 (br. s., 1H) 8.39 (s, 1H) 8.41 (br. s., 1H) 8.47-8.52 (m, 2H)

Intermediate 32: 3-{5-[(1S,4S)-2-oxa-5-azabicyclo[2.2.1]hept-5-ylmethyl]-1H-tetrazol-1-yl}-5-(trifluoromethyl)benzamide

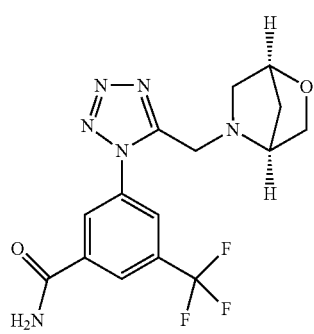 [SMILES: NC(=O)c1cc(-n2nnnc2CN2C[C@@H]3C[C@H]2CO3)cc(C(F)(F)F)c1]

To a solution of 3-[5-(chloromethyl)-1H-tetrazol-1-yl]-5-(trifluoromethyl)benzamide (Intermediate 31, 300 mg, 0.982 mmol) in acetonitrile (0.5 mL) was added (1S,4S)-2-oxa-5-azabicyclo[2.2.1]heptane hydrochloride (160 mg, 1.18 mmol) and di-idopropylethylamine (0.377 mL, 2.16 mmol). The reaction was heated to 140° C. for 20 minutes in a microwave reactor.

The reaction was cooled and the solvent removed under vacuum. The reaction was partitioned between water (5 mL) and ethyl acetate (10 mL). The organic layer was collected, passed through a hydrophobic frit and the solvent removed under vacuum to yield the title compound as a yellow gum 356 mg.

MS ES+ve m/z 369 (M+H)
$^1$H NMR (400 MHz, DMSO-$d_6$) δ ppm 1.52-1.59 (m, 1H) 1.59-1.66 (m, 1H) 2.46 (d, J=9.9 Hz, 1H) 2.67 (dd, J=10.0, 1.6 Hz, 1H) 3.39 (s, 1H) 3.48 (dd, J=7.7, 1.8 Hz, 1H) 3.70 (d, J=7.7 Hz, 1H) 4.10 (d, J=14.5 Hz, 1H) 4.17 (d, J=14.5 Hz, 1H) 4.33 (s, 1H) 7.84 (s, 1H) 8.41 (br. s., 1H) 8.45 (s, 1H) 8.52 (s, 1H) 8.59 (s, 1H)

Intermediate 33: (3R)-3-methyl-1-(methylsulfonyl)piperazine

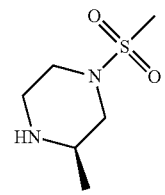

To a solution of (2R)-2-methylpiperazine (1.00 g, 9.98 mmol) in NaOH (2 M aqueous, 10.5 ml, 21.0 mmol) and THF (15 ml) at 0° C. was added a solution of mesyl chloride (0.817 ml, 10.5 mmol) in THF (5 ml) over 30 seconds. The clear solution was stirred at 0° C. for 2 h. The reaction was poured into 2M aqueous HCl (20 ml), then the mixture washed with EtOAc (2×25 ml). The aqueous was adjusted to pH 12 with solid NaOH (~1.5 g), then extracted with DCM (2×25 ml). The combined organics were passed through a phase separator and concentrated under vacuum to leave a white solid, (3R)-3-methyl-1-(methylsulfonyl)piperazine (352 mg).
$^1$H NMR (400 MHz, CHLOROFORM-d) δ ppm 1.08 (d, 3H), 2.30 (dd, J=11.2, 10.3 Hz, 1H), 2.68 (td, J=11.2, 3.3 Hz, 1H), 2.76 (s, 3H), 2.84-2.98 (m, 2H), 3.06 (dt, J=12.1, 2.4 Hz, 1H), 3.58-3.68 (m, 2H).

Intermediate 34: (2R)-2-methyl-1-(methylsulfonyl)piperazine hydrochloride

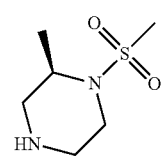

To a solution of 1,1-dimethylethyl (3R)-3-methyl-1-piperazinecarboxylate (commercially available, for example from Sigma Aldrich, St Louis, USA, 1.18 g, 4.98 mmol) in NaOH (2 M aqueous) (6.23 ml, 12.5 mmol) and THF (10 ml) at rt was added mesyl chloride (0.408 ml, 5.23 mmol) over 30 seconds. The solution was stirred vigorously at rt for 2 hours. Additional mesyl chloride (0.408 ml, 5.23 mmol) was added and the reaction was stirred vigorously at rt for 2 hours. Additional mesyl chloride (0.408 ml, 5.23 mmol) was added and the solution stirred vigorously at rt for 18 hours. The reaction was diluted with ethyl acetate (50 ml), then washed with 2M aqueous HCl (2×25 ml), brine (25 ml), dried (MgSO$_4$), filtered and concentrated under vacuum to leave a clear oil (900 mg) that became a crystalline white solid on standing overnight. This was redissolved in DCM (5.0 ml), then TFA (1.24 ml, 16.2 mmol) was added and the solution heated at reflux for 2 hours. The solution was cooled to rt, and concentrated under vacuum to leave a pale orange paste. This was re-dissolved in methanol (10 ml) and applied to an SCX-2 cartridge (25 g), washing with MeOH (50 ml). The product was eluted with 2M NH3 in MeOH (50 ml) and the solvent removed under vacuum to leave a viscous clear oil (361 mg). This was re-dissolved in methanol (10 ml) and aqueous HCl (2 M, 2.0 ml, 4.00 mmol) added. Concentration under vacuum, followed by azeotroping with toluene (2×25 ml) left a white solid, (2R)-2-methyl-1-(methylsulfonyl)piperazine hydrochloride (412 mg).

$^1$H NMR (400 MHz, DMSO-d$_5$) δ ppm 1.35 (d, J=7.0 Hz, 3H), 2.91 (m, 1H), 3.04 (s, 3H), 3.06-3.21 (m, 3H), 3.33 (ddd, J=14.5, 12.1, 2.9 Hz, 1H), 3.61 (d, J=14.5 Hz, 1H), 4.13 (m, 1H), 9.26 (br s, 1H), 9.83 (br s, 1H).

Intermediate 35: 1,1-dimethylethyl 8-({1-[4-cyano-3-(trifluoromethyl)phenyl]-1H-tetrazol-5-yl}methyl)-2,8-diazaspiro[4.5]decane-2-carboxylate

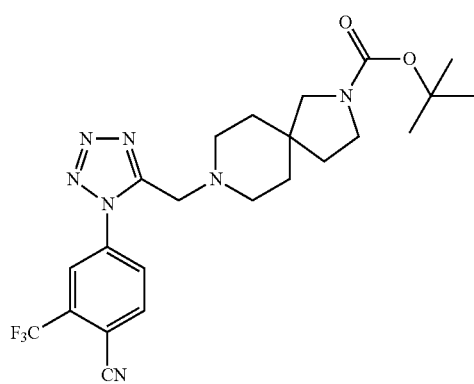 [SMILES: CC(C)(C)OC(=O)N1CCC2(CCN(Cc3nnnn3-c3ccc(C#N)c(C(F)(F)F)c3)CC2)C1]

To a mixture of 4-[5-(chloromethyl)-1H-tetrazol-1-yl]-2-(trifluoromethyl)benzonitrile (Intermediate 34, 300 mg, 1.04 mmol) and 1,1-dimethylethyl 2,8-diazaspiro[4.5]decane-2-carboxylate (commercially available, for example from J&W Pharmlab, Levittown, USA, 301 mg, 1.25 mmol) in acetonitrile (5 mL) was added triethylamine (0.173 mL, 1.25 mmol). The reaction was heated at 120° C. for 20 min in a microwave reactor. Solvent was removed under vacuum to afford 680 mg of the title compound as a pale yellow solid.

MS ES+ve m/z 492 (M+H)

Intermediate 36: 3,5-Dimethyl-1-(methylsulfonyl)piperazine

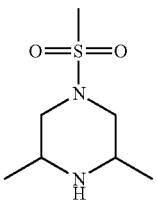

A solution of methanesulfonyl chloride (1.42 mL, 18.4 mmol) in DCM (10 mL) was added dropwise to a solution of 2,6-dimethylpiperazine (2 g, 17.5 mmol) and triethylamine (2.56 mL, 18.4 mmol) in DCM (10 mL) under nitrogen. The mixture was stirred for 30 min. The solvent was removed and the residue was applied to a 5 g aminopropyl SPE cartridge to give the product as a yellow solid (2.3 g), ~10:1 mixture of cis and trans isomers by NMR.

$^1$H NMR (400 MHz, MeOH-d) δ ppm 1.24 (d, J=6 Hz, 6H$_{maj}$), 1.34 (d, J=6 Hz, 6H$_{min}$), 2.56 (t, J=12 Hz, 2H$_{maj}$), 2.90 (s, 3H$_{maj}$), 2.91 (S, 3H$_{min}$), 2.94-2.97 (m, 2H$_{min}$), 3.13-3.23 (m, 2H$_{maj}$), 3.39-3.49 (m, 2H$_{min}$), 3.58-3.64 (m, 2H$_{min}$), 3.75 (dd, J=12, 2.5 Hz, 2H$_{maj}$).

Intermediate 37: 5-Amino-2-(trifluoromethyl)benzonitrile

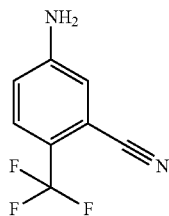

Ammonium hydroxide solution (50 mL) was added to a stirred solution of 5-fluoro-2-(trifluoromethyl)benzonitrile (commercially available, for example from Alfa Aesar, Ward Hill, Mass., USA, 2.0 g, 10.6 mmol) in 1,4-dioxane (10 mL) and the reaction mixture was heated to 130° C. for 20 h under 200 psi pressure in a steel bomb. The reaction mixture was evaporated to dryness, and the residue was diluted with DCM and washed with water. The organic layer was dried over anhydrous Na$_2$SO$_4$ and concentrated under reduced pressure to afford the crude product. This was purified by column chromatography (100-200 mesh silica gel), eluting with 20%-40% EtOAc/petroleum ether, to give the title compound (1.2 g).

MS ES+ve m/z 185 (M–H).

$^1$H NMR (400 MHz, Chloroform-d) δ ppm 4.02-4.30 (br s, 2H), 6.85 (dd, 1H), 7.00 (d, 1H), 7.50 (d, 1H).

Intermediate 38: 2-{[3-Cyano-4-(trifluoromethyl)phenyl]amino}-2-oxoethyl acetate

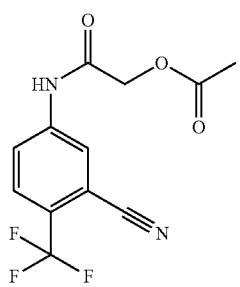 [SMILES: CC(=O)OCC(=O)Nc1ccc(C(F)(F)F)c(C#N)c1]

Triethylamine (1.09 g, 10.8 mmol) was added to a stirred solution of 5-amino-2-(trifluoromethyl)benzonitrile (Intermediate 37, 1.0 g, 5.37 mmol) in DCM (40 mL), at 0° C., and the mixture was stirred for 15 min. Chloro-2-oxoethyl acetate (1.10 g, 8.06 mmol) was added at 0° C. and the mixture was stirred for 4 h at room temperature. The reaction mixture was diluted with DCM and washed with ice water, and saturated brine solution. The organic layer was dried over anhydrous $Na_2SO_4$, and concentrated under reduced pressure to afford the crude compound. This was purified by column chromatography (100-200 mesh silica gel), eluting with 20%-40% EtOAc/pet.ether to give the title compound (1.1 g).

MS ES+ve m/z 285 (M−H).

$^1$H NMR (400 MHz, Chloroform-d) δ ppm 2.26 (s, 3H), 4.76 (s, 2H), 7.72-7.82 (m, 1H), 7.90-8.00 (m, 1H), 8.08-8.18 (m, 1H).

Intermediate 39: {1-[3-Cyano-4-(trifluoromethyl)phenyl]-1H-tetrazol-5-yl}methyl acetate

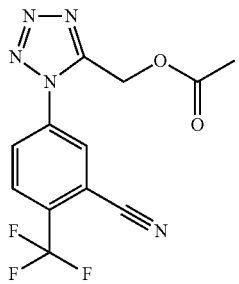 [SMILES: CC(=O)OCc1nnnn1-c1ccc(C(F)(F)F)c(C#N)c1]

Triphenylphosphine (2.29 g, 8.73 mmol) and diisopropylazodicorboxylate (1.76 g, 8.70 mmol) were added to a solution of 2-{[3-cyano-4-(trifluoromethyl)phenyl]amino}-2-oxoethyl acetate (Intermediate 38, 1.0 g, 3.49 mmol) in THF (20 mL), at 0° C. The reaction mixture was stirred for 30 min at 0° C. and trimethylsilyl azide (1.01 g, 8.77 mmol) was added dropwise. The reaction mixture was allowed to warm to room temperature, and then heated to reflux for 4 h. The reaction mixture was diluted with EtOAc and washed with ice water, followed by saturated brine solution. The organic layer was dried over anhydrous $Na_2SO_4$, and concentrated under reduced pressure to afford the crude compound. This was purified by column chromatography (100-200 mesh silica gel), eluting with 10%-50% EtOAc/pet.ether, to give the title compound (1.5 g, impure).

$^1$H NMR (400 MHz, Chloroform-d) δ ppm 2.16 (s, 3H), 5.40 (s, 2H), 8.00-8.10 (m, 1H), 8.10-8.20 (m, 2H).

Intermediate 40: 5-[5-(Hydroxymethyl)-1H-tetrazol-1-yl]-2-(trifluoromethyl)benzonitrile

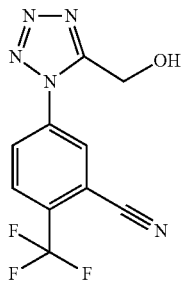

Lithium hydroxide monohydrate (1.35 g, 32.2 mmol) was added to a solution of {1-[3-cyano-4-(trifluoromethyl)phe-nyl]-1H-tetrazol-5-yl}methyl acetate (Intermediate 39, 5.0 g, 16.1 mmol) in a mixture of ethanol and water (2:1) at 0° C. The reaction mixture was stirred for 6 h at room temperature. The reaction mixture was diluted with EtOAc and washed with ice-water. The organic layer was dried over anhydrous $Na_2SO_4$ and concentrated under reduced pressure to afford the crude compound. This was purified by column chromatography (100-200 mesh silica gel), eluting with 20%-60% EtOAc/pet.ether to give the title compound (1.2 g).

MS ES+ve m/z 268 (M−H).

$^1$H NMR (400 MHz, DMSO-d6) δ ppm 4.92 (s, 2H), 6.05 (s, 3H), 8.3-=8.40 (m, 2H), 8.65 (s, 1H).

Intermediate 41: 5-[5-(Chloromethyl)-1H-tetrazol-1-yl]-2-(trifluoromethyl)benzonitrile

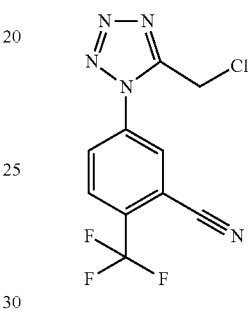

Thionyl chloride (4.25 g, 3.57 mmol) was added dropwise to a solution of 5-[5-(hydroxymethyl)-1H-tetrazol-1-yl]-2-(trifluoromethyl)benzonitrile (Intermediate 40, 8.0 g, 29.7 mmol) in toluene (200 mL) at 0° C. The reaction mixture was allowed to warm to room temperature and then heated to reflux for 4 hr. The mixture was diluted with EtOAc and washed with ice-water, and saturated $NaHCO_3$, dried over anhydrous $Na_2SO_4$, and concentrated under reduced pressure to afford the crude product. This was purified by column chromatography (100-200 mesh silica gel), eluting with 20%-40% ethyl acetate/pet ether to give the title compound (5.35 g) as a white powder.

MS ES+ve m/z 286 (M−H).

$^1$H NMR (400 MHz, Chloroform-d) δ ppm 4.90 (s, 2H), 8.05-8.15 (m, 2H), 8.19 (s, 1H).

Intermediate 42: 2-Oxo-2-{[4-(pentafluoro-λ$^6$-sulfanyl)phenyl]amino}ethyl acetate

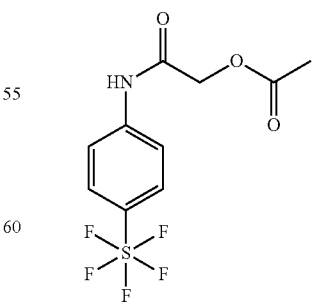

Triethylamine (13.9 g, 137 mmol) was added to a stirred solution of 4-(pentafluoro-λ$^6$-sulfanyl)aniline (Commercially available, for example from Apollo Scientific, Stockport, UK, 10.0 g, 45.6 mmol) in DCM (100 mL) at 0° C. and the mixture was stirred for 15 mins. 2-Chloro-2-oxoethyl acetate (7.47 g, 54.7 mmol) was added at 0° C., and the temperature was raised to room temperature with stirring continued for 4 hr. The reaction mixture was diluted with DCM and washed with ice water, saturated aq NaHCO$_3$ solution and brine solution, dried over anhydrous Na$_2$SO$_4$, and concentrated under reduced pressure to give the crude product. This was purified by recrystallisation from ether (500 mL) to give the title compound (8.64 g).

$^1$H NMR (400 MHz, DMSO-d6) δ ppm 2.16 (s, 3H), 4.72 (s, 2H), 7.79 (d, 2H), 7.91 (d, 2H), 10.58 (s, 1H).

Intermediate 43: {1-[4-(Pentafluoro-λ$^6$-sulfanyl)phenyl]-1H-tetrazol-5-yl}methyl acetate

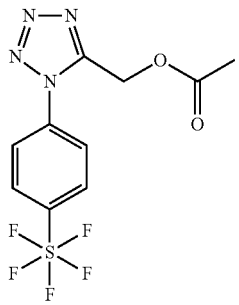 [SMILES: CC(=O)OCc1nnnn1-c1ccc(S(F)(F)(F)(F)F)cc1]

Triphenylphosphine (16.2 g, 61.9 mmol) and diisopropylazodicorboxylate (12.5 g, 61.8 mmol) were added to a solution of 2-oxo-2-{[4-(pentafluoro-λ$^6$-sulfanyl)phenyl]amino}ethyl acetate (Intermediate 42, 8.50 g, 26.2 mmol) in THF (100 mL) at 0° C. and the mixture was stirred for 30 min. Trimethylsilyl azide (7.11 g, 61.7 mmol) was added dropwise at room temperature and the mixture was heated to reflux for 4 hr. The reaction mixture was diluted with EtOAc and washed with ice-water and brine solution, dried over anhydrous Na$_2$SO$_4$, and concentrated under reduced pressure to give the crude product (5.32 g). This was used for the next step without further purification.

Intermediate 44: {1-[4-(Pentafluoro-λ$^6$-sulfanyl)phenyl]-1H-tetrazol-5-yl}methanol

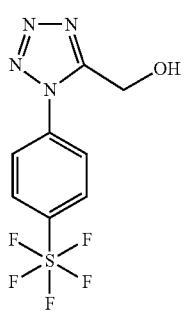

Lithium hydroxide (553 mg, 22.2 mmol) was added to a solution of {1-[4-(pentafluoro-λ$^6$-sulfanyl)phenyl]-1H-tetrazol-5-yl}methyl acetate (Intermediate 43, 5.30 g, 15.3 mmol) in ethanol:water (2:1), at 0° C. The reaction mixture was stirred for 3 hr at room temperature. The solvent was removed by under reduced pressure and the residue was diluted with DCM, washed with ice-water, saturated aq NaHCO$_3$ and brine solution, dried over anhydrous Na$_2$SO$_4$, and concentrated under reduced pressure to give the crude product. This was purified by column chromatography (100-200 mesh silica gel), eluting with 30%-40% EtOAc/pet-ether gave the title compound (3.98 g).

$^1$H NMR (400 MHz, DMSO-d6) δ ppm 4.89 (s, 2H), 6.02 (t, 1H), 8.11 (d, 2H), 8.25 (d, 2H).

Intermediate 45: 5-(Chloromethyl)-1-[4-(pentafluoro-λ$^6$-sulfanyl)phenyl]-1H-tetrazole

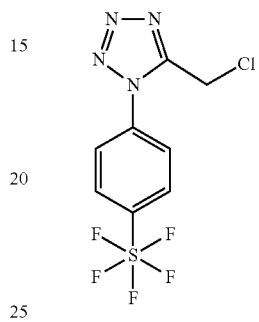

Thionyl chloride (1.72 g, 14.4 mmol) was added to a stirred solution of {1-[4-(pentafluoro-λ$^6$-sulfanyl)phenyl]-1H-tetrazol-5-yl}methanol (Intermediate 44, 3.50 g, 11.6 mmol) in toluene (40 mL), SOCl$_2$ at room temperature. The reaction mixture was stirred for 4 hr at reflux. The reaction mixture was concentrated under vacuum. The residue was diluted with DCM and washed with ice-water, saturated aq NaHCO$_3$ and brine solution, dried over anhydrous Na$_2$SO$_4$, and concentrated under reduced pressure to give the crude compound. This was purified by column chromatography (100-200 mesh silica gel), eluted with 20%-30% EtOAc/pet-ether to give the title compound as a brown gum (3.50 g).

MS ES+ve m/z 319 (M−H).

$^1$H NMR (400 MHz DMSO-d6) δ ppm 5.22 (s, 2H), 8.02 (d, J=9 Hz, 2H), 8.27 (d, J=9 Hz, 2H).

Intermediate 46: 2-{[4-cyano-2-methyl-3-(trifluoromethyl)phenyl]amino}-2-oxoethyl acetate

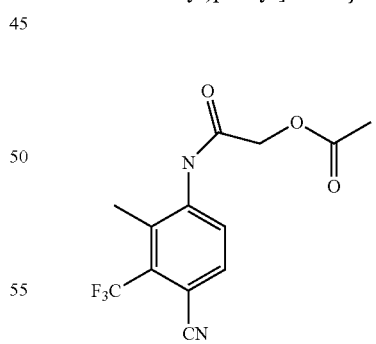

To a solution of 4-amino-3-methyl-2-(trifluoromethyl) benzonitrile (commercially available, for example from Sunshine Chemlab, Downington, Pa., USA, 500 mg, 2.50 mmol) and triethylamine (0.383 mL, 2.75 mmol) in dichloromethane (10 mL) was added 2-chloro-2-oxoethyl acetate (0.269 mL, 2.50 mmol) dropwise. The reaction mixture was stirred at room temperature for 3 hours. The reaction mixture was diluted with DCM (100 ml) and water (50 ml) and aqueous was extracted with DCM (100 ml). The organics were combined, passed through a phase separator and concentrated to afford 710 mg of the title compound as a pale yellow powder.

MS ES-ve m/z 299 (M−H)

$^1$H NMR (400 MHz, METHANOL-$d_4$) δ ppm 2.18 (s, 3H) 2.41 (q, J=2.12 Hz, 3H) 4.78 (s, 2H) 7.81 (d, J=8.33 Hz, 1H) 7.92 (d, J=8.33 Hz, 1H)

Intermediate 47: {1-[4-cyano-2-methyl-3-(trifluoromethyl)phenyl]-1H-tetrazol-5-yl}methyl acetate

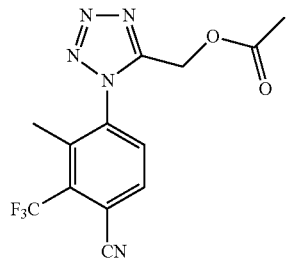 [SMILES: CC(=O)OCc1nnnn1-c1ccc(C#N)c(C(F)(F)F)c1C]

To a solution of 2-{[4-cyano-2-methyl-3-(trifluoromethyl)phenyl]amino}-2-oxoethyl acetate (Intermediate 46, 710 mg, 2.37 mmol) in tetrahydrofuran (20 mL) was added triphenylphosphine (1.24 g, 4.73 mmol), DIAD (0.920 mL, 4.73 mmol) and trimethylsilylazide (0.628 mL, 4.73 mmol). The reaction was stirred at room temperature for 18 hours. Solvent was removed under vacuum and residue was purified by silica chromatography (Biotage SP4, eluting 0% ethyl acetate in iso-hexane (2 column volumes), then a gradient from 0-50% ethyl acetate in iso-hexane (over 10 column volumes)). Pure fractions were combined and the solvent removed to yield the titled compound as a white solid (330 mg).

MS ES+ve m/z 326 (M+H)

$^1$H NMR (400 MHz, METHANOL-$d_4$) δ ppm 1.94 (s, 3H) 2.19 (q, J=2.05 Hz, 3H) 5.35 (s, 2H) 7.97 (d, J=8.33 Hz, 1H) 8.12 (d, J=8.11 Hz, 1H)

Intermediate 48: 4-[5-(hydroxymethyl)-1H-tetrazol-1-yl]-3-methyl-2-(trifluoromethyl)benzonitrile

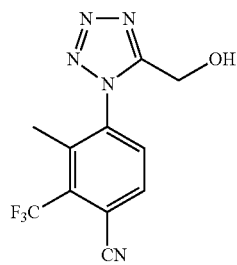 [SMILES: Cc1c(-n2nnnc2CO)ccc(C#N)c1C(F)(F)F]

To a solution of {1-[4-cyano-2-methyl-3-(trifluoromethyl)phenyl]-1H-tetrazol-5-yl}methyl acetate (Intermediate 47, 330 mg, 1.02 mmol) in water (2 mL) and tetrahydrofuran (4 mL), cooled in an ice bath, was added lithium hydroxide monohydrate (42.6 mg, 1.02 mmol). The reaction was stirred at room temperature for 1 hour and 30 min. The organic solvent was removed from the reaction under vacuum and the residual mixture diluted with water (30 mL) and extracted with DCM (2*50 ml). The organic extracts were combined, dried (hydrophobic frit) and the solvent removed to yield the titled compound as a white solid.

MS ES+ve m/z 284 (M+H)

$^1$H NMR (400 MHz, METHANOL-$d_4$) δ ppm 2.19 (q, J=2.05 Hz, 3H) 4.84 (s, 2H) 7.94 (d, J=8.11 Hz, 1H) 8.09 (d, J=8.11 Hz, 1H)

Intermediate 49: 4-[5-(chloromethyl)-1H-tetrazol-1-yl]-3-methyl-2-(trifluoromethyl)benzonitrile

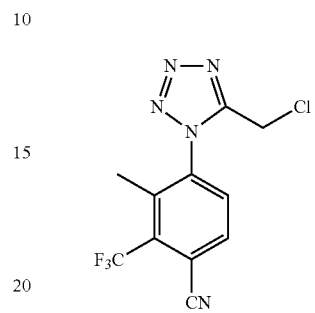

To a solution of 4-[5-(hydroxymethyl)-1H-tetrazol-1-yl]-3-methyl-2-(trifluoromethyl)benzonitrile (Intermediate 48, 294 mg, 1.04 mmol) in dichloromethane (5 mL) and N,N-Dimethylformamide (0.5 mL), cooled in an ice bath under argon, was added dropwise thionyl chloride (0.080 mL, 1.09 mmol). The reaction was stirred at 25° C. for two hours. To the reaction was added water (50 mL) and DCM (100 mL) and the reaction partitioned through a hydrophobic frit. The organic layer was evaporated to dryness under vacuum to afford 240 mg of the title compound as a colourless oil.

MS ES-ve m/z 300 (M−H)

$^1$H NMR (400 MHz, METHANOL-$d_4$) δ ppm 2.20 (q, J=2.12 Hz, 3H) 4.95 (s, 2H) 8.01 (d, J=8.11 Hz, 1H) 8.14 (d, J=8.33 Hz, 1H)

Intermediate 50: 1,1-Dimethylethyl {4-bromo-3-[(trifluoromethyl)oxy]phenyl}carbamate

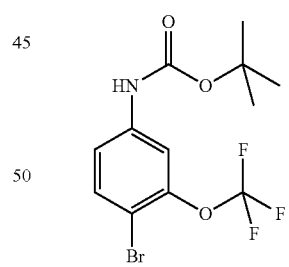

To a stirred solution of 4-bromo-3-[(trifluoromethyl)oxy]aniline (Commercially available, for example from Atomole Scientific, Wuhan, Hubei, China, 2.0 g, 7.8 mmol) in t-butanol at room temperature was added slowly 10% NaOH solution (3.10 g, 7.5 mmol), followed by di-tert-butyl dicarbonate (1.70 g, 7.8 mmol) and the mixture was stirred for 4 days. The reaction was quenched with ice-water and extracted with ethyl acetate (2×50 mL). The combined organic layers were dried over anhydrous $Na_2SO_4$ and concentrated under reduced pressure to afford the crude product. This was washed with pentane to afford the title compound (1.50 g).

MS ES+ve m/z 354 (M−H).

¹H NMR (400 MHz, Chloroform-d) δ ppm 1.50 (s, 9H), 6.58 (br s, 1H), 7.10-7.20 (m, 1H), 7.45-7.55 (m, 2H).

Intermediate 51:
4-Amino-2-[(trifluoromethyl)oxy]benzonitrile

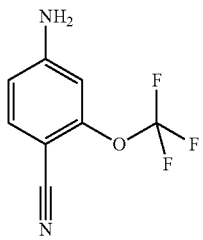

1,1-Dimethylethyl {4-bromo-3-[(trifluoromethyl)oxy]phenyl}carbamate (Intermediate 50, 1.0 g, 2.8 mmol) was dissolved in dry DMF (25 mL). To this solution was added CuCN (1.0 g, 11.1 mmol), and the reaction mixture was heated to reflux for 5 h. A second portion of CuCN (500 mg, 5.6 mmol) was added and heating at reflux was continued for 10 h. The reaction mixture was cooled to room temperature, and FeCl₃ was added. This was followed by 1N HCl at 0° C. and the mixture was stirred for 2 hr at room temperature. The reaction mixture was diluted with water and extracted with ethyl acetate (2×50 mL). The combined organic layers were dried over anhydrous Na₂SO₄ and concentrated under reduced pressure to afford the crude product. This was purified by column chromatography (60-120 silica gel), eluting with 30% ethyl acetate/pet ether to give the title compound (260 mg).

MS ES+ve m/z 202 (M–H).
¹H NMR (400 MHz, DMSO-d6) δ ppm 6.5-6.7 (m, 4H), 7.42 (s, 2H).

Intermediate 52: 2-({4-Cyano-3-[(trifluoromethyl)oxy]phenyl}amino)-2-oxoethyl acetate

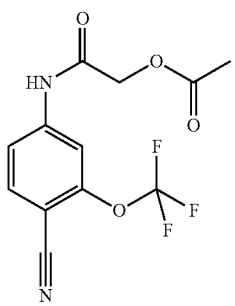 [SMILES: CC(=O)OCC(=O)Nc1ccc(C#N)c(OC(F)(F)F)c1]

Triethylamine (6.5 g, 64.2 mmol) was added to a stirred solution of 4-amino-2-[(trifluoromethyl)oxy]benzonitrile (Intermediate 51, 6.5 g, 32.2 mmol) in DCM (100 mL) at 0° C. and the mixture was stirred for 15 min. Chloro-2-oxoethyl acetate (5.2 g, 38.1 mmol) was added at 0° C. and stirring was continued for 4 hr at room temperature. The reaction mixture was diluted with DCM and washed with ice-water, saturated aq. NaHCO₃ solution and brine solution, dried over anhydrous Na₂SO₄ and concentrated under reduced pressure to afford the crude product. This was purified by column chromatography (100-200 mesh silica gel), eluting with 30% EtOAc/pet ether to give the title compound (8.10 g).

MS ES+ve m/z 301 (M–H).
¹H NMR (400 MHz, DMSO-d6) δ ppm 2.12 (s, 3H), 4.78 (s, 2H), 7.60-7.65 (m, 1H), 7.95-8.10 (m, 2H), 10.84 (s, 1H).

Intermediate 53: (1-{4-Cyano-3-[(trifluoromethyl)oxy]phenyl}-1H-tetrazol-5-yl)methyl acetate

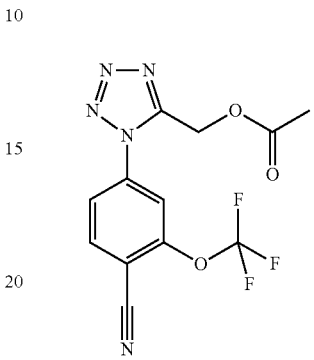

Triphenylphosphine (17.29 g, 65.7 mmol) and diisopropylazodicorboxylate (13.3 g, 65.7 mmol) were added to a solution of 2-({4-cyano-3-[(trifluoromethyl)oxy]phenyl}amino)-2-oxoethyl acetate (Intermediate 52, 8.0 g, 26.5 mmol) in THF (160 mL) at 0° C. and the mixture was stirred for 30 min. Trimethylsilyl azide (7.60 g, 66.0 mmol) was added dropwise at room temperature and the mixture was heated to reflux for 4 hr. THF was removed under reduced pressure and the residue was diluted with EtOAc and washed with ice-cooled water. The extracted organic layer was washed with brine solution, dried over anhydrous Na₂SO₄ and concentrated under reduced pressure to afford the crude product. This was purified by column chromatography (100-200 mesh silica gel), eluting with 20% EtOAc/pet ether to give the title compound (7.0 g).

¹H NMR (400 MHz, Chloroform-d) δ ppm 2.12 (s, 3H), 5.42 (s, 2H), 7.75-7.82 (m, 2H), 7.99-8.05 (m, 1H).

Intermediate 54: 4-[5-(Hydroxymethyl)-1H-tetrazol-1-yl]-2-[(trifluoromethyl)oxy]benzonitrile

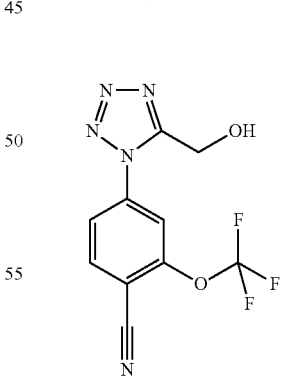

(1-{4-Cyano-3-[(trifluoromethyl)oxy]phenyl}-1H-tetrazol-5-yl)methyl acetate (Intermediate 53, 7.0 g, 21.4 mmol) was dissolved in MeOH:THF:H₂O (1:2:1) and the solution was cooled to 0° C. Lithium hydroxide (770 mg, 32.2 mmol) was added at 0° C. The reaction was slowly allowed to reach room temperature and stirred for 3 hr. The solvent was removed under reduced pressure. The residue was diluted with DCM, and washed with ice-cooled water, saturated aq. NaHCO₃ and brine solution, dried over anhydrous Na₂SO₄ and concentrated under reduced pressure to give the crude product. This was purified by column chromatography (100-200 mesh silica gel), eluting with 30% EtOAc/pet ether to give the title compound (3.50 g).

¹H NMR (400 MHz, DMSO-d6) δ ppm 4.85 (s, 2H), 6.10 (t, 1H), 7.02 (d, 1H), 8.20 (s, 1H), 8.40 (d, 1H).

Intermediate 55: 4-[5-(Chloromethyl)-1H-tetrazol-1-yl]-2-[(trifluoromethyl)oxy]benzonitrile

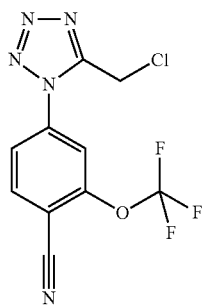

Thionyl chloride (2.21 g, 18.6 mmol) was added to a stirred solution of 4-[5-(hydroxymethyl)-1H-tetrazol-1-yl]-2-[(trifluoromethyl)oxy]benzonitrile (Intermediate 54, 3.50 g, 12.3 mmol) in toluene (50 mL) at room temperature, and the reaction mixture was heated to reflux for 4 h. The reaction mixture was concentrated under vacuum. The residue was diluted with DCM and washed with ice-cooled water, saturated aq NaHCO₃ and brine solution, dried over anhydrous Na₂SO₄, and concentrated under reduced pressure to give the crude product. This was purified by column chromatography (60-120 mesh silica gel), eluting with 20% EtOAc/pet.ether to give the title compound as an off-white powder (2.85 g).

MS ES+ve m/z 302 (M−H).
¹H NMR (400 MHz, Chloroform-d) δ ppm 4.87 (s, 2H), 7.76-7.83 (m, 2H), 8.03 (d, J=8 Hz, 1H).

Intermediate 56: 2-Oxo-2-{[5-(trifluoromethyl)-2-pyridinyl]amino}ethyl acetate

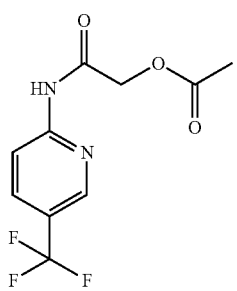 [SMILES: CC(=O)OCC(=O)Nc1ccc(C(F)(F)F)cn1]

Triethylamine (9.30 g, 91.9 mmol) was added at 0° C. to a stirred solution of 2-amino-5-trifluoromethylpyridine (5.0 g, 30.8 mmol) in DCM, and stirring was continued for 15 min. 2-Chloro-2-oxoethyl acetate (5.03 g, 36.8 mmol) was added at 0° C., and the temperature was raised to room temperature and the mixture was stirred for 4 hrs. The reaction mixture was diluted with DCM and washed with ice-water, aq. NaHCO₃ solution and saturated brine solution, dried over anhydrous Na₂SO₄, and concentrated under reduced pressure to afford the crude compound. This was purified by column chromatography (100-200 silica gel), eluting with 0-20% EtOAc/pet ether to give the title compound (3.30 g) as a pale brown solid.

MS ES+ve m/z 263 (M+H).
¹H NMR (400 MHz, DMSO-d6) δ ppm 2.07 (s, 3H), 4.80 (s, 2H), 7.80 (d, 1H), 8.55 (d, 1H), 9.06 (s, 1H).

Intermediate 57: {1-[5-(Trifluoromethyl)-2-pyridinyl]-1H-tetrazol-5-yl}methyl acetate

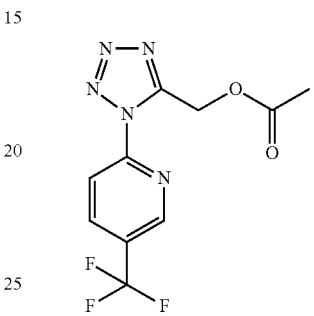

To a solution of 2-oxo-2-{[5-(trifluoromethyl)-2-pyridinyl]amino}ethyl acetate (Intermediate 56, 3.30 g, 12.6 mmol) in THF at 0° C. were added triphenylphosphine (8.24 g, 31.4 mmol) and diisopropyl azodicorboxylate (6.30 g, 31.2 mmol). The reaction mixture was stirred for 30 min and trimethylsilyl azide (3.60 g, 31.2 mmol) was added dropwise at room temperature. The reaction mixture was heated to reflux for 4 hr. The reaction mixture was diluted with EtOAc and washed with ice water, aq. NaHCO₃ solution and saturated brine solution, dried over anhydrous Na₂SO₄, and concentrated under reduced pressure to afford the crude product. This was purified by column chromatography (60-120 mesh silica gel), eluting with 20% ethyl acetate/pet ether, to give the title compound (1.80 g) as a pale yellow liquid.

MS ES+ve m/z 288 (M+H).
¹H NMR (400 MHz, Chloroform-d) δ ppm 2.18 (s, 3H), 5.80 (s, 2H), 8.26-8.29 (m, 2H), 8.85 (s, 1H).

Intermediate 58: {1-[5-(Trifluoromethyl)-2-pyridinyl]-1H-tetrazol-5-yl}methanol

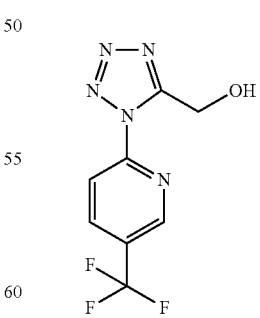

Lithium hydroxide (0.30 g, 12.5 mmol) was added at 0° C. to a solution of {1-[5-(trifluoromethyl)-2-pyridinyl]-1H-tetrazol-5-yl}methyl acetate (Intermediate 57, 1.80 g, 6.27 mmol) in a mixture of ethanol and water (2:1). The reaction mixture was stirred for 3 hr at room temperature. The ethanol was removed under reduced pressure. The residue was diluted with DCM and washed with ice-water, saturated NaHCO₃ solution and brine solution, dried over anhydrous Na₂SO₄, and concentrated under reduced pressure to give the crude product. This was purified by column chromatography (60-120 mesh silica gel), eluting with 30% ethyl acetate/pet ether, to give the title compound (0.90 g).

MS ES+ve m/z 244 (M–H).

$^1$H NMR (400 MHz, Chloroform-d) δ ppm 5.12 (d, J=6.5 Hz, 2H), 5.81 (t, J=6.5 Hz, 3H), 8.26 (d, J=8.5 Hz, 1H), 8.61 (dd, J=8.5, 2 Hz, 1H), 9.12 (s, 1H).

Intermediate 59: 2-[5-(Chloromethyl)-1H-tetrazol-1-yl]-5-(trifluoromethyl)pyridine

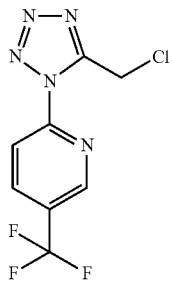

Thionyl chloride (0.22 g, 1.85 mmol) was added at room temperature to a solution of {1-[5-(Trifluoromethyl)-2-pyridinyl]-1H-tetrazol-5-yl}methanol (Intermediate 58, 0.20 g, 0.82 mmol) in toluene, and the reaction mixture was stirred for 2 hr at reflux. The reaction mixture was concentrated under vacuum. The residue was diluted with DCM and washed with ice-water, saturated NaHCO₃ and brine, dried over anhydrous Na₂SO₄, and concentrated under reduced pressure to afford the crude product. This was purified by column chromatography (60-120 mesh silica gel) eluting with 0-20% ethyl acetate/pet ether to give the title compound (60 mg) as a white powder.

MS ES+ve m/z 264 (M+H).

$^1$H NMR (400 MHz, Chloroform-d) δ ppm 5.36 (s, 2H), 8.27 (s, 2H), 8.90 (s, 1H).

Intermediate 60: 4-amino-5-methyl-2-(trifluoromethyl)benzonitrile

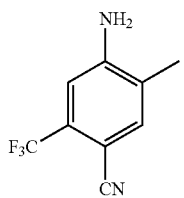

To a solution of 4-amino-5-iodo-2-(trifluoromethyl)benzonitrile (commercially available, for example from Key Organics Ltd., Camelford, UK, 640 mg, 2.05 mmol) and potassium carbonate (567 mg, 4.10 mmol) in 1,4-Dioxane (10 ml) was added tetrakis(triphenylphosphine)palladium(0) (237 mg, 0.205 mmol) and trimethylboroxin (1.43 ml, 10.3 mmol) under argon atmosphere. The reaction mixture was heated to 100° C. overnight. The reaction mixture was diluted in EtOAc (100 ml) and water (50 ml). The aqueous was extracted with EtOAc (100 ml). The organics were combined, passed through a phase separator and concentrated to afford 1 g of a yellow oil which was purified by flash chromatography using a Biotage SP4 (eluting a gradient from 30% to 70% EtOAc in hexane). Relevant fractions were combined and concentrated to afford 300 mg of the title compound as a yellow solid.

MS ES+ve m/z 201 (M+H)

$^1$H NMR (400 MHz, METHANOL-d₄) δ ppm 2.17 (s, 3H) 7.02 (s, 1H) 7.46 (s, 1H)

Intermediate 61: 2-{[4-cyano-2-methyl-5-(trifluoromethyl)phenyl]amino}-2-oxoethyl acetate

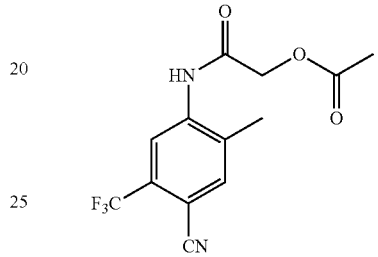

To a solution of 4-amino-5-methyl-2-(trifluoromethyl) benzonitrile (Intermediate 60, 300 mg, 1.50 mmol) and triethylamine (0.230 mL, 1.65 mmol) in dichloromethane (8 mL) was added 2-chloro-2-oxoethyl acetate (0.161 mL, 1.50 mmol) dropwise. The reaction mixture was stirred at room temperature overnight. Reaction mixture was diluted with DCM (100 ml) and water (50 ml) and aqueous was extracted with DCM (100 ml). Organics were combined, passed through a phase separator and concentrated to afford 452 mg of the title compound as a pale yellow powder.

MS ES-ve m/z 299 (M–H)

Intermediate 62: {1-[4-cyano-2-methyl-5-(trifluoromethyl)phenyl]-1H-tetrazol-5-yl}methyl acetate

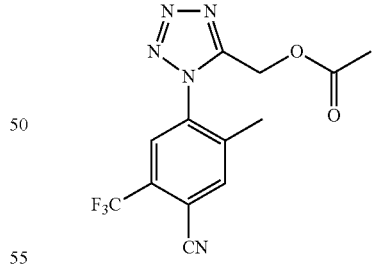

To a solution of 2-{[4-cyano-2-methyl-5-(trifluoromethyl) phenyl]amino}-2-oxoethyl acetate (Intermediate 61, 452 mg, 1.51 mmol) in tetrahydrofuran (10 mL) was added triphenylphosphine (790 mg, 3.01 mmol), di-isopropylazodicarboxylate (0.585 mL, 3.01 mmol) and trimethylsilylazide (0.400 mL, 3.01 mmol). The reaction was stirred at room temperature for 18 hours.

Solvent was removed under vacuum and residue was purified by silica chromatography (Biotage SP4, eluting 0% ethyl acetate in iso-hexane (2 column volumes), then a gradient from 0-50% ethyl acetate in iso-hexane (over 10 column volumes)). Relevant fractions were combined and the solvent removed to yield the title compound as a colourless oil (433 mg).

MS ES+ve m/z 326 (M+H)

Intermediate 63: 4-[5-(hydroxymethyl)-1H-tetrazol-1-yl]-5-methyl-2-(trifluoromethyl)benzonitrile

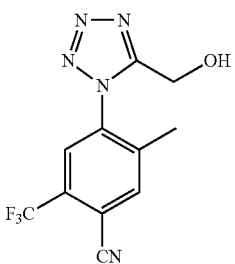 [SMILES: Cc1cc(C#N)c(C(F)(F)F)cc1-n1nnnc1CO]

To a solution of {1-[4-cyano-2-methyl-5-(trifluoromethyl)phenyl]-1H-tetrazol-5-yl}methyl acetate (Intermediate 62, 433 mg, 1.33 mmol) in water (2 mL) and tetrahydrofuran (4 mL), cooled in an ice bath, was added lithium hydroxide monohydrate (56 mg, 1.33 mmol). The reaction was stirred at room temperature for 1 hour and 30 min.

The organic solvent was removed from the reaction under vacuum and the residual mixture diluted with water (30 mL) and extracted with DCM (2*50 ml). The organic extracts were combined, dried (hydrophobic frit) and the solvent removed. Residue was purified by flash chromatography. Relevant fractions were combined and concentrated to afford 147 mg of the title compound as a colourless oil.

MS ES+ve m/z 284 (M+H)

Intermediate 64: 4-[5-(chloromethyl)-1H-tetrazol-1-yl]-5-methyl-2-(trifluoromethyl)benzonitrile

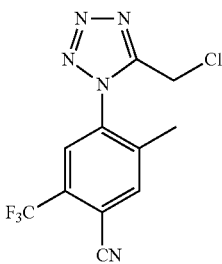 [SMILES: Cc1cc(C#N)c(C(F)(F)F)cc1-n1nnnc1CCl]

To a solution of 4-[5-(hydroxymethyl)-1H-tetrazol-1-yl]-5-methyl-2-(trifluoromethyl)benzonitrile (Intermediate 63, 147 mg, 0.519 mmol) in dichloromethane (3 mL) and N,N-Dimethylformamide (0.5 mL), cooled in an ice bath under argon, was added dropwise thionyl chloride (0.040 mL, 0.545 mmol). The reaction was stirred at 25° C. for two hours. To the reaction was added water (20 mL) and DCM (50 mL) and the reaction partitioned through a hydrophobic frit. The organic layer was evaporated to dryness under vacuum to afford 133 mg of the title compound as a colourless oil.

MS ES+ve m/z 302 (M+H)

$^1$H NMR (400 MHz, METHANOL-$d_4$) δ ppm 2.24 (s, 3H) 4.95 (s, 2H) 8.21 (s, 1H) 8.25 (s, 1H)

Compound 1: 5-[(3,3-Difluoro-1-pyrrolidinyl)methyl]-1-[4-(trifluoromethyl)phenyl]-1H-tetrazole

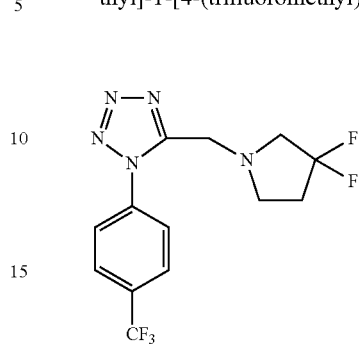

A solution of 3,3-difluoropyrrolidine hydrochloride (129 mg, 0.90 mmol, Sigma-Aldrich), formaldehyde (37%, aqueous, 0.067 mL, 0.9 mmol) and triethylamine (0.125 mL, 0.900 mmol) in methanol (4 mL) was stirred at room temperature for 1.5 h. Trimethylsilyl azide (0.155 mL, 1.170 mmol) and 4-(trifluoromethyl)phenyl isocyanide (200 mg, 1.170 mmol) were added and the reaction mixture stirred for 2 days at room temperature. The solution was concentrated in vacuo. The resulting residue was purified using MDAP. Fractions containing product were combined and concentrated in vacuo. The resulting solid was redissolved in MeOH and passed through a 5 g $NH_2$ ion exchange column to give the title compound as a white solid (252 mg).

$^1$H NMR (400 MHz, DMSO-D6) δ ppm 2.17 (m, 2H) 2.77 (t, J=7.2 Hz, 2H) 2.98 (t, J=13.3 Hz, 2H) 4.09 (m, 2H) 8.01 (d, J=8.6 Hz, 2H) 8.06 (d, J=9.2 Hz, 2H)

MS ES+ve m/z 334 (M+H)

Compound 2: (cis)-2,6-Dimethyl-4-({1-[4-(trifluoromethyl)phenyl]-1H-tetrazol-5-yl}methyl)morpholine

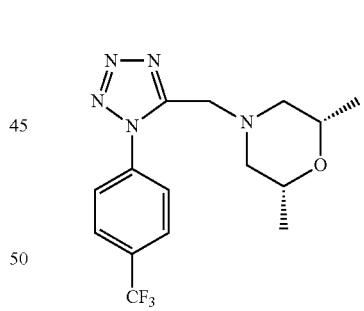

A solution of (cis)-2,6-dimethylmorpholine (0.111 mL, 0.900 mmol, Alfa Aesar, Ward Hill, USA) and formaldehyde (37%, aqueous, 0.067 mL, 0.9 mmol) in methanol (4 mL) was stirred at room temperature for 1.5 h before adding trimethylsilyl azide (0.155 mL, 1.170 mmol) and 4-(trifluoromethyl)phenyl isocyanide (200 mg, 1.170 mmol). After stirring for 2 days at room temperature, the mixture was filtered and the solid collected was purified by silica gel column chromatography (Biotage SP4, gradient elution: 0-100% EtOAc in isohexane) to give the title compound as a solid (241 mg).

$^1$H NMR (400 MHz, DMSO-D6) δ ppm 0.98 (d, J=6.1 Hz, 6H) 1.78 (m, 2H) 2.56 (m, 2H) 3.27 (m, 2H) 3.88 (s, 2H) 8.05 (s, 4H)

MS ES+ve m/z 342 (M+H)

Compound 3: (cis)-2,6-Dimethyl-4-({1-[3-(trifluoromethyl)phenyl]-1H-tetrazol-5-yl}methyl)morpholine

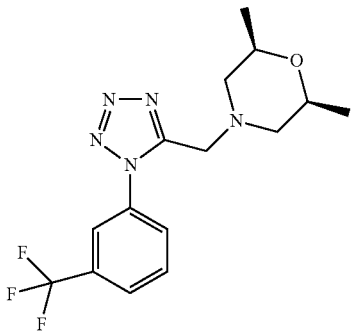 [SMILES: C[C@@H]1CN(Cc2nnnn2-c2cccc(C(F)(F)F)c2)C[C@H](C)O1]

To a solution of cis-dimethylmorpholine (0.185 mL, 1.5 mmol, Alfa Aesar, Ward Hill, USA) was added formaldehyde (37%) (0.112 mL, 1.500 mmol). The reaction mixture was shaken at room temperature for 1 hour before the addition of 3-(trifluoromethyl)phenyl isocyanide (334 mg, 1.950 mmol) and trimethylsilylazide (0.259 mL, 1.950 mmol). The reaction mixture was shaken at room temperature for 18 hours. The solvent was removed under a stream of argon and the residue purified by MDAP (. Fractions containing the desired compound were combined and the solvent removed. The residue was dissolved in methanol and passed through a 1 g SAX SPE cartridge, eluting once with methanol. The methanol fractions were combined and the solvent removed to yield the title compound as a pale yellow gum (0.121 g).

$^1$H NMR (400 MHz, Chloroform-D) δ ppm 1.19 (d, J=6.4 Hz, 6H) 2.06 (dd, J=11.5, 10.2 Hz, 2H) 2.74 (m, 2H) 3.63 (m, 2H) 3.77 (s, 2H) 7.77 (m, 1H) 7.86 (m, 1H) 8.04 (m, 1H) 8.48 (s, 1H).

MS ES+ve m/z 342 (M+H)

Compound 4: 4-({1-[4-(Trifluoromethyl)phenyl]-1H-tetrazol-5-yl}methyl)morpholine

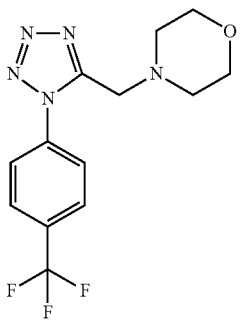 [SMILES: FC(F)(F)c1ccc(-n2nnnc2CN2CCOCC2)cc1]

To a solution of formaldehyde (37% in water) (0.074 ml, 1 mmol) in methanol (2 ml) was added morpholine (0.087 ml, 1.000 mmol). The reaction mixture was stirred at room temperature for 2 hours before the addition of trimethylsilylazide (0.159 ml, 1.200 mmol) and 4-(trifluoromethyl)phenyl isocyanide (0.205 g, 1.200 mmol). The reaction mixture was stirred at room temperature for 45 hours.

The reaction mixture was filtered and the solid collected was washed with a minimum of methanol then dried under vacuum to yield the title compound as a solid (0.216 g).

$^1$H NMR (400 MHz, Chloroform-D) δ ppm 2.60 (m, 4H) 3.68 (m, 4H) 3.80 (s, 2H) 7.88 (d, J=8.3 Hz, 2H) 8.01 (d, J=8.1 Hz, 2H)

MS ES+ve m/z 314 (M+H)

Compound 5: 4-({1-[2-Chloro-4-(trifluoromethyl)phenyl]-1H-tetrazol-5-yl}methyl)morpholine

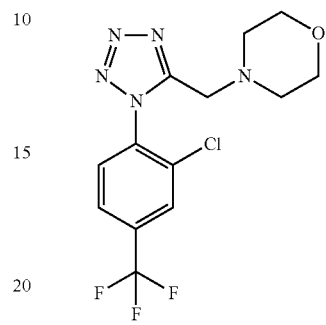

A suspension of potassium tert-butoxide (0.558 g, 4.98 mmol) in tert-Butanol (6 ml) was stirred at 30° C. before the addition of [2-chloro-4-(trifluoromethyl)phenyl]formamide (may be prepared as described in Intermediate 1) (0.445 g, 1.990 mmol). The reaction mixture was stirred until a clear solution formed (approx 5 minutes). To the reaction mixture was added dropwise POCl$_3$ (0.111 mL, 1.194 mmol) and the reaction mixture stirred at 30° C. for 90 minutes. The reaction mixture was poured onto saturated aqueous NaHCO$_3$ (5 mL) and the suspension extracted with petroleum ether 40:60 (2×8 mL). The organic layers were combined, passed through a hydrophobic frit and the solvent removed under a stream of argon to yield orange gum.

To a solution of morpholine (0.173 mL, 1.990 mmol) in methanol (3 mL) was added formaldehyde (37%, aqueous) (0.148 mL, 1.990 mmol). The reaction mixture was shaken at room temperature for 2 hours. The solution was then added to the crude iso-nitrile together with trimethylsilylazide (0.264 mL, 1.990 mmol). The reaction mixture was shaken at room temperature for a further 18 hours.

The solvent was removed under a stream of argon and the residue purified by silica chromatography (Biotage SP4, eluting 10% EtOAc in iso-hexane (5 column volumes) then 10-35% EtOAc in iso-hexane (over 15 column volumes)) to yield the title compound as a solid (132 mg)

$^1$H NMR (400 MHz, Chloroform-D) δ ppm 2.38 (t, J=4.6 Hz, 4H) 3.42 (m, 4H) 3.85 (m, 2H) 7.61 (m, 1H) 7.77 (m, 1H) 7.93 (m, 1H)

MS ES+ve m/z 348 (M+H)

Compound 6: 5-[2-(3,3-Difluoro-1-pyrrolidinyl)ethyl]-1-[4-(trifluoromethyl)phenyl]-1H-tetrazole

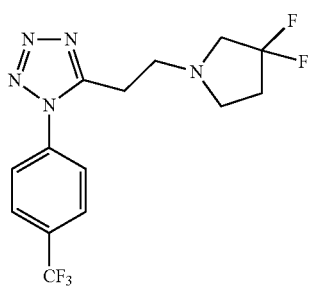 [SMILES: FC1(F)CCN(CCc2nnnn2-c2ccc(C(F)(F)F)cc2)C1]

To a solution of dimethyl(-2-{1-[4-(trifluoromethyl)phenyl]-1H-tetrazol-5-yl}ethenyl)amine (may be prepared as described in Intermediate 4) (100 mg, 0.353 mmol) in ethanol (2-mL) was added 3,3-difluoropyrrolidine hydrochloride (113 mg, 1.059 mmol, Fluorochem, Old Glossop, UK). The reaction mixture was heated to 65° C. and stirred for 4 hours. The reaction mixture was cooled and the solvent removed under vacuum. The solid residue was partitioned between DCM (3 mL) and sat.NaHCO₃ (2 mL). The organic layer was collected via a hydrophobic frit and the solvent removed under vacuum. The residue was dissolved in dry dichloromethane (2 mL) before the addition of sodium triacetoxyborohydride (224 mg, 1.059 mmol). The reaction mixture was shaken at room temperature for 18 hours.

To the reaction mixture was added further sodium triacetoxyborohydride (224 mg, 1.059 mmol) and the reaction mixture shaken at room temperature for a further 6 days. The reaction mixture was partitioned between DCM (3 mL) and water (2 mL). The organic layer was collected via a hydrophobic frit and the solvent removed under a stream of argon. The residue was purified by MDAP. The isolated product was partitioned between DCM (3 mL) and sat.NaHCO₃ (2 mL). The organic layer was collected via a hydrophobic frit and the solvent removed under vacuum to yield the title compound as a solid (18 mg)

MS ES+ve m/z 318 (M+H)

$^1$H NMR (400 MHz, Chloroform-D) δ ppm 2.19 (m, 2H) 2.68 (t, J=7.0 Hz, 2H) 2.80 (t, J=12.9 Hz, 2H) 2.98 (t, J=7.0 Hz, 2H) 3.08 (m, 2H) 7.67 (d, J=8.6 Hz, 2H) 7.89 (d, J=8.8 Hz, 2H)

Compound 7: 5-(1-Pyrrolidinylmethyl)-1-[4-(trifluoromethyl)phenyl]-1H-tetrazole

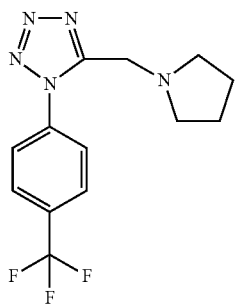 [SMILES: FC(F)(F)c1ccc(-n2nnnc2CN2CCCC2)cc1]

A solution of pyrrolidine (0.074 mL, 0.90 mmol) and formaldehyde (37%, aqueous, 0.067 mL, 0.9 mmol) in methanol (4 mL) was stirred at room temperature for 1.5 h before adding trimethylsilyl azide (0.155 mL, 1.170 mmol) and 4-(trifluoromethyl)phenyl isocyanide (200 mg, 1.170 mmol, Fluorochem, Old Glossop, UK). After stirring for 2 days the solution was concentrated in vacuo. The resulting residue was purified using MDAP. Fractions containing product were combined and concentrated in vacuo. The resulting solid was redissolved in MeOH and passed through a 5 g NH₂ ion exchange column to yield the title compound as a solid (230 mg).

MS ES+ve m/z 293 (M+H)

$^1$H NMR (400 MHz, Chloroform-D) δ ppm 1.82 (m, 4H) 2.64 (m, 4H) 3.92 (s, 2H) 7.86 (d, J=8.3 Hz, 2H) 8.05 (d, J=8.1 Hz, 2H)

Compound 8: N-({1-[4-(Trifluoromethyl)phenyl]-1H-tetrazol-5-yl}methyl)-2-propanamine

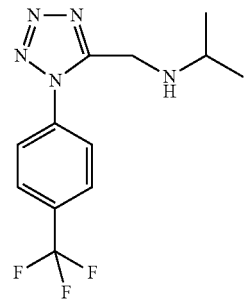 [SMILES: CC(C)NCc1nnnn1-c1ccc(C(F)(F)F)cc1]

A solution of (1-methylethyl)amine (0.077 mL, 0.900 mmol) and formaldehyde (35% aqueous) (0.067 mL, 0.9 mmol) in methanol (4 mL) was stirred at room temperature for 1.5 h before adding trimethylsilyl azide (0.155 mL, 1.170 mmol) and 4-(trifluoromethyl)phenyl isocyanide (200 mg, 1.170 mmol, Fluorochem, Old Glossop, UK). After stirring for 2 days the solution was concentrated in vacuo. The resulting residue was purified using MDAP. Fractions containing product were combined and concentrated in vacuo. The resulting solid was redissolved in MeOH and passed through a 5 g NH₂ ion exchange column to give the title compound as a white solid (75 mg).

MS ES+ve m/z 286 (M+H)

$^1$H NMR (400 MHz, Chloroform-D) δ ppm 1.10 (d, J=6.4 Hz, 6H) 2.90 (m, 1H) 4.08 (s, 2H) 7.87 (d, J=8.3 Hz, 2H) 7.98 (d, J=8.3 Hz, 2H)

Compound 9: 4-(2-{1-[4-(Trifluoromethyl)phenyl]-1H-tetrazol-5-yl}ethyl)morpholine hydrochloride

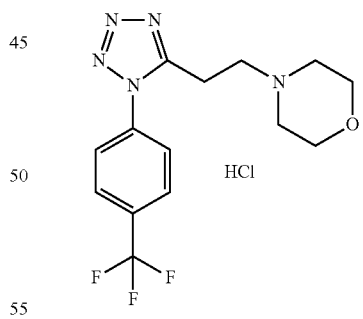

To a solution of dimethyl(2-{1-[4-(trifluoromethyl)phenyl]-1H-tetrazol-5-yl}ethenyl)amine (may be prepared as described in Intermediate 4) (64 mg, 0.226 mmol) in ethanol (2 mL) was added morpholine (0.197 mL, 2.259 mmol) and acetic acid (0.129 mL, 2.259 mmol). The reaction mixture was heated to 70° C. and stirred for 3 hours. The reaction mixture was allowed to cool and the solvent removed under vacuum to yield an orange gum. The residue was dissolved in dichloromethane (2 mL) before the addition of sodium triacetoxyborohydride (144 mg, 0.678 mmol). The reaction mixture was stirred at room temperature for 18 hours.

The reaction mixture was partitioned between DCM (3 mL) and saturated NaHCO$_3$ (2 mL). The organic layer was collected via a hydrophobic frit and the solvent removed under vacuum. The residue was dissolved in dichloromethane (2 mL) before the addition of sodium triacetoxyborohydride (144 mg, 0.678 mmol). The reaction mixture was stirred at room temperature for 22 hours.

The reaction mixture was partitioned between DCM (3 mL) and saturated NaHCO$_3$ (2 mL). The organic layer was collected via a hydrophobic frit and the solvent removed under vacuum. The residue was purified by MDAP to yield a solid. The solid was dissolved in a minimum of methanol before the addition of 1N HCl in diethyl ether (3 mL). The solvent was removed under a stream of argon. The residue was triturated with diethyl ether (2×1 mL) then dried under vacuum to yield the title compound as a solid (32 mg).

MS ES+ve m/z 328 (M+H)

$^1$H NMR (400 MHz, DMSO-D6) δ ppm 3.16 (m, 2H) 3.50 (m, 4H) 3.66 (m, 2H) 3.75 (m, 2H) 3.98 (m, 2H) 7.98 (d, J=8.6 Hz, 2H) 8.09 (d, J=8.3 Hz, 2H)

Compound 10: 4-{[1-(2,4-Dichlorophenyl)-1H-tetrazol-5-yl]methyl}morpholine

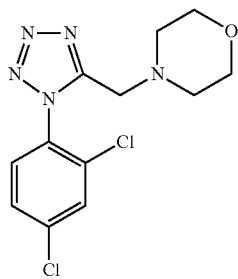 [SMILES: Clc1ccc(-n2nnnc2CN2CCOCC2)c(Cl)c1]

A suspension of potassium tert-butoxide (493 mg, 4.39 mmol) in tert-butanol (4 ml) was stirred at 30° C. before the addition of (2,4-dichlorophenyl)formamide (may be prepared as described in Intermediate 5) (334 mg, 1.76 mmol). The reaction mixture was stirred until a clear solution formed (approx 5 minutes). To the reaction mixture was added dropwise phosphorus oxychloride (0.098 ml, 1.06 mmol) and the reaction mixture stirred at 30° C. for 90 minutes. The reaction mixture was poured onto saturated aqueous NaHCO$_3$ (5 mL) and the suspension extracted with petroleum ether 40:60 (2×8 mL). The organic layers were combined, passed through a hydrophobic frit and the solvent removed under a stream of argon to yield the crude intermediate isocyanide as an orange gum.

To a solution of morpholine (0.138 mL, 1.58 mmol) in methanol (3 mL) was added formaldehyde (37% aqueous) (0.118 mL, 1.582 mmol). The reaction mixture was shaken at room temperature for 2 hours. To the reaction mixture was added the crude isocyanide and trimethylsilylazide (0.233 mL, 1.76 mmol). The reaction mixture was shaken at room temperature for a further 18 hours.

The solvent was removed under a stream of argon and the residue purified by silica chromatography (Biotage SP4, eluting 10% EtOAc in iso-hexane (5 column volumes) then 10-35% EtOAc in iso-hexane (over 15 column volumes)) to yield the title compound as a solid (183 mg)

MS ES+ve m/z 314 (M+H)

$^1$H NMR (400 MHz, Chloroform-D) δ ppm 2.39 (m, 4H) 3.47 (m, 4H) 3.80 (s, 2H) 7.39 (d, J=8.6 Hz, 1H) 7.48 (dd, J=8.6, 2.2 Hz, 1H) 7.66 (d, J=2.2 Hz, 1H)

Compound 11: (cis)-4-(5-{[2,6-Dimethyl-4-morpholinyl]methyl}-1H-tetrazol-1-yl)benzonitrile

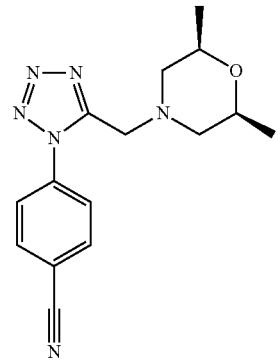 [SMILES: C[C@@H]1CN(Cc2nnnn2-c2ccc(C#N)cc2)C[C@H](C)O1]

To a solution of (cis)-2,6-dimethylmorpholine (104 mg, 0.9 mmol, Alfa Aesar, Ward Hill, USA) in methanol (3 mL) was added formaldehyde (37% aqueous) (0.067 mL, 0.900 mmol). The reaction mixture was shaken at room temperature for 40 minutes. To the reaction mixture was added 4-isocyanobenzonitrile (128 mg, 1 mmol) and trimethylsilylazide (0.133 mL, 1.00 mmol). The reaction mixture was shaken at room temperature for a further 18 hours.

The reaction mixture was filtered and the solid collected was triturated with methanol (1 mL) then dried under vacuum to yield the title compound as a solid (169 mg).

$^1$H NMR (400 MHz, Chloroform-D) δ ppm 1.17 (d, J=6.4 Hz, 6H) 2.02 (t, J=10.3 Hz, 2H) 2.68 (m, 2H) 3.58 (m, 2H) 3.78 (m, 2H) 7.91 (m, 2H) 8.06 (m, 2H)

Compound 12: 8-({1-[3-(Trifluoromethyl)phenyl]-1H-tetrazol-5-yl}methyl)-2,8-diazaspiro[4.5]decan-1-one

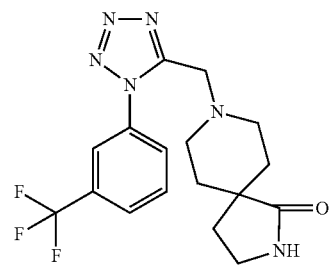 [SMILES: O=C1NCCC12CCN(Cc1nnnn1-c1cccc(C(F)(F)F)c1)CC2]

To a solution of 5-(chloromethyl)-1-[3-(trifluoromethyl) phenyl]-1H-tetrazole (200 mg, 0.762 mmol, commercially available from Otava, Kiev, Ukraine) in acetonitrile (4 mL) was added 2,8-diazaspiro[4.5]decan-1-one hydrochloride (290 mg, 1.52 mmol, Tyger Scientific, Ewing, USA) and triethylamine (0.318 mL, 2.29 mmol). The reaction mixture was heated at 120° C. for 20 minutes in a microwave reactor. The reaction mixture was then cooled and the solvent removed under vacuum. The residue was purified by MDAP. Fractions containing the desired product were combined and the solvent removed. The product was partitioned between DCM (6 mL) and saturated aqueous NaHCO₃ (3 mL) and the organic layer collected via a hydrophobic frit. The solvent was removed under a stream of argon to yield the title compound as a solid (0.161 g).

MS ES+ve m/z 381 (M+H)

¹H NMR (400 MHz, Chloroform-d) d ppm 1.48 (d, 2H) 1.88-1.97 (m, 2H) 2.06 (t, J=6.9 Hz, 2H) 2.37 (td, J=11.4, 2.6 Hz, 2H) 2.92 (dt, J=11.8, 3.8 Hz, 2H) 3.35 (t, J=6.9 Hz, 2H) 3.78 (s, 2H) 5.95 (br. s., 1H) 7.74 (t, J=7.9 Hz, 1H) 7.83 (d, J=7.9 Hz, 1H) 8.11 (d, J=8.1 Hz, 1H) 8.33 (s, 1H)

Compound 13: (cis)-4-{[1-(4-Chlorophenyl)-1H-tetrazol-5-yl]methyl}-2,6-dimethylmorpholine

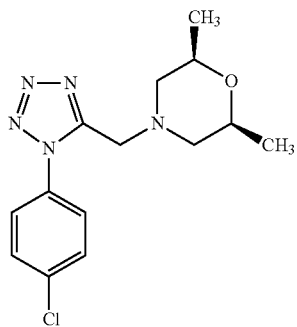 [SMILES: C[C@@H]1CN(Cc2nnnn2-c2ccc(Cl)cc2)C[C@H](C)O1]

To a solution of (cis)-2,6-dimethylmorpholine (104 mg, 0.900 mmol, Alfa Aesar, Ward Hill, USA) in methanol (3 mL) was added formaldehyde (37% aqueous) (0.067 mL, 0.900 mmol). The reaction mixture was shaken at room temperature for 2 hours. To the reaction mixture was added 4-chlorophenyl isocyanide (138 mg, 1 mmol) and trimethylsilylazide (0.133 mL, 1.00 mmol). The reaction mixture was shaken at room temperature for a further 18 hours.

The solvent was removed under a stream of argon and the residue triturated with methanol (2 mL), filtered and dried in vacuo to yield the title compound as a solid (158 mg).

MS ES+ve m/z 308 (M+H)

¹H NMR (400 MHz, Chloroform-d) δ ppm 1.16 (d, J=6.36 Hz, 6H) 1.99 (dd, J=11.18, 10.30 Hz, 2H) 2.66-2.74 (m, 2H) 3.54-3.64 (m, 2H) 3.72 (s, 2H) 7.53-7.59 (m, 2H) 7.72-7.78 (m, 2H)

Compound 14: 4-[(1-{4-[(Trifluoromethyl)oxy]phenyl}-1H-tetrazol-5-yl)methyl]morpholine

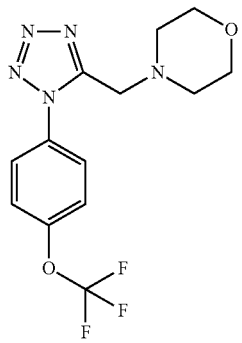 [SMILES: FC(F)(F)Oc1ccc(-n2nnnc2CN2CCOCC2)cc1]

A suspension of potassium tert-butoxide (0.462 g, 4.12 mmol) in tert-butanol (6 ml) was stirred at 30° C. before the addition of {4-[(trifluoromethyl)oxy]phenyl}formamide (may be prepared as described in Intermediate 6) (0.338 g, 1.65 mmol). The reaction mixture was stirred until a clear solution formed (approx 5 minutes). To the reaction mixture was added dropwise POCl₃ (0.092 mL, 0.989 mmol) and the reaction mixture stirred at 30° C. for 90 minutes. The reaction mixture was poured onto saturated aqueous NaHCO₃ (5 mL) and the suspension extracted with petroleum ether 40:60 (2×8 mL). The organic layers were combined, passed through a hydrophobic frit and the solvent removed under a stream of argon to yield orange gum.

To a solution of morpholine (0.144 mL, 1.65 mmol) in methanol (3 mL) was added formaldehyde (37% aqueous) (0.123 mL, 1.65 mmol). The reaction mixture was shaken at room temperature for 2 hours. The solution was then added to the crude iso-nitrile together with trimethylsilylazide (0.219 mL, 1.65 mmol). The reaction mixture was shaken at room temperature for a further 18 hours.

The solvent was removed under a stream of argon and the residue purified by silica chromatography (Biotage SP4, eluting 10% EtOAc in iso-hexane (5 column volumes) then 10-35% EtOAc in iso-hexane (over 15 column volumes)). Fractions containing the product were combined and the solvent removed. The residue was purified by MDAP. The purified sample was dissolved in a minimum of methanol and passed through a SAX SPE cartridge, eluting once with methanol. The methanol fractions were combined and the solvent removed to yield the title compound as a solid (46 mg)

¹H NMR (400 MHz, Chloroform-D) δ ppm 2.51 (t, J=4.5 Hz, 4H) 3.61 (t, J=4.5 Hz, 4H) 3.71 (s, 2H) 7.37 (m, 2H) 7.80 (m, 2H)

MS ES+ve m/z 330 (M+H)

Compound 15: 4-({1-[3-(Trifluoromethyl)phenyl]-1H-tetrazol-5-yl}methyl)thiomorpholine 1,1-dioxide

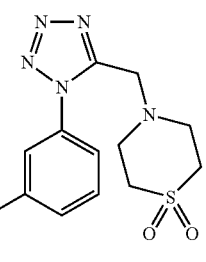

To a solution of 5-(chloromethyl)-1-[3-(trifluoromethyl)phenyl]-1H-tetrazole (300 mg, 1.14 mmol, commercially available from Otava, Kiev, Ukraine) in acetonitrile (4 mL) was added thiomorpholine 1,1-dioxide (309 mg, 2.29 mmol, Apollo Scientific, Stockport, UK) and triethylamine (0.175 mL, 1.26 mmol). The reaction mixture was heated at 120° C. for 20 minutes in a microwave reactor. The reaction mixture was cooled and then the solvent removed under vacuum. The residue was purified by MDAP. Fractions containing the desired product were combined and the solvent removed to yield a colourless gum. The product was partitioned between DCM (6 mL) and saturated aqueous NaHCO₃ (3 mL) and the organic layer collected via a hydrophobic frit. The solvent was removed under a stream of argon to yield the title compound as a white solid (0.246 g)

MS ES+ve m/z 362 (M+H)

¹H NMR (400 MHz, Chloroform-d) d ppm 3.05-3.11 (m, 4H) 3.16-3.23 (m, 4H) 3.96 (s, 2H) 7.80 (t, J=7.9 Hz, 1H) 7.89 (d, J=7.9 Hz, 1H) 7.95 (d, J=7.9 Hz, 1H) 8.18 (s, 1H)

Compound 16: (cis)-2,6-Dimethyl-4-(2-{1-[4-(trifluoromethyl)phenyl]-1H-tetrazol-5-yl}ethyl)morpholine

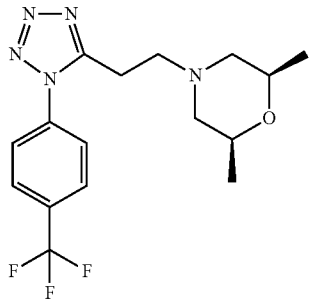 [SMILES: C[C@@H]1CN(CCc2nnnn2-c2ccc(C(F)(F)F)cc2)C[C@H](C)O1]

To a solution of dimethyl(2-{1-[4-(trifluoromethyl)phenyl]-1H-tetrazol-5-yl}ethenyl)amine (may be prepared as described in Intermediate 4) (100 mg, 0.353 mmol) in ethanol (2 mL) was added (cis)-2,6-dimethylmorpholine (122 mg, 1.059 mmol, Alfa Aesar, Ward Hill, USA) and acetic acid (0.061 mL, 1.059 mmol). The reaction mixture was heated to 65° C. and stirred for 4 hours. The reaction mixture was cooled and the solvent removed under vacuum. The residue was dissolved in ethanol (2 mL) before the addition of further (cis)-2,6-dimethylmorpholine (122 mg, 1.059 mmol) and acetic acid (0.061 mL, 1.059 mmol). The reaction mixture was heated to 65° C. and stirred for 3 hours. The reaction mixture was cooled and the solvent removed under vacuum. The solid residue was partitioned between DCM (3 mL) and saturated aqueous NaHCO₃ (2 mL). The organic layer was collected via a hydrophobic frit and the solvent removed under vacuum. The residue was dissolved in dry dichloromethane (DCM) (2 mL) before the addition of sodium triacetoxyborohydride (224 mg, 1.06 mmol). The reaction mixture was shaken at room temperature for 18 hours. The reaction mixture was partitioned between DCM (3 mL) and saturated aqueous NaHCO₃ (2 mL). The organic layer was collected via a hydrophobic frit and the solvent removed under vacuum. The residue was purified by MDAP. Fractions containing the desired product were combined and the solvent removed. The residue was dissolved in methanol and passed through a 1 g SAX cartridge, eluting once with methanol. The methanol fractions were combined and the solvent removed to yield a yellow gum. The gum was dissolved in a minimum of methanol and 1N HCl in diethyl ether (2 mL) added. The solvent was removed under a stream of argon to yield a sticky orange gum. The product was partitioned between saturated aqueous NaHCO₃ (1 mL) and DCM (1 mL). The organic layer was collected via a hydrophobic frit and the solvent removed under vacuum. The product was further purified by silica chromatography (Biotage SP4 eluting a gradient from 50-100% EtOAc over 15 column volumes) to yield the title compound as a solid (12 mg).

¹H NMR (400 MHz, Chloroform-D) δ ppm 1.09 (d, J=6.4 Hz, 6H) 1.72 (dd, J=10.2, 1.2 Hz, 2H) 2.53 (m, 2H) 2.80 (t, J=7.1 Hz, 2H) 3.12 (t, J=7.0 Hz, 2H) 3.44 (m, 2H) 7.69 (d, J=8.2 Hz, 2H) 7.89 (d, J=8.2 Hz, 2H)
MS ES+ve m/z 356 (M+H)

Compound 17: 4-{5-[(3,3-Difluoro-1-pyrrolidinyl)methyl]-1H-tetrazol-1-yl}benzonitrile

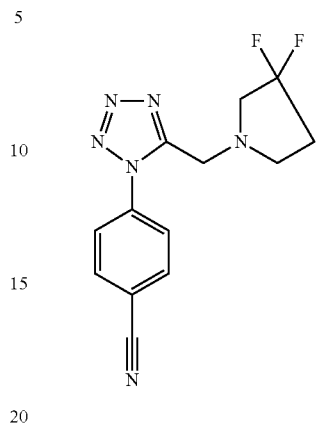

To a solution of 3,3-difluoropyrrolidine hydrochloride (129 mg, 0.90 mmol, Sigma-Aldrich) in methanol (2 mL) was added formaldehyde (37% aqueous) (0.067 mL, 0.90 mmol) and triethylamine (0.125 mL, 0.90 mmol). The reaction mixture was shaken at room temperature for 40 minutes. To the reaction mixture was added 4-isocyanobenzonitrile (128 mg, 1.00 mmol) and trimethylsilylazide (0.133 mL, 1.00 mmol). The reaction mixture was shaken at room temperature for a further 18 hours.

The solvent was removed under vacuum and the residue triturated with methanol (2 mL), filtered and the solid collected dried under vacuum to yield the title compound as a solid (80 mg).

¹H NMR (400 MHz, Chloroform-d) d ppm 2.32 (tt, J=14.5, 7.1 Hz, 2H) 2.90 (1, J=7.0 Hz, 2H) 3.05 (t, J=12.6 Hz, 2H) 3.97 (s, 2H) 7.90-7.94 (m, 2H) 7.96-8.01 (m, 2H)

Compound 18: 1-(4-Chlorophenyl)-5-[(3,3-difluoro-1-pyrrolidinyl)methyl]-1H-tetrazole

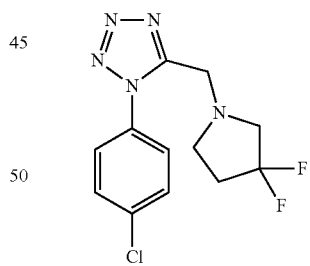

To a solution of 3,3-difluoropyrrolidine hydrochloride (129 mg, 0.90 mmol, Sigma-Aldrich) in methanol (3 mL) was added formaldehyde (37% aqueous) (0.067 mL, 0.90 mmol) and triethylamine (0.139 mL, 1.00 mmol). The reaction mixture was shaken at room temperature for 2 hours. To the reaction mixture was added 4-chlorophenyl isocyanide (138 mg, 1.00 mmol) and trimethylsilylazide (0.133 mL, 1.00 mmol). The reaction mixture was shaken at room temperature for a further 18 hours.

The solvent was removed under a stream of argon and the residue purified by silica chromatography (Biotage SP4, eluting 10% EtOAc in iso-hexane (5 column volumes) then 10-35% EtOAc in iso-hexane (over 15 column volumes)) to yield the title compound as a solid (0.124 g).

MS ES+ve m/z 300 (M+H)

$^1$H NMR (400 MHz, Chloroform-d) δ ppm 2.31 (tt, 2H) 2.89 (t, J=7.0 Hz, 2H) 3.04 (t, J=12.7 Hz, 2H) 3.91 (s, 2H) 7.55-7.60 (m, 2H) 7.66-7.71 (m, 2H)

The following Compounds 19 to 23 are commercially available:

Compound 19: 4-({1-[3-(Trifluoromethyl)phenyl]-1H-tetrazol-5-yl}methyl)morpholine

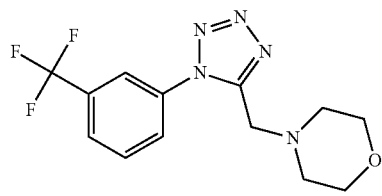 [SMILES: FC(F)(F)c1cccc(-n2nnnc2CN2CCOCC2)c1]

Commercially available from Vitas-M screening Collection, Moscow, Russia

Compound 19a: 4-({1-[3-(trifluoromethyl)phenyl]-1H-tetrazol-5-yl}methyl)morpholine hydrochloride salt

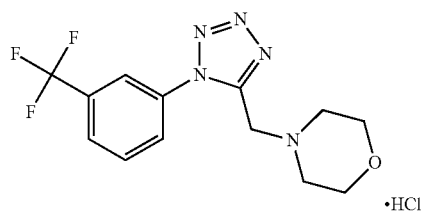 [SMILES: FC(F)(F)c1cccc(-n2nnnc2CN2CCOCC2)c1 ; Cl]

Preparative Procedure:

To a solution of formaldehyde (37% in water) (0.112 ml, 1.5 mmol) in methanol (2 ml) was added morpholine (0.131 ml, 1.50 mmol). The reaction mixture was stirred at room temperature for 2 hours before the addition of trimethylsilylazide (0.239 ml, 1.80 mmol) and 3-(trifluoromethyl)phenyl isocyanide (257 mg, 1.500 mmol). The reaction mixture was stirred at room temperature for 18 hours. The solvent was removed under a stream of argon and the residue purified by silica chromatography (Biotage SP4, eluting 10% EtOAc in iso-hexane (3 column volumes) then a gradient 10-30% EtOAc in iso-hexane (over 12 column volumes)) to yield the title compound as a solid.

$^1$H NMR (400 MHz, Chloroform-D) δ ppm 2.61 (m, 4H) 3.70 (m, 4H) 3.78 (s, 2H) 7.75 (m, 1H) 7.84 (m, 1H) 8.02 (m, 1H) 8.45 (m, 1H)

MS ES+ve m/z 314 (M+H)

The above compound was dissolved in diethyl ether (2 mL) and 1N HCl in diethyl ether (2 mL) added. The solvent was removed from the suspension under a stream of argon and the solid residue dried under vacuum. The isolated compound was triturated with diethyl ether (2×1 mL) then dried overnight at 40° C. under vacuum to yield the hydrochloride salt of the title compound as a solid (59 mg).

MS ES+ve m/z 314 (M+H)

$^1$H NMR (400 MHz, MeOD) δ ppm 3.50 (br.s, 4H) 3.96 (m, 4H) 7.94 (m, 1H) 7.97 (m, 1H) 8.04 (m, 1H) 8.09 (m, 1H)

Compound 20: 4-{[1-(4-Chlorophenyl)-1H-tetrazol-5-yl]methyl}morpholine

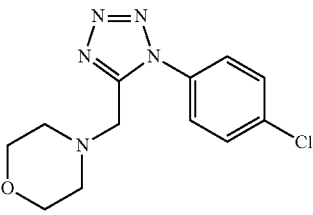 [SMILES: Clc1ccc(-n2nnnc2CN2CCOCC2)cc1]

Commercially available from Ryan Scientific, Mount Pleasant, USA or AsInEx, Moscow, Russia.

Compound 21: 4-{[1-(3,4-Dichlorophenyl)-1H-tetrazol-5-yl]methyl}morpholine

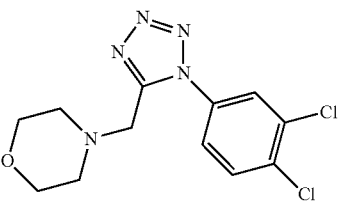 [SMILES: Clc1ccc(-n2nnnc2CN2CCOCC2)cc1Cl]

Commercially available from AsInEx, Moscow, Russia.

Compound 22: 1-{[1-(4-Chlorophenyl)-1H-tetrazol-5-yl]methyl}-4-(methylsulfonyl)piperazine

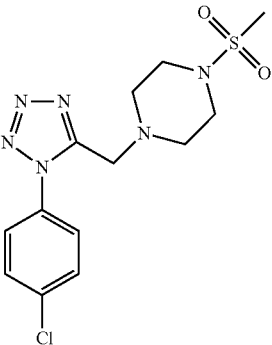 [SMILES: CS(=O)(=O)N1CCN(Cc2nnnn2-c2ccc(Cl)cc2)CC1]

Commercially available from Life Chemicals Inc, Burlington, Canada.

Compound 23: 1-{[1-(4-Chlorophenyl)-1H-tetrazol-5-yl]methyl}-4-(propylsulfonyl)piperazine

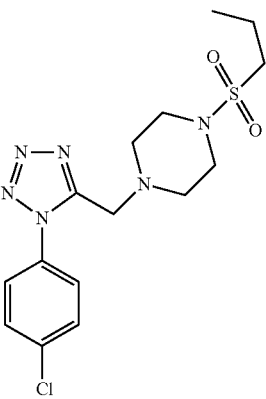 [SMILES: CCCS(=O)(=O)N1CCN(Cc2nnnn2-c2ccc(Cl)cc2)CC1]

Commercially available from Life Chemicals Inc, Burlington, Canada.

Prepared Compounds:

Compound 24: 1-({1-[3-(Trifluoromethyl)phenyl]-1H-tetrazol-5-yl}methyl)-3-pyrrolidinecarbonitrile hydrochloride

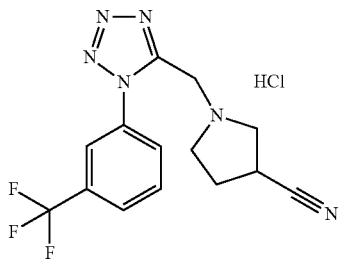 [SMILES: N#CC1CCN(Cc2nnnn2-c2cccc(C(F)(F)F)c2)C1 ; Cl]

Preparative procedure: To a solution of 5-(chloromethyl)-1-[3-(trifluoromethyl)phenyl]-1H-tetrazole (200 mg, 0.762 mmol, commercially available from Otava, Kiev, Ukraine) in acetonitrile (4 mL) was added 3-pyrrolidinecarbonitrile (202 mg, 1.52 mmol, J&W Pharmlabs, Levittown, USA) and triethylamine (0.329 mL, 2.36 mmol). The reaction mixture was heated at 120° C. for 20 minutes in a microwave reactor. The reaction mixture was cooled then the solvent removed under vacuum. The residue was purified by MDAP. Fractions containing the desired product were combined and the solvent removed. The product was dissolved in 1 ml of DCM and 0.5 ml of 1M HCl in ether was added. Solvent was removed and the product was dried in a vacuum oven over the weekend to afford the title compound as a white solid (170 mg).

$^1$H NMR (400 MHz, METHANOL-$d_4$) δ ppm 2.33-2.44 (m, 1H) 2.53-2.64 (m, 1H) 3.50-3.59 (m, 1H) 3.61-3.75 (m, 2H) 3.75-3.87 (m, 2H) 4.90 (s, 2H) 7.89-7.94 (m, 1H) 7.95-8.00 (m, 1H) 8.02 (d, J=7.9 Hz, 1H) 8.09 (s, 1H)

MS ES+ve m/z 323 (M+H)

Compound 25: (3R)-3-Methyl-4-({1-[3-(trifluoromethyl)phenyl]-1H-tetrazol-5-yl}methyl)morpholine hydrochloride

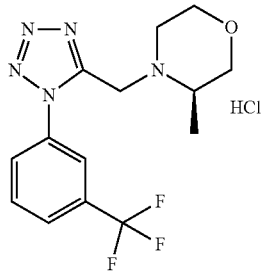 [SMILES: C[C@@H]1COCCN1Cc1nnnn1-c1cccc(C(F)(F)F)c1 ; Cl]

A solution of (3R)-3-methylmorpholine hydrochloride (52.4 mg, 0.381 mmol), 5-(chloromethyl)-1-[3-(trifluoromethyl)phenyl]-1H-tetrazole (50 mg, 0.190 mmol, commercially available from Otava, Kiev, Ukraine) and di-isopropylethylamine (0.067 mL, 0.381 mmol) in acetonitrile (1.5 mL) was heated to 120° C. for 15 minutes in a microwave reactor. The reaction mixture was allowed to cool and the solvent removed under vacuum. The residue was purified by MDAP and fractions containing the desired product were combined and the solvent removed. The residue was dissolved in a minimum of diethyl ether before the dropwise addition of 1N HCl in diethyl ether (3 mL) leading to precipitation. The solvent was removed under a stream of argon and the residue triturated with diethyl ether then dried under vacuum to yield the title compound as a white solid (46 mg).

$^1$H NMR (400 MHz, METHANOL-$d_4$) δ ppm 1.35 (d, J=6.4 Hz, 3H) 3.32-3.38 (m, integration overlapping with solvent, assume 1H) 3.59-3.75 (m, 3H) 3.83-3.91 (m, 1H) 3.95-4.03 (m, 2H) 4.76 (d, J=15.8 Hz, 1H) 5.06 (d, J=16.0 Hz, 1H) 7.90-7.96 (m, 1H) 7.96-8.01 (m, 1H) 8.05 (d, J=7.7 Hz, 1H) 8.11 (s, 1H)

MS ES+ve m/z 323 (M+H)

Compound 26: (cis)-2,6-Dimethyl-4-({1-[4-(methylthio)phenyl]-1H-tetrazol-5-yl}methyl)morpholine

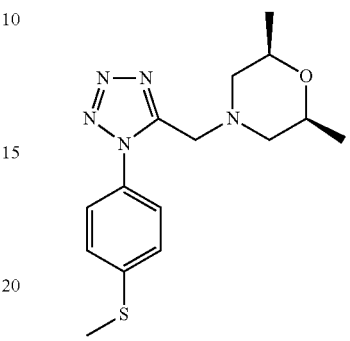

To a solution of formaldehyde (37% in water) (0.200 ml, 2.68 mmol) in methanol (4 ml) was added (cis)-2,6-dimethylmorpholine (0.330 ml, 2.68 mmol, Alfa Aesar, Ward Hill, USA). The reaction mixture was stirred at room temperature for 2 hours before the addition of trimethylsilylazide (0.356 ml, 2.68 mmol) and 4-(methylthio)phenyl isocyanide (400 mg, 2.68 mmol, commercially available from Priaxon, Munich, Germany) The reaction mixture was stirred at room temperature for 67 hours. The reaction mixture was partitioned between DCM (50 ml) and water (20 ml). The aqueous layer was extracted with DCM (50 ml). The organic layers were combined, dried over MgSO$_4$, filtered and concentrated. The crude product was purified by flash chromatography using a gradient of iso-hexane/ethyl acetate (0 to 50%). Fractions were combined and concentrated to afford a solid (530 mg). 60 mg of this material was dissolved in a mixture of MeOH and DCM and loaded onto an SCX cartridge, washed with MeOH and eluted with methanolic ammonia. Relevant fractions were combined and concentrated to afford the title compound as white crystals (40 mg).

MS ES+ve m/z 320 (M+H) $^1$H NMR (400 MHz, CHLOROFORM-d) δ ppm 1.16 (d, J=6.4 Hz, 6H) 1.98 (t, J=10.7 Hz, 2H) 2.56 (s, 3H) 2.72 (d, J=10.3 Hz, 2H) 3.56-3.65 (m, 2H) 3.71 (s, 2H) 7.39 (d, J=8.8 Hz, 2H) 7.66 (d, J=8.8 Hz, 2H)

Compound 27—4-(5-{[cis-2,6-Dimethyl-4-morpholinyl]methyl}-1H-tetrazol-1-yl)-3-methylbenzonitrile hydrochloride

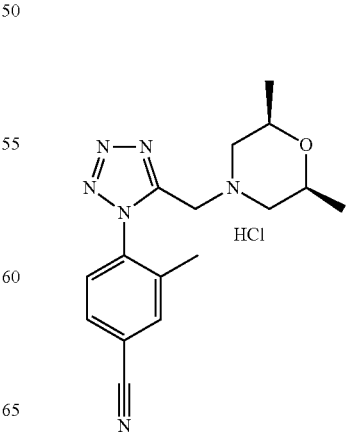

Argon was bubbled through a solution of (cis)-4-{[1-(4-bromo-2-methylphenyl)-1H-tetrazol-5-yl]methyl}-2,6-dimethylmorpholine (210 mg, 0.573 mmol) (may be prepared as described for Compound 55) in dry N,N-dimethylformamide (DMF) (3 ml) for 30 minutes, then Zn(CN)$_2$ (37.0 mg, 0.315 mmol), tris(dibenzlideneacetone)dipalladium(0) (15.8 mg, 0.017 mmol) and 1,1'-bis(diphenylphosphino)ferrocene) (19.1 mg, 0.034 mmol) were added and the resulting brown solution stirred at 120° C. under argon for 1 hour. Zn(CN)$_2$ (37.0 mg, 0.315 mmol) and 1,1'-bis(diphenylphosphino)ferrocene) (19.1 mg, 0.034 mmol) were added and the reaction mixture stirred at 120° C. for 2 hours then 153° C. for one hour. The reaction mixture was cooled then partitioned between DCM (100 ml) and water (100 ml). The aqueous layer was extracted with DCM (2×50 ml), and then the combined organic layers were dried over MgSO$_4$, filtered and concentrated. The residue was purified by MDAP. Relevant fractions were combined. The residue was dissolved in MeOH and loaded onto an SCX cartridge, washed with MeOH and eluted with methanolic ammonia. Relevant fractions were combined and concentrated. The compound was dissolved in 1 ml of MeOH and 0.15 ml of 1N HCl in ether was added. Solvent was removed and residue dried over the weekend in a vacuum oven to afford the title compound as a grey solid (50 mg).

MS ES+ve m/z 313 (M+H)

$^1$H NMR (400 MHz, METHANOL-d$_4$) δ ppm 1.22 (m, J=6.4 Hz, 6H) 2.19 (s, 3H) 2.69-2.84 (m, 2H) 3.61 (d, J=11.6 Hz, 2H) 3.84-3.99 (m, 2H) 4.64 (s, 2H) 7.74 (d, J=8.3 Hz, 1H) 7.88 (dd, J=8.3, 1.3 Hz, 1H) 7.98 (s, 1H)

Compound 28: (3R)-3-Methyl-4-({1-[4-(trifluoromethyl)phenyl]-1H-tetrazol-5-yl}methyl)morpholine hydrochloride

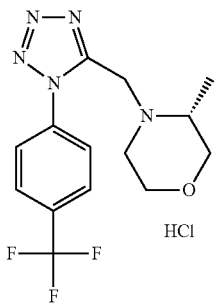

To a solution of (3R)-3-methylmorpholine hydrochloride (122 mg, 0.887 mmol, Tyger Scientific, Ewing, USA) and triethylamine (0.124 mL, 0.887 mmol) in methanol (2 mL) was added formaldehyde (37% aqueous) (0.066 mL, 0.887 mmol). The reaction mixture was stirred at room temperature for 2 hours before the addition of 4-(trifluoromethyl)phenyl isocyanide (152 mg, 0.887 mmol) and trimethylsilylazide (0.118 mL, 0.887 mmol). The reaction mixture was stirred at room temperature overnight (approximately 18 hours) and the solvent removed under vacuum. The residue was purified by MDAP. Fractions containing the desired compound were combined and the solvent removed. The residue was partitioned between saturated NaHCO$_3$ (2 mL) and DCM (5 ml). The organic layer was collected via a hydrophobic frit and the solvent removed under a stream of argon. The compound was dissolved in a minimum of diethyl ether before the addition of 1N HCl in diethyl ether (2 mL) leading to precipitation. The ether was decanted and the precipitate dried under vacuum to yield the title compound as a pale yellow solid (105 mg).

MS ES+ve m/z 328 (M+H)

$^1$H NMR (400 MHz, METHANOL-d$_4$) δ ppm 1.35 (d, J=6.1 Hz, 3H) 3.25-3.30 (m, peak overlaps with solvent, assume 1H) 3.56-3.72 (m, 3H) 3.81-3.90 (m, 1H) 3.93-4.03 (m, 2H) 4.76 (d, J=16.0 Hz, 1H) 5.06 (d, J=15.8 Hz, 1H) 7.93 (d, J=8.3 Hz, 2H) 8.04 (d, J=8.6 Hz, 2H)

Compound 29: 3,3-Dimethyl-4-({1-[3-(trifluoromethyl)phenyl]-1H-tetrazol-5-yl}methyl)morpholine

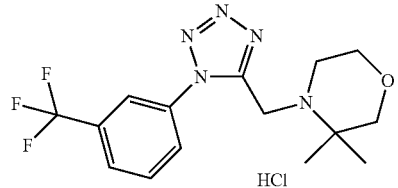 [SMILES: CC1(C)COCCN1Cc1nnnn1-c1cccc(C(F)(F)F)c1 ; Cl]

To a solution of 5-(chloromethyl)-1-[3-(trifluoromethyl)phenyl]-1H-tetrazole (80 mg, 0.305 mmol, commercially available from Otava, Kiev, Ukraine) in acetonitrile (2 mL) was added 3,3-dimethylmorpholine (46.2 mg, 0.305 mmol, commercially available, for example from Otava, Kiev, Ukraine or Tyger Scientific, Ewing, USA) and triethylamine (0.127 mL, 0.914 mmol). The reaction mixture was then heated to 120° C. for 50 min in a microwave reactor. The reaction mixture was concentrated in vacuo and the crude product was purified by MDAP. The relevant fractions were combined and concentrated in vacuo. The product was dissolved in DCM and 1N HCl in ether (110 uL) was added. The mixture was concentrated in vacuo, triturated with ether, then dried in vacuo to yield the title compound (white crystals, 40 mg).

MS ES+ve m/z 342 (M+H)

$^1$H NMR (400 MHz, METHANOL-d$_4$) δ ppm 1.39 (br. s., 6H) 3.71 (br. s., 4H) 3.97 (br. s., 2H) 4.75 (br. s., 2H) 7.94 (t, J=7.9 Hz, 1H) 8.00-8.08 (m, 2H) 8.16 (s, 1H)

Compound 30: 4-(5-{[cis-2,6-Dimethyl-4-morpholinyl]methyl}-1H-tetrazol-1-yl)-2-(trifluoromethyl)benzonitrile

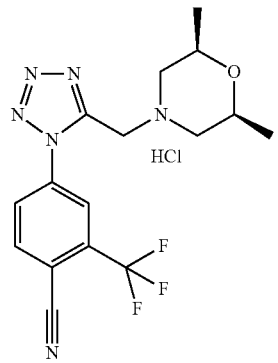 [SMILES: C[C@@H]1CN(Cc2nnnn2-c2ccc(C#N)c(C(F)(F)F)c2)C[C@H](C)O1 ; Cl]

To a solution of formaldehyde (37% in water) (0.114 ml, 1.53 mmol) in methanol (4 ml) was added cis-2,6-dimethylmorpholine (0.188 ml, 1.53 mmol, Alfa Aesar, Ward Hill, USA). The reaction mixture was stirred at room temperature for 2 hours before the addition of trimethylsilylazide (0.203 ml, 1.53 mmol) and 4-isocyano-2-(trifluoromethyl)benzonitrile (300 mg, 1.53 mmol, commercially available from Priaxon, Munich, Germany). The reaction mixture was stirred at room temperature for 18 hours. The reaction mixture was partitioned between DCM (50 ml) and water (20 ml). The aqueous layer was extracted with DCM (50 ml). The organic layers were combined, dried over MgSO$_4$, filtered and concentrated. The crude product was purified by flash chromatography (Biotage SP4) using Hexane:EtOAc as an eluant. Relevant fractions were combined and concentrated. This residue was dissolved in MeOH and loaded onto a 5 g SCX cartridge. The cartridge was washed with MeOH and eluted with methanolic ammonia. Relevant fractions were combined and concentrated and the product was left to dry in a vacuum oven overnight. The product was dissolved in 3 ml of DCM and 0.819 ml of 1M HCl in ether was added. The solvent was removed to afford the title compound as a pale yellow solid (340 mg).

MS ES+ve m/z 367 (M+H)

$^1$H NMR (400 MHz, METHANOL-d$_4$) δ ppm 1.24 (d, J=6.4 Hz, 6H) 2.87 (t, J=11.5 Hz, 2H) 3.69 (d, J=11.8 Hz, 2H) 3.90-4.02 (m, 2H) 4.91 (s, 2H) 8.19 (dd, J=8.3, 2.2 Hz, 1H) 8.34 (d, J=1.8 Hz, 1H) 8.37 (d, J=8.3 Hz, 1H)

Compound 31: 1-Methyl-4-({1-[4-(trifluoromethyl)phenyl]-1H-tetrazol-5-yl}methyl)piperazine dihydrochloride

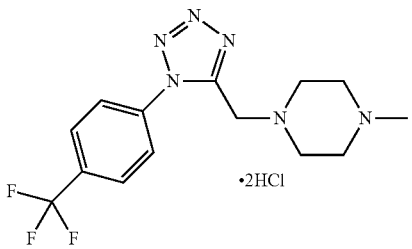 [SMILES: CN1CCN(Cc2nnnn2-c2ccc(C(F)(F)F)cc2)CC1]

To a solution of formaldehyde (0.022 mL, 0.292 mmol) in methanol (2 mL) was added 1-methylpiperazine (0.032 mL, 0.292 mmol). The reaction mixture was stirred at room temperature for 1 h before the addition of 4-(trifluoromethyl)phenylisocyanide (50 mg, 0.292 mmol, Fluorochem, Old Glossop, UK) and trimethylsilyl azide (0.046 mL, 0.351 mmol). The resulting reaction mixture was stirred at room temperature overnight.

The reaction mixture was diluted with DCM (10 mL) and washed with water (5 mL). The aqueous phase was washed with DCM (2×10 mL) and all of the organic phases were combined and concentrated in vacuo. The crude product was dissolved in methanol and poured onto a 1 g SCX cartridge. The cartridge was washed with methanol (2 column volumes) and eluted with 2N NH$_3$ in methanol (2 column volumes). The ammonia in methanol fractions were combined and concentrated in vacuo. The product was further purified by high pH MDAP. The relevant fractions were combined, concentrated and dried in vacuo. The product was dissolved in DCM and 1N HCl diethyl ether (0.33 mL) was added. The mixture was concentrated and the product dried in vacuo to yield the title compound as white crystals (63 mg)

MS ES+ve m/z 327 (M+H)

$^1$H NMR (400 MHz, DMSO-d$_6$) δ ppm 2.71 (s, 3H) 2.14-2.83 (m, 2H) 2.91-3.01 (m, 2H) 3.05 (d, J=12.7 Hz, 2H) 3.36 (d, J=12.1 Hz, 2H) 4.11 (s, 2H) 8.07 (s, 4H) 11.14 (br. s., 1H)

Compound 32: 3-Methyl-4-({1-[3-(trifluoromethyl)phenyl]-1H-tetrazol-5-yl}methyl)-2-piperazinone

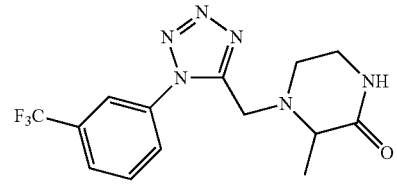 [SMILES: CC1C(=O)NCCN1Cc1nnnn1-c1cccc(C(F)(F)F)c1]

To a solution of 5-(chloromethyl)-1-[3-(trifluoromethyl)phenyl]-1H-tetrazole (200 mg, 0.762 mmol, commercially available from Otava, Kiev, Ukraine) in acetonitrile (3 mL) was added triethylamine (0.318 mL, 2.285 mmol) and 3-methyl-2-piperazinone (87 mg, 0.762 mmol, Sigma-Aldrich). The reaction mixture was heated to 120° C. for 20 min in a microwave reactor. The reaction mixture was concentrated in vacuo. The crude product was purified by silica chromatography (Biotage SP4), eluting with an increasing gradient of (2N NH$_3$ in MeOH) in DCM. The relevant fractions were combined and concentrate to give the title compound as white crystals (151 mg)

MS ES+ve m/z 341 (M+H)

$^1$H NMR (400 MHz, METHANOL-d$_4$) δ ppm 1.18 (d, J=7.0 Hz, 3H) 2.55-2.63 (m, 1H) 2.85-2.92 (m, 1H) 3.06-3.13 (m, 1H) 3.13-3.21 (m, 2H) 4.01 (d, J=14.7 Hz, 1H) 4.24 (d, J=14.7 Hz, 1H) 7.86 (m, 1H) 7.97 (d, J=8.1 Hz, 1H) 8.00 (d, J=7.9 Hz, 1H) 8.17 (s, 1H)

Compound 33: 1,3-Dimethyl-4-({1-[3-(trifluoromethyl)phenyl]-1H-tetrazol-5-yl}methyl)-2-piperazinone

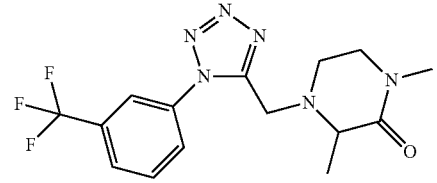 [SMILES: CC1C(=O)N(C)CCN1Cc1nnnn1-c1cccc(C(F)(F)F)c1]

To a solution of 3-methyl-4-({1-[3-(trifluoromethyl)phenyl]-1H-tetrazol-5-yl}methyl)-2-piperazinone (100 mg, 0.294 mmol, Compound 32), in N,N-Dimethylformamide (DMF) (1.5 mL) was added sodium hydride (25.9 mg, 0.646 mmol). After stirring for 1 hour under argon, iodomethane (0.020 mL, 0.323 mmol) was added. The resulting reaction mixture was stirred under argon for 1 hour.

The reaction mixture was diluted with ethyl acetate (20 mL) and washed with 2N NaOH solution (10 mL). The aqueous phase was washed with ethyl acetate (2×10 mL). The organic layers were combined and concentrated in vacuo. The crude product was purified by high pH MDAP. The relevant fractions were combined and concentrated in vacuo. The product was poured onto a SCX cartridge (0.5 g), washed with methanol (2 column volumes) and eluted with 2N ammonia in methanol (2 column volumes). The ammonia in methanol fractions were concentrated in vacuo to yield the title compound as light yellow oil (30 mg).

MS ES+ve m/z 355 (M+H)

¹H NMR (400 MHz, METHANOL-d₄) δ ppm 1.18 (d, J=6.8 Hz, 3H) 2.58-2.68 (m, 1H) 2.88 (s, 3H) 2.95 (m, 1H) 3.14-3.24 (m, 3H) 4.00 (d, J=14.7 Hz, 1H) 4.21 (d, J=14.7 Hz, 1H) 7.82-7.89 (m, 1H) 7.96 (d, J=7.9 Hz, 1H) 8.00 (d, J=7.9 Hz, 1H) 8.17 (s, 1H)

Compound 34: 4-[5-(4-Morpholinylmethyl)-1H-tetrazol-1-yl]-2-(trifluoromethyl)benzonitrile hydrochloride

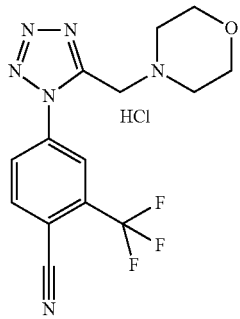 [SMILES: N#Cc1ccc(-n2nnnc2CN2CCOCC2)cc1C(F)(F)F ; Cl]

To a solution of formaldehyde (37% in water) (0.076 ml, 1.02 mmol) in methanol (3 ml) was added morpholine (0.089 ml, 1.02 mmol). The reaction mixture was stirred at room temperature for 2 hours before the addition of trimethylsilylazide (0.135 ml, 1.02 mmol) and 4-isocyano-2-(trifluoromethyl)benzonitrile (200 mg, 1.020 mmol, commercially available from Priaxon AG, Munich, Germany). The reaction mixture was stirred at room temperature for 18 hours. The reaction mixture was partitioned between DCM (50 ml) and water (20 ml). The aqueous layer was extracted with DCM (50 ml). The organic layers were combined, dried over MgSO₄, filtered and concentrated. The crude product was purified by reverse phase chromatography (Biotage SP4). Relevant fractions were combined and concentrated. The product was dissolved in 3 ml of DCM and 0.473 ml of 1M HCl in ether was added. Solvent was removed to afford the title compound as a white solid (175 mg)

MS ES+ve m/z 339 (M+H)

¹H NMR (400 MHz, METHANOL-d₄) δ ppm 3.43-3.55 (br. m, 4H) 3.92-4.00 (br. m., 4H) 4.90 (s, 2H) 8.21 (dd, 1H) 8.33-8.40 (m, 2H)

Compound 35: 3-Methyl-1-(1-methylethyl)-4-({1-[3-(trifluoromethyl)phenyl]-1H-tetrazol-5-yl}methyl)-2-piperazinone

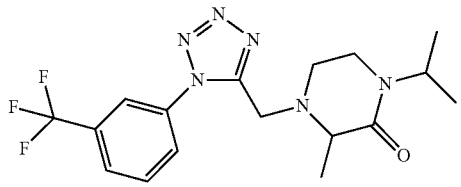 [SMILES: CC1C(=O)N(C(C)C)CCN1Cc1nnnn1-c1cccc(C(F)(F)F)c1]

To a solution of 3-methyl-4-({1-[3-(trifluoromethyl)phenyl]-1H-tetrazol-5-yl}methyl)-2-piperazinone (75 mg, 0.220 mmol, Compound 32), in N,N-Dimethylformamide (DMF) (1 mL) was added 2-iodopropane (0.024 mL, 0.242 mmol) and sodium hydride (8.81 mg, 0.220 mmol). The resulting reaction mixture was stirred at room temperature for 24 hours. To the reaction mixture was added 1 equivalent of 2-iodopropane and 0.5 equivalent of sodium hydride and stirred for an additional 24 h at room temperature. The reaction mixture was diluted with ethyl acetate (20 mL) and washed with 2N NaOH solution (10 mL). The aqueous phase was extracted with ethyl acetate (2×10 mL). All of the organic phases were combined, dried over magnesium sulphate, filtered and concentrated. The crude product was purified by MDAP. The relevant fractions were combined, concentrated and dried to give the title compound as a colourless oil (8 mg).

MS ES+ve m/z 383 (M+H)

¹H NMR (400 MHz, METHANOL-d₄) δ ppm 1.08 (d, J=6.8 Hz, 6H) 1.15 (d, J=6.8 Hz, 3H) 2.51-2.60 (m, 1H) 2.87-2.94 (m, 1H) 3.00-3.07 (m, 1H) 3.13 (m, 2H) 3.97 (d, J=14.7 Hz, 1H) 4.22 (d, J=14.7 Hz, 1H) 4.56-4.67 (m, 1H) 7.82-7.88 (m, 1H) 7.94-8.01 (d, 2H) 8.18 (s, 1H)

Compound 36: 4-({1-[3-(Trifluoromethyl)phenyl]-1H-tetrazol-5-yl}methyl)-2-piperazinone

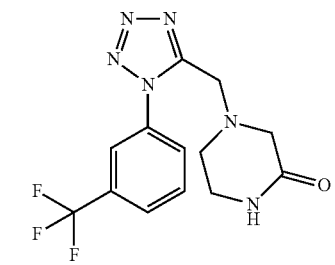 [SMILES: O=C1CN(Cc2nnnn2-c2cccc(C(F)(F)F)c2)CCN1]

To a solution of 5-(chloromethyl)-1-[3-(trifluoromethyl)phenyl]-1H-tetrazole (400 mg, 1.52 mmol, commercially available from Otava, Kiev, Ukraine) in acetonitrile (5 mL) was added triethylamine (0.637 mL, 4.57 mmol) and 2-piperazinone (168 mg, 1.675 mmol, Sigma-Aldrich). The reaction mixture was heated to 120° C. for 20 min in a microwave reactor.

The reaction mixture was concentrated in vacuo and the crude product was purified by reverse phase chromatography (Biotage SP4). The relevant fractions were combined and concentrated in vacuo to yield the title compound as white crystals (240 mg)

MS ES+ve m/z 327 (M+H)

¹H NMR (400 MHz, METHANOL-d₄) δ ppm 2.73-2.78 (m, 2H) 3.18 (s, 2H) 3.19-3.23 (m, 2H) 4.01 (s, 2H) 7.86 (t, J=8.1 Hz, 1H) 7.96 (d, J=7.9 Hz, 1H) 8.04 (d, J=7.9 Hz, 1H) 8.24 (s, 1H)

Compound 37: 4-(5-{[(cis)-2,5-Dimethyl-1-pyrrolidinyl]methyl}-1H-tetrazol-1-yl)benzonitrile

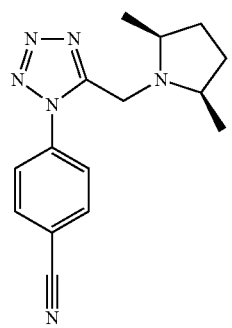 [SMILES: C[C@@H]1CC[C@H](C)N1Cc1nnnn1-c1ccc(C#N)cc1]

A solution of 2,5-dimethylpyrrolidine (0.334 mL, 2.73 mmol) and 4-[5-(chloromethyl)-1H-tetrazol-1-yl]benzonitrile (200 mg, 0.911 mmol, Intermediate 10) in acetonitrile (1.5 mL) was heated to 150° C. for 45 minutes in a microwave reactor. The reaction mixture was purified by high PH MDAP (2 injections). Relevant fractions were combined and the solvent removed. The resulting solid was partitioned between DCM (10 mL) and water (5 mL). The organic layer was collected via a hydrophobic frit and the solvent removed under vacuum to yield the title compound as a white solid (125 mg).

MS ES+ve m/z 283 (M+H)

$^1$H NMR (400 MHz, CHLOROFORM-d) δ ppm 0.81 (d, 6H) 1.35-1.45 (m, 2H) 1.85-1.95 (m, 2H) 2.83 (m, 2H) 4.00 (s, 2H) 7.87 (d, J=8.8 Hz, 2H) 8.14 (d, J=8.8 Hz, 2H)

Compound 38: 4-({1-[5-(Trifluoromethyl)-2-pyridinyl]-1H-tetrazol-5-yl}methyl)morpholine

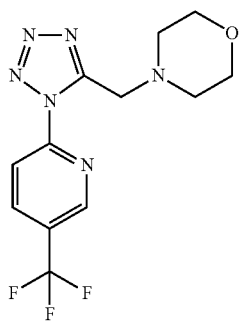

To a solution of formaldehyde (37% in water) (0.043 ml, 0.581 mmol) in methanol (2 ml) was added morpholine (0.051 ml, 0.581 mmol). The reaction mixture was stirred at room temperature for 2 hours before the addition of trimethylsilylazide (0.077 ml, 0.581 mmol) and 2-isocyano-5-(trifluoromethyl)pyridine (100 mg, 0.581 mmol, commercially available from Priaxon AG, Munich, Germany). The reaction mixture was stirred at room temperature for 18 hours. The reaction mixture was partitioned between DCM (50 ml) and water (20 ml). The aqueous layer was extracted with DCM (50 ml). The organic layers were combined and passed through a phase separator, then concentrated. The residue was purified by MDAP. Relevant fractions were combined to afford the title compound as a light yellow solid (7 mg).

MS ES+ve m/z 315 (M+H)

$^1$H NMR (400 MHz, METHANOL-d$_4$) δ ppm 2.56-2.64 (m, 4H) 3.50-3.62 (m, 4H) 4.33 (s, 2H) 8.25 (d, J=8.6 Hz, 1H) 8.48 (dd, J=8.6, 2.4 Hz, 1H) 8.99-9.02 (m, 1H)

Compound 39: (3S)-3-Methyl-4-({1-[4-(trifluoromethyl)phenyl]-1H-tetrazol-5-yl}methyl)morpholine hydrochloride

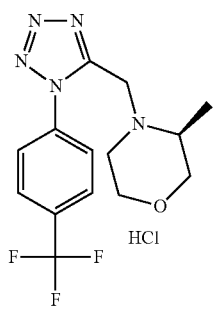

To a solution of (3S)-3-methylmorpholine (65.0 mg, 0.643 mmol, Tyger Scientific, Ewing, USA) in methanol (2 mL) was added formaldehyde (37% aqueous) (0.048 mL, 0.643 mmol). The reaction mixture was stirred at room temperature for 2 hours before the addition of 4-(trifluoromethyl)phenyl isocyanide (100 mg, 0.584 mmol) and trimethylsilylazide (0.078 mL, 0.584 mmol). The reaction mixture was stirred at room temperature overnight (approximately 18 hours) and the solvent removed under vacuum. The residue was purified by MDAP. Fractions containing the desired compound were combined and the solvent removed. The residue was partitioned between saturated NaHCO$_3$ (2 mL) and DCM (5 ml). The organic layer was collected via a hydrophobic frit and the solvent removed under a stream of argon. The compound was dissolved in a minimum of diethyl ether and methanol before the addition of 1N HCl in diethyl ether (2 mL). The solvent was removed under a stream of argon and the residue dried under vacuum to yield the title compound as a white solid (70 mg).

MS ES+ve m/z 328 (M+H)

$^1$H NMR (400 MHz, METHANOL-d$_4$) δ ppm 1.38 (d, J=6.6 Hz, 3H) 3.34-3.42 (m, 1H) 3.62-3.71 (m, 2H) 3.71-3.79 (m, 1H) 3.85-3.94 (m, 1H) 3.95-4.05 (m, 2H) 4.82 (d, J=16.0 Hz, 1H) 5.10 (d, J=16.0 Hz, 1H) 7.93 (d, J=8.3 Hz, 2H) 8.05 (d, J=8.6 Hz, 2H)

Compound 40: 4-(1-{1-[4-(Trifluoromethyl)phenyl]-1H-tetrazol-5-yl}ethyl)morpholine

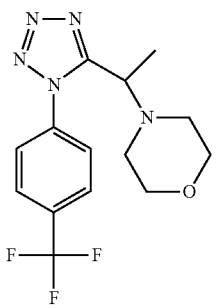 [SMILES: CC(c1nnnn1-c1ccc(C(F)(F)F)cc1)N1CCOCC1]

To a solution of acetaldehyde (0.198 mL, 3.51 mmol) in methanol (4 mL) was added morpholine (0.265 mL, 3.04 mmol) and 4-(trifluoromethyl)phenyl isocyanide (400 mg, 2.34 mmol, Fluorochem, Old Glossop, UK). The reaction mixture was shaken at room temperature for 18 hours. The solvent was removed from the reaction mixture to yield a dark brown gum. The reaction mixture was purified by silica chromatography (Biotage SP4, eluting 20% EtOAc in iso-hexane (5 column volumes) then a gradient from 20-35% EtOAc in iso-hexane (over 10 column volumes)). Fractions containing the product were combined and the solvent removed to yield an orange gum. The compound was triturated with diethyl ether (2×1 mL) then dried under vacuum to yield the title compound as a solid (29 mg).

MS ES+ve m/z 328 (M+H)

$^1$H NMR (400 MHz, CHLOROFORM-d) δ ppm 1.57 (d, J=2.6 Hz, 3H) 2.45-2.54 (m, 2H) 2.55-2.64 (m, 2H) 3.53-3.65 (m, 4H) 4.06 (q, 1H) 7.83-7.92 (m, 4H)

Compound 41: 4-(5-{[(3R)-3-Methyl-4-morpholinyl]methyl}-1H-tetrazol-1-yl)-2-(trifluoromethyl)benzonitrile

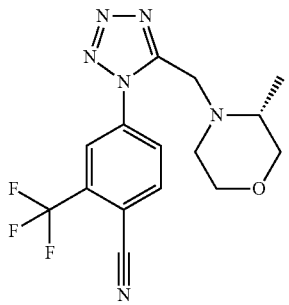 [SMILES: C[C@@H]1COCCN1Cc1nnnn1-c1ccc(C#N)c(C(F)(F)F)c1]

To a solution of (3R)-3-methylmorpholine (51.6 mg, 0.510 mmol, Tyger Scientific, Ewing, USA) in methanol (2 mL) was added formaldehyde (37% aqueous) (0.038 mL, 0.510 mmol). The reaction mixture was stirred at room temperature for 1 hour before the addition of 4-isocyano-2-(trifluoromethyl)benzonitrile (100 mg, 0.510 mmol, commercially available from Priaxon AG, Munich, Germany) and trimethylsilylazide (0.068 mL, 0.510 mmol). The reaction mixture was stirred at room temperature overnight (approximately 18 hours) and the solvent removed under vacuum. The residue was purified by MDAP. Fractions containing the desired compound were combined and the solvent removed. The residue was partitioned between saturated $NaHCO_3$ (2 mL) and DCM (5 ml). The organic layer was collected via a hydrophobic frit and the solvent removed under a stream of argon. The compound was dissolved in a minimum of diethyl ether before the addition of 1N HCl in diethyl ether (2 mL) leading to precipitation. The ether was removed under vacuum and the product further dried under vacuum at 40° C. overnight to yield the title compound as a white solid (57 mg).

MS ES-ve m/z 351 (M–H)

$^1$H NMR (400 MHz, METHANOL-$d_4$) δ ppm 1.35 (d, J=5.9 Hz, 3H) 3.18-3.27 (m, 1H) 3.51-3.67 (m, 3H) 3.78-3.88 (m, 1H) 3.92-4.02 (m, 2H) 4.73 (d, J=15.8 Hz, 1H) 5.05 (d, J=16.0 Hz, 1H) 8.21 (dd, J=8.3, 2.0 Hz, 1H) 8.37 (d, J=8.3 Hz, 1H) 8.39 (d, J=1.8 Hz, 1H)

Compound 42: (3R)-3-Methyl-4-({1-[5-(trifluoromethyl)-2-pyridinyl]-1H-tetrazol-5-yl}methyl)morpholine

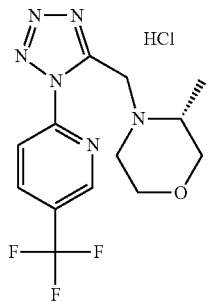

To a solution of (3R)-3-methylmorpholine (88 mg, 0.872 mmol, Tyger Scientific, Ewing, USA) in methanol (2 mL) was added formaldehyde (37% aqueous) (0.065 mL, 0.872 mmol). The reaction mixture was stirred at room temperature for 2 hours before the addition of 2-isocyano-5-(trifluoromethyl)pyridine (150 mg, 0.872 mmol, commercially available from Priaxon AG, Munich, Germany) and trimethylsilylazide (0.116 mL, 0.872 mmol). The reaction mixture was stirred at room temperature overnight (approximately 18 hours) and the solvent removed under vacuum. The residue was purified by MDAP. Fractions containing the desired compound were combined and the solvent removed. The residue was partitioned between saturated $NaHCO_3$ (2 mL) and DCM (5 ml). The organic layer was collected via a hydrophobic frit and the solvent removed under a stream of argon to yield a colourless gum. The compound was dissolved in a minimum of diethyl ether and methanol before the addition of 1N HCl in diethyl ether (2 mL) The solvent was removed under a stream of argon and the residue dried under vacuum at 40° C. for 18 hours to yield a white solid. The compound was triturated with diethyl ether (0.5 mL) and the solvent decanted. The solid was dried under vacuum at 40° C. for 18 hours to yield the title compound as a white solid (11 mg)

MS ES+ve m/z 329 (M+H)

$^1$H NMR (400 MHz, METHANOL-$d_4$) δ ppm 1.52 (d, J=6.6 Hz, 3H) 3.46-3.56 (m, 1H) 3.65-3.79 (m, 1H) 3.79-3.98 (m, 3H) 3.99-4.10 (m, 2H) 5.21 (d, J=16.0 Hz, 1H) 5.53 (br. s., 1H) 8.43 (d, J=8.6 Hz, 1H) 8.56 (dd, J=8.8, 2.0 Hz, 1H) 9.05 (s, 1H)

Compound 43: (1S,4S)-5-({1-[4-(Trifluoromethyl)phenyl]-1H-tetrazol-5-yl}methyl)-2-oxa-5-azabicyclo[2.2.1]heptane hydrochloride

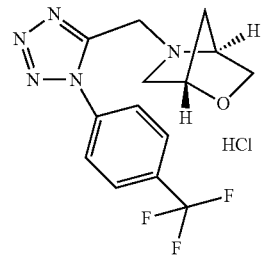 [SMILES: FC(F)(F)c1ccc(-n2nnnc2CN2C[C@@H]3C[C@H]2CO3)cc1 ; Cl]

To a solution of formaldehyde (37% in water) (0.087 ml, 1.17 mmol) in methanol (4 ml) was added (1S,4S)-2-oxa-5-azabicyclo[2.2.1]heptane (116 mg, 1.17 mmol, commercially available for example from InterChim, Montlucon, France). The reaction mixture was stirred at room temperature for 2 hours before the addition of trimethylsilylazide (0.155 ml, 1.17 mmol) and 4-(trifluoromethyl)phenyl isocyanide (200 mg, 1.17 mmol, Fluorochem, Old Glossop, UK). The reaction mixture was stirred at room temperature over the weekend. The reaction mixture was partitioned between DCM (50 ml) and water (20 ml). The aqueous layer was extracted with DCM (50 ml). The organic layers were combined and passed through a phase separator, then concentrated to afford a green oil. The residue was purified by MDAP. Relevant fractions were combined and the solvent removed. The compound was dissolved in 1 ml of DCM and 0.11 ml of 1M HCl in ether was added. The solvent was removed under vacuum to afford the title compound as a white solid (43 mg).

MS ES+ve m/z 326 (M+H)

$^1$H NMR (400 MHz, METHANOL-$d_4$) δ ppm 2.25 (m, J=11.4 Hz, 1H) 2.36 (d, J=11.4 Hz, 1H) 3.59 (br. s., 1H) 3.79 (br. s., 1H) 3.92 (d, J=9.9 Hz, 1H) 4.24 (d, J=10.3 Hz, 1H)

4.74 (br. s., 2H) 4.99 (d, J=16.2 Hz, 1H) 5.07 (d, J=16.2 Hz, 1H) 7.92 (d, 2H) 8.04 (d, J=8.3 Hz, 2H)

Compound 44: 4-{5-[(1S,4S)-2-Oxa-5-azabicyclo[2.2.1]hept-5-ylmethyl]-1H-tetrazol-1-yl}-2-(trifluoromethyl)benzonitrile

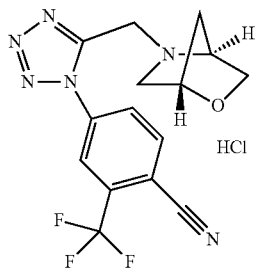

To a solution of formaldehyde (37% in water) (0.076 ml, 1.02 mmol) in methanol (4 ml) was added (1S,4S)-2-oxa-5-azabicyclo[2.2.1]heptane (101 mg, 1.02 mmol, commercially available for example from InterChim, Montlucon, France). The reaction mixture was stirred at room temperature for 2 hours before the addition of trimethylsilylazide (0.135 ml, 1.02 mmol) and 4-isocyano-2-(trifluoromethyl)benzonitrile (200 mg, 1.020 mmol, commercially available, for example from Priaxon, Munich, Germany). The reaction mixture was stirred at room temperature for 18 hours. The reaction mixture was partitioned between DCM (50 ml) and water (20 ml). The aqueous layer was extracted with DCM (50 ml). The organic layers were combined, passed through a phase separator and concentrated. The residue was purified by MDAP. Relevant fractions were combined and the solvent removed. The compound was dissolved in 2 ml of DCM and 0.163 ml of 1M HCl in water was added. The solvent was removed to afford the title compound as a white solid (63 mg).

MS ES+ve m/z 351 (M+H)

¹H NMR (400 MHz, METHANOL-d₄) δ ppm 2.27 (d, J=11.8 Hz, 1H) 2.38 (d, J=11.8 Hz, 1H) 3.60 (br. s., 1H) 3.79 (br. s., 1H) 3.93 (dd, J=10.3, 1.5 Hz, 1H) 4.26 (d, J=10.1 Hz, 1H) 4.76 (br. s., 2H) 5.05 (d, J=16.2 Hz, 1H) 5.13 (d, J=16.2 Hz, 1H) 8.18 (dd, J=8.3, 2.2 Hz, 1H) 8.32 (d, J=1.5 Hz, 1H) 8.36 (d, J=8.3 Hz, 1H)

Compound 45: 1,2,2-Trimethyl-4-({1-[3-(trifluoromethyl)phenyl]-1H-tetrazol-5-yl}methyl)piperazine hydrochloride

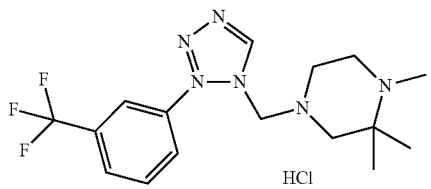

To a solution of 3,3-dimethyl-1-({1-[3-(trifluoromethyl)phenyl]-1H-tetrazol-5-yl}methyl)piperazine (120 mg, 0.353 mmol, Intermediate 12) in N,N-Dimethylformamide (DMF) (2 mL) was added iodomethane (0.024 mL, 0.388 mmol) and potassium carbonate (146 mg, 1.06 mmol). The resulting reaction mixture was stirred at room temperature for 5 hours.

The reaction mixture was diluted with ethyl acetate (20 mL) and washed with 2N NaOH (10 mL). The aqueous phase was separated and extracted with ethyl acetate (2×10 mL). All of the organic phases were combined, dried over magnesium sulphate, filtered and concentrated in vacuo. The crude product was purified by high pH MDAP. The relevant fractions were combined, concentrated and dried. The product was dissolved in DCM and 1N HCl in diethyl ether (192 uL) was added. The product was concentrated and dried in vacuo to yield the title compound as white crystals (76 mg)

MS ES+ve m/z 355 (M+H)

¹H NMR (400 MHz, METHANOL-d₄) δ ppm 1.13 (s, 3H) 1.35 (s, 3H) 2.49-2.56 (m, 1H) 2.60-2.69 (m, 1H) 2.74 (s, 3H) 2.78-2.86 (m, 1H) 2.96-3.03 (m, 1H) 3.07-3.18 (m, 1H) 3.23-3.28 (m, 1H) 4.06 (s, 2H) 7.86-7.92 (m, 1H) 7.98 (d, J=7.9 Hz, 1H) 8.04 (d, J=8.1 Hz, 1H) 8.14 (s, 1H)

Compound 46: 1-({1-[4-(Trifluoromethyl)phenyl]-1H-tetrazol-5-yl}methyl)piperazine

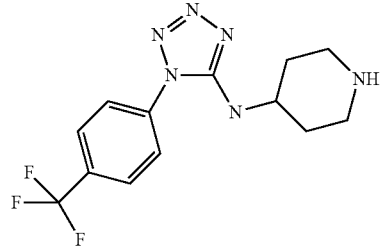 [SMILES: FC(F)(F)c1ccc(-n2nnnc2NC2CCNCC2)cc1]

To a solution of 1,1-dimethylethyl 4-({1-[4-(trifluoromethyl)phenyl]-1H-tetrazol-5-yl}methyl)-1-piperazinecarboxylate (613 mg, 1.486 mmol, Intermediate 15) in methanol was added 4M hydrogen chloride in 1,4-dioxane (10 mL, 40 mmol). The reaction mixture was stirred at room temperature for 1 hour.

The reaction mixture was concentrated in vacuo. The residue was dissolved in water/MeOH and poured onto a 5 g SCX cartridge, washed with MeOH (2 column volumes) and eluted with ammonia in MeOH (2 column volumes). The ammonia in MeOH fractions were concentrated and dried in vacuo to yield the title compound as white crystals (431 mg).

MS ES+ve m/z 313 (M+H)

¹H NMR (400 MHz, METHANOL-d₄) δ ppm 2.45-2.52 (m, 4H) 2.67-2.78 (m, 4H) 3.89 (s, 2H) 7.97 (d, J=9.0 Hz, 2H) 8.01 (d, J=8.8 Hz, 2H)

Compound 47: 1-(Ethylsulfonyl)-4-({1-[4-(trifluoromethyl)phenyl]-1H-tetrazol-5-yl}methyl)piperazine

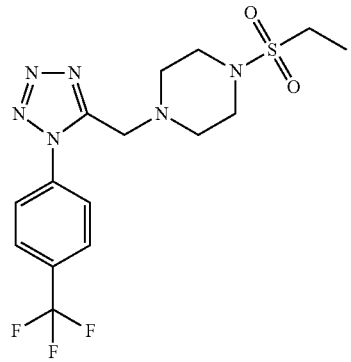 [SMILES: CCS(=O)(=O)N1CCN(Cc2nnnn2-c2ccc(C(F)(F)F)cc2)CC1]

5-(Chloromethyl)-1-[4-(trifluoromethyl)phenyl]-1H-tetrazole (79 mg, 0.301 mmol, commercially available from UkrOrgSynthesis, Kiev, Ukraine) and 1-(ethylsulfonyl)piperazine (53.6 mg, 0.301 mmol, Sigma-Aldrich) were dissolved in acetonitrile (1.5 ml). Triethylamine (0.046 ml, 0.331 mmol) was added, and the mixture was heated at 120° C. in a microwave with stirring for 20 min. The reaction mixture was concentrated in vacuo and the residue was purified by high pH MDAP to yield the title compound as a colourless solid (89 mg).

MS ES+ve m/z 405 (M+H)

$^1$H NMR (400 MHz, CHLOROFORM-d) δ ppm 1.37 (t, 3H) 2.63-2.73 (m, 4H) 2.96 (q, J=7.4 Hz, 2H) 3.21-3.38 (m, 4H) 3.86 (s, 2H) 7.88 (d, J=5.8 Hz, 2H) 7.92 (d, J=8.8 Hz, 2H)

Compound 48: 1-(Ethylsulfonyl)-4-({1-[3-(trifluoromethyl)phenyl]-1H-tetrazol-5-yl}methyl)piperazine

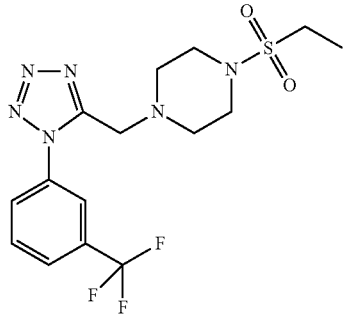 [SMILES: CCS(=O)(=O)N1CCN(Cc2nnnn2-c2cccc(C(F)(F)F)c2)CC1]

5-(Chloromethyl)-1-[3-(trifluoromethyl)phenyl]-1H-tetrazole (79 mg, 0.301 mmol, commercially available from UkrOrgSynthesis, Kiev, Ukraine) and 1-(ethylsulfonyl)piperazine (53.6 mg, 0.301 mmol, Sigma-Aldrich) were dissolved in acetonitrile (1.5 ml). Triethylamine (0.046 ml, 0.331 mmol) was added, and the mixture was heated in a microwave with stirring at 120° C. for 20 min. The reaction mixture was concentrated in vacuo and the residue purified by high pH MDAP to yield the title compound as a colourless solid (70 mg).

MS ES+ve m/z 405 (M+H)

$^1$H NMR (400 MHz, CHLOROFORM-d) δ ppm 1.38 (t, 3H) 2.64-2.74 (m, 4H) 2.97 (q, J=7.5 Hz, 2H) 3.26-3.36 (m, 4H) 3.83 (s, 2H) 7.73-7.81 (m, 1H) 7.86 (d, J=7.9 Hz, 1H) 7.98 (d, J=8.1 Hz, 1H) 8.34 (s, 1H)

Compound 49: 4-(5-{[(2S)-2-(Trifluoromethyl)-1-pyrrolidinyl]methyl}-1H-tetrazol-1-yl)benzonitrile

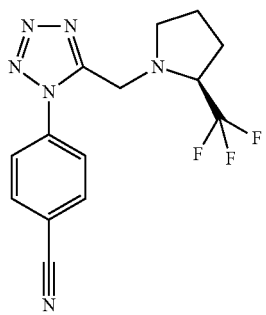 [SMILES: N#Cc1ccc(-n2nnnc2CN2CCC[C@H]2C(F)(F)F)cc1]

To a mixture of 4-[5-(chloromethyl)-1H-tetrazol-1-yl]benzonitrile (100 mg, 0.455 mmol, Intermediate 10) and polymer supported N-methylmorpholine (4 mmol/g, 171 mg, 0.683 mmol) in acetonitrile (3 mL) was added (2S)-2-(trifluoromethyl)pyrrolidine (95 mg, 0.683 mmol). The reaction mixture was heated at 120° C. for 20 min in a microwave reactor and at 140° C. for 20 min and at 150° C. for 30 min and finally at 160° C. for 30 min in the microwave reactor.

Solvent was removed under vacuum and the residue was purified by MDAP. Relevant fractions were combined and the solvent removed. The residue was dissolved in 1 ml of DCM and 0.192 ml of 1M HCl in ether was added. The solvent was removed to afford the title compound as a white solid (61 mg).

MS ES+ve m/z 323 (M+H)

$^1$H NMR (400 MHz, METHANOL-d$_4$) δ ppm 1.66-1.79 (m, 1H) 1.78-1.95 (m, 2H) 2.04-2.19 (m, 1H) 2.58-2.70 (m, 1H) 2.82-2.93 (m, 1H) 3.39-3.53 (m, 1H) 4.24 (d, J=14.5 Hz, 1H) 4.34 (d, J=14.5 Hz, 1H) 7.95 (d, J=8.8 Hz, 2H) 8.01 (d, J=8.8 Hz, 2H)

Compound 50: (1S,4S)-2-({1-[4-(Trifluoromethyl)phenyl]-1H-tetrazol-5-yl}methyl)-2,5-diazabicyclo[2.2.1]heptane

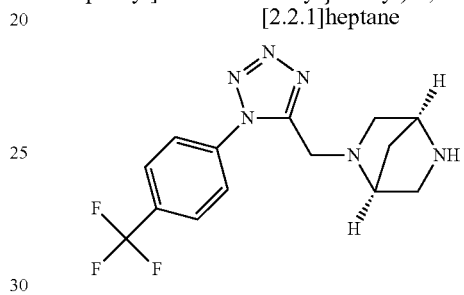

To a solution of 1,1-dimethylethyl (1S,4S)-5-({1-[4-(trifluoromethyl)phenyl]-1H-tetrazol-5-yl}methyl)-2,5-diazabicyclo[2.2.1]heptane-2-carboxylate (470 mg, 1.107 mmol, Intermediate 17) in methanol was added 4M hydrogen chloride in 1,4-dioxane (5 mL, 20 mmol). The reaction mixture was stirred at room temperature for 2 hours. The reaction mixture was concentrated in vacuo and poured onto a 5 g SCX cartridge. The cartridge was washed with methanol (2 column volumes) and eluted with ammonia in methanol (2 column volumes). The ammonia in methanol fractions were concentrated and the residue dried in vacuo to yield the title compound as white crystals (363 mg)

MS ES+ve m/z 325 (M+H)

$^1$H NMR (400 MHz, METHANOL-d$_4$) δ ppm 1.57 (d, J=10.1 Hz, 1H) 1.77 (d, J=9.9 Hz, 1H) 2.59 (dd, J=9.8, 1.0 Hz, 1H) 2.76 (dd, J=10.6, 2.3 Hz, 1H) 2.85 (dd, J=9.9, 2.4 Hz, 1H) 3.01 (dd, J=10.5, 1.1 Hz, 1H) 3.40 (s, 1H) 3.56 (s, 1H) 4.06 (d, J=14.3 Hz, 1H) 4.16 (d, J=14.3 Hz, 1H) 7.97 (d, J=8.6 Hz, 2H) 8.03 (d, J=8.6 Hz, 2H)

Compound 51: (1S,4S)-2-(1-Methylethyl)-5-({1-[4-(trifluoromethyl)phenyl]-1H-tetrazol-5-yl}methyl)-2,5-diazabicyclo[2.2.1]heptane hydrochloride

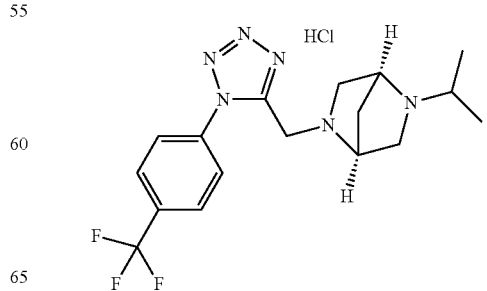

To a solution of (1S,4S)-2-({1-[4-(trifluoromethyl)phenyl]-1H-tetrazol-5-yl}methyl)-2,5-diazabicyclo[2.2.1]heptane (100 mg, 0.308 mmol, compound 50) in tetrahydrofuran (THF) (2 mL) was added acetone (0.045 mL, 0.617 mmol) and acetic acid (1.765 μL, 0.031 mmol). To the reaction mixture was added, after 3 hours, sodium triacetoxyborohydride (131 mg, 0.617 mmol) and the reaction mixture was stirred at room temperature overnight.

The reaction mixture was diluted with ethyl acetate (20 mL) and washed with 2N NaOH (10 mL). The aqueous phase was extracted with ethyl acetate (2×10 mL) and all of the organic phases were combined, dried over magnesium sulphate, filtered and concentrated in vacuo. The crude product was purified by high pH MDAP. The relevant fractions were combined, concentrated and dried. The product was dissolved in DCM and 1N HCl in diethyl ether (179 uL) was added. The product was concentrated and dried in vacuo to yield the title compound as off white crystals (59 mg).

MS ES+ve m/z 367 (M+H)

$^1$H NMR (400 MHz, METHANOL-d$_4$) δ ppm 1.10 (d, J=6.4 Hz, 3H) 1.14 (d, J=6.1 Hz, 3H) 1.79 (d, J=10.5 Hz, 1H) 1.87 (d, J=10.3 Hz, 1H) 2.52-2.63 (m, 1H) 2.63-2.70 (m, 1H) 2.71-2.84 (m, 1H) 2.98 (d, J=10.7 Hz, 2H) 3.39 (br. s., 1H) 3.84 (br. s., 1H) 4.05 (d, J=14.5 Hz, 1H) 4.21 (d, J=14.5 Hz, 1H) 7.98 (d, J=9.0 Hz, 2H) 8.01 (d, J=9.0 Hz, 2H)

Compound 52: (3R)-1-Ethyl-3-methyl-4-({1-[4-(trifluoromethyl)phenyl]-1H-tetrazol-5-yl}methyl)-2-piperazinone

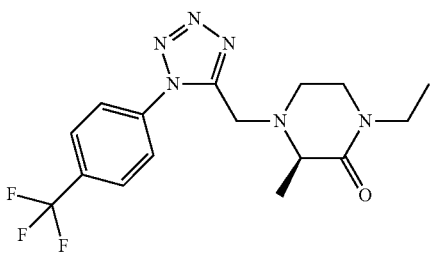

To a solution of (3R)-3-methyl-4-({1-[4-(trifluoromethyl)phenyl]-1H-tetrazol-5-yl}methyl)-2-piperazinone (100 mg, 0.294 mmol, intermediate 18), in N,N-Dimethylformamide (DMF) (1 mL) was added iodoethane (0.026 mL, 0.323 mmol) and sodium hydride (23.5 mg, 0.588 mmol). The resulting reaction mixture was stirred at room temperature for 24 hours.

The reaction mixture was diluted with ethyl acetate (20 mL) and washed with 2N NaOH (10 mL). The aqueous phase was extracted with ethyl acetate (2×10 mL) and all of the organic phases were combined, dried over magnesium sulphate, filtered and concentrated in vacuo to give an oil. The crude product was purified by high pH MDAP. The relevant fractions were combined, concentrated and dried to give the title compound as a colourless oil (63 mg)

MS ES+ve m/z 369 (M+H)

$^1$H NMR (400 MHz, CHLOROFORM-d) δ ppm 1.13 (t, 3H) 1.35 (d, J=6.8 Hz, 3H) 2.74 (dt, J=12.2, 5.8 Hz, 1H) 3.07 (dt, J=12.6, 5.1 Hz, 1H) 3.20-3.32 (m, 3H) 3.41 (q, J=7.2 Hz, 2H) 3.88 (d, J=13.8 Hz, 1H) 4.07 (d, J=13.8 Hz, 1H) 7.87 (d, J=8.8 Hz, 2H) 7.92 (d, J=8.6 Hz, 2H)

Compound 53: 4-{5-[(3,3-Dimethyl-4-morpholinyl)methyl]-1H-tetrazol-1-yl}benzonitrile

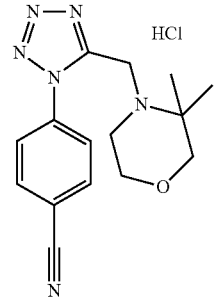 [SMILES: CC1(C)COCCN1Cc1nnnn1-c1ccc(C#N)cc1 ; Cl]

A solution of 3,3-dimethylmorpholine (49.7 mg, 0.328 mmol, commercially available, for example from Otava, Kiev, Ukraine or Tyger Scientific, Ewing, USA), 4-[5-(chloromethyl)-1H-tetrazol-1-yl]benzonitrile (60 mg, 0.273 mmol, may be prepared as described in Intermediate 10) and di-isopropylethylamine (0.110 mL, 0.628 mmol) in acetonitrile (0.7 mL) was heated to 120° C. for 30 minutes in a microwave reactor. The reaction mixture was allowed to cool and the solution purified by MDAP. Fractions containing the desired product were combined and the solvent removed. The residue was partitioned between saturated NaHCO$_3$ (aq, 2 mL) and DCM (5 mL). The organic layer was collected via a hydrophobic frit and the solvent removed under vacuum. The residue was dissolved in a minimum of dichloromethane before the addition of 1N HCl in diethyl ether (1 mL). The compound was partitioned between saturated NaHCO$_3$ (aq, 2 mL) and DCM (5 mL). The organic layer was collected via a hydrophobic frit and the solvent removed under vacuum. The crude product was further purified by silica chromatography (Biotage SP4, eluting 20% EtOAc in iso-hexane (3 column volumes) then a gradient from 20-60% EtOAc in iso-hexane (over 12 column volumes)) to yield a colourless gum. The residue was dissolved in a minimum of dichloromethane before the addition of 1N HCl in diethyl ether (1 mL). The solvent was removed under vacuum to yield a pale yellow solid which was triturated with methanol (0.5 mL) then dried under vacuum to yield the title compound as a white solid (22 mg).

MS ES+ve m/z 299 (M+H)

$^1$H NMR (400 MHz, METHANOL-d$_4$) δ ppm 1.41 (br. s., 6H) 3.67 (br. s., 2H) 3.71 (s, 2H) 3.96 (br. s., 2H) 4.80 (br. s., 2H) 7.95 (d, J=8.8 Hz, 2H) 8.10 (d, J=8.6 Hz, 2H)

Compound 54: (3R)-4-[(1-{4-[(Difluoromethyl)oxy]phenyl}-1H-tetrazol-5-yl)methyl]-3-methylmorpholine hydrochloride

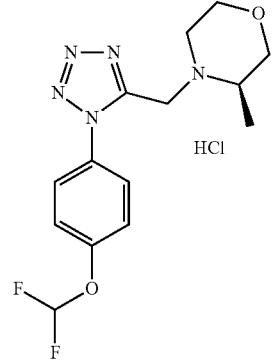 [SMILES: C[C@@H]1COCCN1Cc1nnnn1-c1ccc(OC(F)F)cc1 ; Cl]

To a solution of 5-(chloromethyl)-1-{4-[(difluoromethyl)oxy]phenyl}-1H-tetrazole (100 mg, 0.384 mmol, commercially available, for example from UkrOrgSynthesis, Kiev, Ukraine) in acetonitrile (2 mL) was added triethylamine (0.160 mL, 1.151 mmol) and (3R)-3-methylmorpholine (46.6 mg, 0.460 mmol, Tyger Scientific, Ewing, USA). The reaction mixture was heated for 20 min 120° C. in a microwave reactor.

The reaction mixture was concentrated in vacuo and the crude product was purified by MDAP. The relevant fractions were combined and concentrated in vacuo to give an oil. The product was dissolved in MeOH and 1N HCl (0.14 mL) was added. The mixture was concentrated and dried in vacuo to yield the title compound as a colourless oil (55 mg).

MS ES+ve m/z 326 (M+H)

$^1$H NMR (400 MHz, METHANOL-d$_4$) δ ppm 1.05 (d, J=5.5 Hz, 3H) 2.64-2.84 (m, 1H) 2.88-107 (m, 2H) 3.27-3.37 (m, integration obscured by solvent, assume 1H) 3.54-3.65 (m, 1H) 3.69-3.83 (m, 2H) 4.04-4.26 (m, 1H) 4.46-4.64 (m, 1H) 7.01 (t, J=73.2 Hz, 1H) 7.43 (d, J=9.0 Hz, 2H) 7.71-7.78 (m, 2H)

Compound 55: (cis)-4-{[1-(4-Bromo-2-methylphenyl)-1H-tetrazol-5-yl]methyl}-2,6-dimethylmorpholine hydrochloride

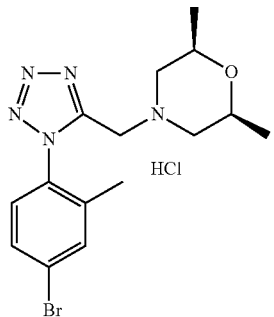 [SMILES: Cc1cc(Br)ccc1-n1nnnc1CN1C[C@@H](C)O[C@@H](C)C1 ; Cl]

To a solution of formaldehyde (37% in water) (0.076 ml, 1.02 mmol) in methanol (2 ml) was added cis-2,6-dimethylmorpholine (0.126 ml, 1.02 mmol, Alfa Aesar, Ward Hill, USA). The reaction mixture was stirred at room temperature for 2 hours before the addition of trimethylsilylazide (0.135 ml, 1.02 mmol, supplier) and 4-bromo-2-methylphenyl iso-cyanide (200 mg, 1.02 mmol, commercially available from Priaxon, Munich, Germany). The reaction mixture was stirred at room temperature for 67 hours. The reaction mixture was partitioned between DCM (50 ml) and water (20 ml). The aqueous layer was extracted with DCM (50 ml). The organic layers were combined, dried over MgSO$_4$, filtered and concentrated. The crude product was purified by MDAP. Relevant fractions were combined and concentrated. The residue was dissolved in MeOH and loaded onto an SCX cartridge. The cartridge was washed with methanol and eluted with methanolic ammonia. Relevant fractions were combined and concentrated. The residue was dissolved in 1 ml of DCM and 0.75 ml of 1M HCl in ether was added. Solvent was removed to afford the title compound as a white solid (265 mg)

MS ES+ve m/z 367 (M+H)

$^1$H NMR (400 MHz, METHANOL-d$_4$) δ ppm 1.23 (d, J=6.4 Hz, 6H) 2.10 (s, 3H) 2.81 (t, J=11.5 Hz, 2H) 3.65 (d, J=12.1 Hz, 2H) 3.88-3.99 (m, 2H) 4.66 (s, 2H) 7.40 (d, J=8.6 Hz, 1H) 7.68 (dd, J=8.3, 1.8 Hz, 1H) 7.80 (d, J=1.5 Hz, 1H)

The following compounds were prepared in a similar manner to that described for Compound 28, using the appropriate amine and aryl iso-cyanide:

| Compound No. | Structure | Name | Analytical data |
| --- | --- | --- | --- |
| 56 | 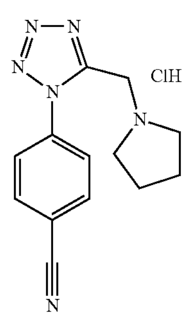 [SMILES: N#Cc1ccc(-n2nnnc2CN2CCCC2)cc1 ; Cl] | 4-[5-(1-Pyrrolidinylmethyl)-1H-tetrazol-1-yl)benzonitrile hydrochloride | MS ES + ve m/z 255 (M + H) |
| 57 | 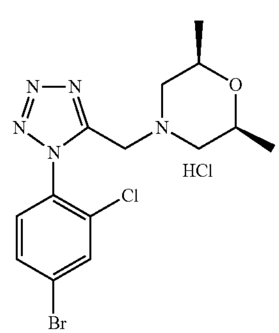 [SMILES: C[C@@H]1CN(Cc2nnnn2-c2ccc(Br)cc2Cl)C[C@H](C)O1 ; Cl] | cis-4-{[1-(4-Bromo-2-chlorophenyl)-1H-tetrazol-5-yl]methyl}-2,6-dimethylmorpholine hydrochloride | MS ES + ve m/z 388 (M + H) |

-continued

| Compound No. | Structure | Name | Analytical data |
|---|---|---|---|
| 58 | 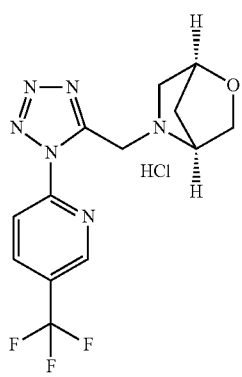 [SMILES: FC(F)(F)c1ccc(-n2nnnc2CN2C[C@@H]3C[C@H]2CO3)nc1 ; Cl] | (1S,4S)-5-({1-[5-(Trifluoromethyl)-2-pyridinyl]-1H-tetrazol-5-yl}methyl)-2-oxa-5-azabicyclo[2.2.1]heptane hydrochloride | MS ES + ve m/z 327 (M + H) |
| 59 | 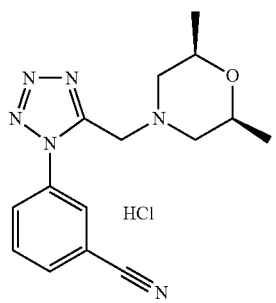 [SMILES: C[C@@H]1CN(Cc2nnnn2-c2cccc(C#N)c2)C[C@H](C)O1 ; Cl] | 3-(5-{[(cis)-2,6-Dimethyl-4-morpholinyl]methyl}-1H-tetrazol-1-yl)benzonitrile hydrochloride | MS ES + ve m/z 299 (M+H) |
| 60 | 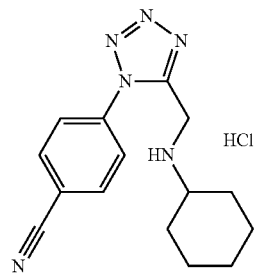 [SMILES: N#Cc1ccc(-n2nnnc2CNC2CCCCC2)cc1 ; Cl] | 4-{5-[(Cyclohexylamino)methyl]-1H-tetrazol-1-yl}benzonitrile hydrochloride | MS ES + ve m/z 283 (M+H) |
| 61 | 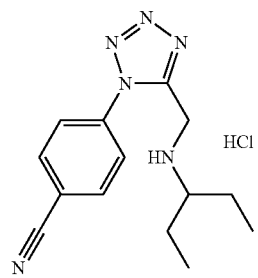 [SMILES: CCC(CC)NCc1nnnn1-c1ccc(C#N)cc1 ; Cl] | 4-(5-{[(1-Ethylpropyl)amino]methyl}-1H-tetrazol-1-yl)benzonitrile hydrochloride | MS ES + ve m/z 271 (M + H) |

Starting iso-cyanides for compounds 56 and 61 were purchased from Priaxon AG, Munich, Germany.

The following compounds were prepared in a similar manner to that described for Compound 25, using the appropriate alkylating agent and amine:

| Compound No. | Structure | Name | Analytical data |
|---|---|---|---|
| 62 | 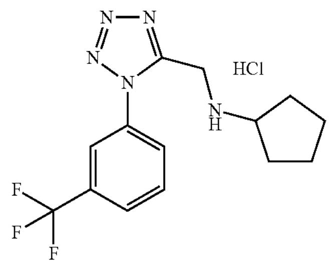 [SMILES: FC(F)(F)c1cccc(-n2nnnc2CNC2CCCC2)c1 ; Cl] | N-({1-[3-(Trifluoromethyl)phenyl]-1H-tetrazol-5-yl}methyl)cyclopentanamine hydrochloride | MS ES + ve m/z 312 (M + H) |
| 63 | 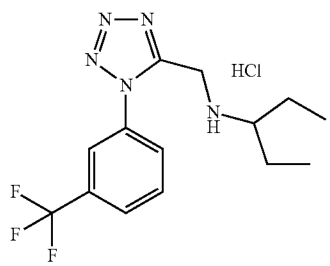 [SMILES: CCC(CC)NCc1nnnn1-c1cccc(C(F)(F)F)c1 ; Cl] | N-({1-[3-(Trifluoromethyl)phenyl]-1H-tetrazol-5-yl}methyl)-3-pentanamine hydrochloride | MS ES + ve m/z 314 (M + H) |
| 64 | 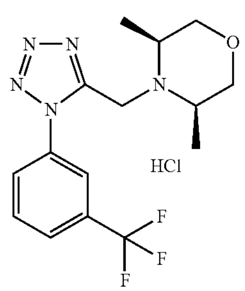 [SMILES: C[C@@H]1COC[C@H](C)N1Cc1nnnn1-c1cccc(C(F)(F)F)c1 ; Cl] | (cis)-3,5-dimethyl-4-({1-[3-(Trifluoromethyl)phenyl]-1H-tetrazol-5-yl}methyl)morpholine hydrochloride | MS ES + ve m/z 342 (M + H) |
| 65 | 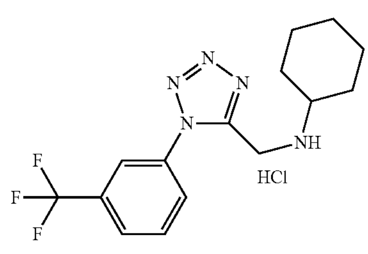 [SMILES: FC(F)(F)c1cccc(-n2nnnc2CNC2CCCCC2)c1 ; Cl] | N-({1-[3-(Trifluoromethyl)phenyl]-1H-tetrazol-5-yl}methyl)cyclohexanamine hydrochloride | MS ES + ve m/z 326 (M + H) |
| 66 | 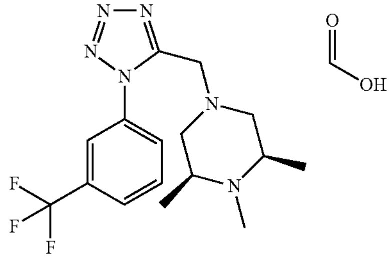 [SMILES: C[C@@H]1CN(Cc2nnnn2-c2cccc(C(F)(F)F)c2)C[C@H](C)N1C ; O=CO] | cis-1,2,6-Trimethyl-4-({1-[3-(trifluoromethyl)phenyl]-1H-tetrazol-5-yl}methyl)piperazine formate salt | MS ES + ve m/z 355 (M + H) |

| Compound No. | Structure | Name | Analytical data |
|---|---|---|---|
| 67 | 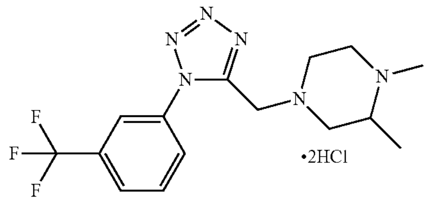 [SMILES: CC1CN(Cc2nnnn2-c2cccc(C(F)(F)F)c2)CCN1C] | 1,2-Dimethyl-4-({1-[3-(trifluoromethyl)phenyl]-1H-tetrazol-5-yl}methyl)piperazine dihydrochloride | MS ES + ve m/z 341 (M + H) |
| 68 | 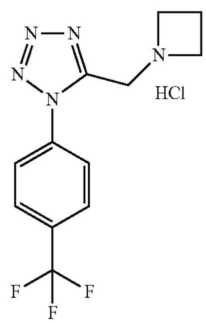 [SMILES: FC(F)(F)c1ccc(-n2nnnc2CN2CCC2)cc1 ; Cl] | 5-(1-Azetidinylmethyl)-1-[4-(trifluoromethyl)phenyl]-1H-tetrazole hydrochloride | MS ES + ve m/z 284 (M + H) |
| 69 | 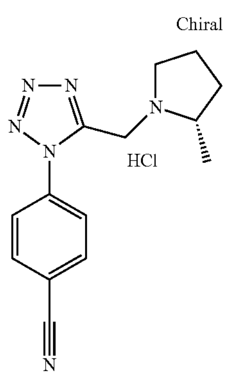 [SMILES: C[C@H]1CCCN1Cc1nnnn1-c1ccc(C#N)cc1 ; Cl] | 4-(5-{[(2S)-2-Methyl-1-pyrrolidinyl]methyl}-1H-tetrazol-1-yl)benzonitrile | MS ES + ve m/z 269 (M + H) |
| 70 | 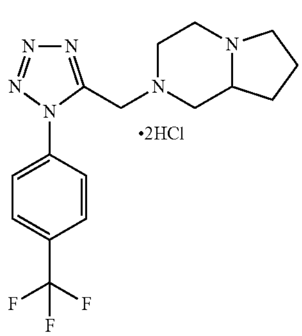 [SMILES: FC(F)(F)c1ccc(-n2nnnc2CN2CCN3CCCC3C2)cc1] | 2-({1-[4-(Trifluoromethyl)phenyl]-1H-tetrazol-5-yl}methyl)octahydropyrrolo[1,2-a]pyrazine dihydrochloride | MS ES + ve m/z 353 (M + H) |

-continued

| Compound No. | Structure | Name | Analytical data |
|---|---|---|---|
| 71 | 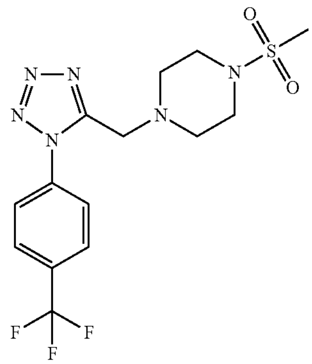 [SMILES: CS(=O)(=O)N1CCN(Cc2nnnn2-c2ccc(C(F)(F)F)cc2)CC1] | 1-(Methylsulfonyl)-4-({1-[4-(trifluoromethyl)phenyl]-1H-tetrazol-5-yl}methyl)piperazine | MS ES + ve m/z 391 (M + H) |
| 72 | 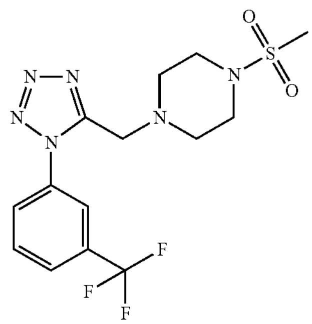 [SMILES: CS(=O)(=O)N1CCN(Cc2nnnn2-c2cccc(C(F)(F)F)c2)CC1] | 1-(Methylsulfonyl)-4-({1-[3-(trifluoromethyl)phenyl]-1H-tetrazol-5-yl}methyl)piperazine | MS ES + ve m/z 391 (M + H) |
| 73 | 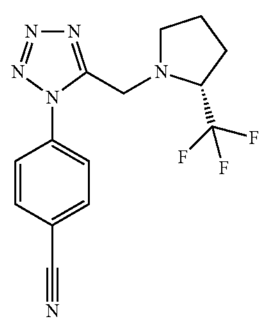 [SMILES: N#Cc1ccc(-n2nnnc2CN2CCC[C@@H]2C(F)(F)F)cc1] | 4-(5-{[(2R)-2-(Trifluoromethyl)-1-pyrrolidinyl]methyl}-1H-tetrazol-1-yl)benzonitrile | MS ES + ve m/z 323 (M + H) |
| 74 | 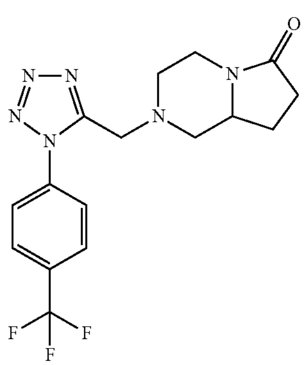 [SMILES: O=C1CCC2CN(Cc3nnnn3-c3ccc(C(F)(F)F)cc3)CCN12] | 2-({1-[4-(Trifluoromethyl)phenyl]-1H-tetrazol-5-yl}methyl)hexahydropyrrolo[1,2-a]pyrazin-6(2H)-one | MS ES + ve m/z 367 (M + H) |

| Compound No. | Structure | Name | Analytical data |
|---|---|---|---|
| 75 | 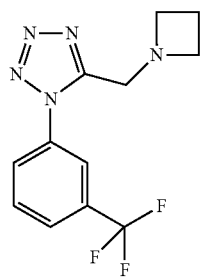 [SMILES: FC(F)(F)c1cccc(-n2nnnc2CN2CCC2)c1] | 5-(1-Azetidinylmethyl)-1-[3-(trifluoromethyl)phenyl]-1H-tetrazole | MS ES + ve m/z 284 (M + H) |
| 76 | 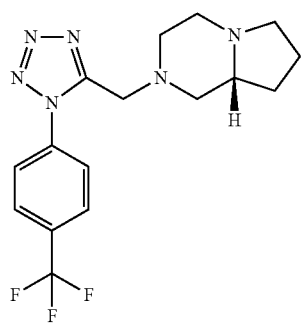 [SMILES: FC(F)(F)c1ccc(-n2nnnc2CN2CCN3CCC[C@@H]3C2)cc1] | (8aR)-2-({1-[4-(Trifluoromethyl)phenyl]-1H-tetrazol-5-yl}methyl)octahydropyrrolo[1,2-a]pyrazine | MS ES + ve m/z 353 (M + H) |
| 77 | 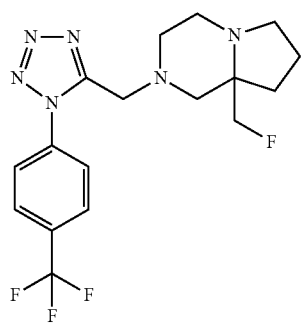 [SMILES: FCC12CCCN1CCN(Cc1nnnn1-c1ccc(C(F)(F)F)cc1)C2] | 8a-(Fluoromethyl)-2-({1-[4-(trifluoromethyl)phenyl]-1H-tetrazol-5-yl}methyl)octahydropyrrolo[1,2-a]pyrazine | MS ES + ve m/z 385 (M + H) |
| 78 | 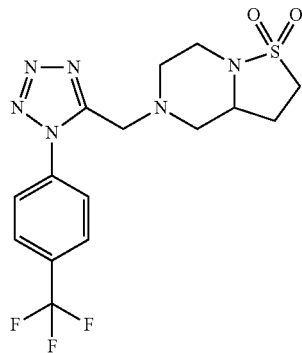 [SMILES: O=S1(=O)CCC2CN(Cc3nnnn3-c3ccc(C(F)(F)F)cc3)CCN21] | 5-({1-[4-(Trifluoromethyl)phenyl]-1H-tetrazol-5-yl}methyl)hexahydro-2H-isothiazolo[2,3-a]pyrazine 1,1-dioxide | MS ES + ve m/z 403 (M + H) |

-continued

| Compound No. | Structure | Name | Analytical data |
|---|---|---|---|
| 79 | 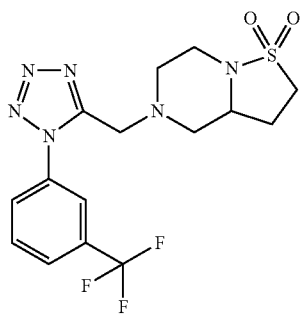 [SMILES: O=S1(=O)CCC2CN(Cc3nnnn3-c3cccc(C(F)(F)F)c3)CCN21] | 5-({1-[3-(Trifluoromethyl)phenyl]-1H-tetrazol-5-yl}methyl)hexahydro-2H-isothiazolo[2,3-a]pyrazine 1,1-dioxide | MS ES + ve m/z 403 (M + H) |
| 80 | 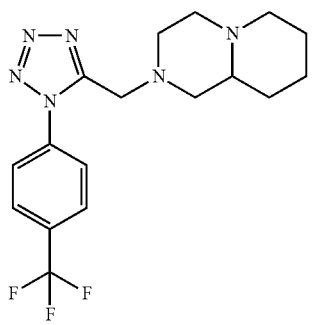 [SMILES: FC(F)(F)c1ccc(-n2nnnc2CN2CCN3CCCCC3C2)cc1] | 2-({1-[4-(Trifluoromethyl)phenyl]-1H-tetrazol-5-yl}methyl)octahydro-2H-pyrido[1,2-a]pyrazine | MS ES + ve m/z 367 (M + H) |
| 81 | 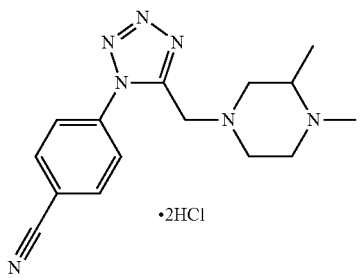 [SMILES: CC1CN(Cc2nnnn2-c2ccc(C#N)cc2)CCN1C] | 4-{5-[(3,4-Dimethyl-1-piperazinyl)methyl]-1H-tetrazol-1-yl}benzonitrile dichydrochloride | MS ES + ve m/z 298 (M + H) |
| 82 | 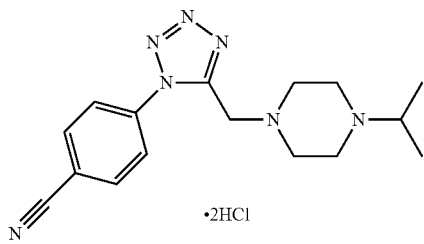 [SMILES: CC(C)N1CCN(Cc2nnnn2-c2ccc(C#N)cc2)CC1] | 4-(5-{[4-(1-Methylethyl)-1-piperazinyl]methyl}-1H-tetrazol-1-yl)benzonitrile dihydrochloride | MS ES + ve m/z 312 (M + H) |
| 83 | 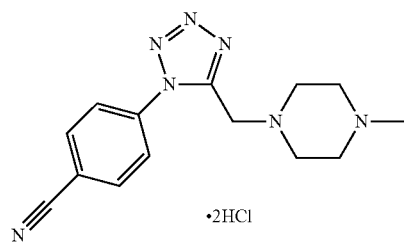 [SMILES: CN1CCN(Cc2nnnn2-c2ccc(C#N)cc2)CC1] | 4-{5-[(4-Methyl-1-piperazinyl)methyl]-1H-tetrazol-1-yl}benzonitrile hydrochloride | MS ES + ve m/z 284 (M + H) |

Starting amine for Compound 64 is commercially available as the hydrochloride salt, for example from Speed Chemical Corp., Shanghai, China. The preparation of the amine is described in US patent application publication US 2005/0038032 (Allison et al., Example 25).

Preparation of the starting amine for Compound 66 is described in US Patent Application US 2007/0142362A1 (Solvay Pharmaceuticals, page 41).

Starting amine for Compound 74 is commercially available, for example from AstaTech Inc., Bristol, USA and J&W Pharmlab LLC, Levittown, USA.

Starting amine for Compound 76 is commercially available, for example from J & W PharmLab LLC, Levittown, USA.

Starting amine for Compound 77 was purchased from Peakdale Molecular Ltd., Chapel-en-le-Frith, England.

Starting amine for Compounds 78179 was purchased from Syngene, Bangalore, India. Preparation of this amine is described in PCT patent application WO 2007/028654 (Smithkline Beecham, Description 10).

Starting amine for Compound 80 was purchased from Chembridge, San Diego, USA.

The following compounds were prepared in a similar manner to that described for Compound 33, using the appropriate substituted piperazinone intermediate and alkylating agent:

| Compound No. | Structure | Name | Analytical data |
| --- | --- | --- | --- |
| 84 | 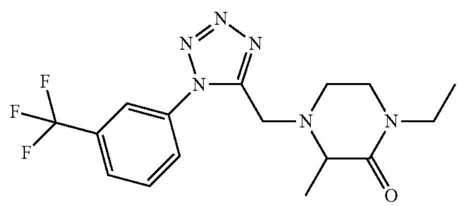 [SMILES: CCN1CCN(Cc2nnnn2-c2cccc(C(F)(F)F)c2)C(C)C1=O] | 1-Ethyl-3-methyl-4-({1-[3-(trifluoromethyl)phenyl]-1H-tetrazol-5-yl}methyl)-2-piperazinone | MS ES + ve m/z 369 (M + H) |
| 85 | 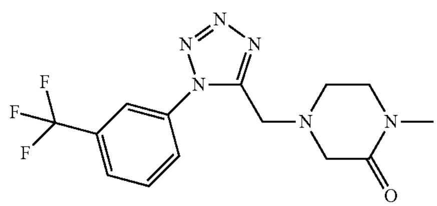 [SMILES: CN1CCN(Cc2nnnn2-c2cccc(C(F)(F)F)c2)CC1=O] | 1-Methyl-4-({1-[3-(trifluoromethyl)phenyl]-1H-tetrazol-5-yl}methyl)-2-piperazinone | MS ES + ve m/z 341 (M + H) |
| 86 | 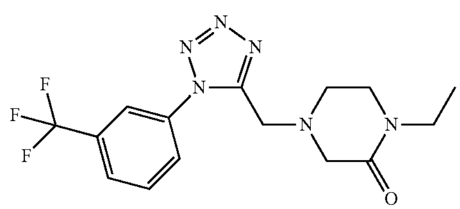 [SMILES: CCN1CCN(Cc2nnnn2-c2cccc(C(F)(F)F)c2)CC1=O] | 1-Ethyl-4-({1-[3-(trifluoromethyl)phenyl]-1H-tetrazol-5-yl}methyl)-2-piperazinone | MS ES + ve m/z 355 (M + H) |
| 87 | 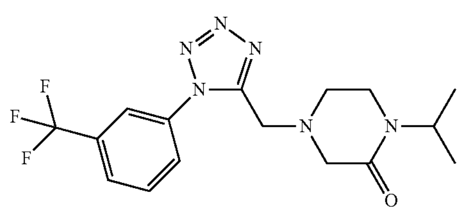 [SMILES: CC(C)N1CCN(Cc2nnnn2-c2cccc(C(F)(F)F)c2)CC1=O] | 1-(1-Methylethyl)-4-({1-[3-(trifluoromethyl)phenyl]-1H-tetrazol-5-yl}methyl)-2-piperazinone | MS ES + ve m/z 369 (M + H) |
| 88 | 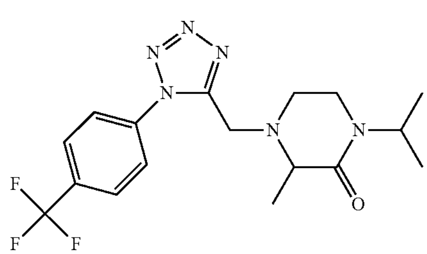 [SMILES: CC1C(=O)N(C(C)C)CCN1Cc1nnnn1-c1ccc(C(F)(F)F)cc1] | (3S)-3-Methyl-1-(1-methylethyl)-4-({1-[4-(trifluoromethyl)phenyl]-1H-tetrazol-5-yl}methyl)-2-piperazinone | MS ES + ve m/z 383 (M + H) |

-continued

| Compound No. | Structure | Name | Analytical data |
|---|---|---|---|
| 89 | 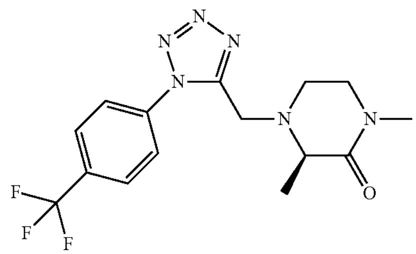 [SMILES: C[C@@H]1C(=O)N(C)CCN1Cc1nnnn1-c1ccc(C(F)(F)F)cc1] | (3R)-1,3-Dimethyl-4-({1-[4-(trifluoromethyl)phenyl]-1H-tetrazol-5-yl}methyl)-2-piperazinone | MS ES + ve m/z 355 (M + H) |
| 90 | 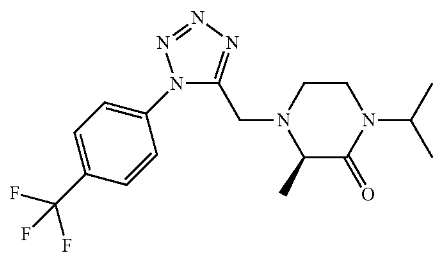 [SMILES: CC(C)N1CCN(Cc2nnnn2-c2ccc(C(F)(F)F)cc2)[C@H](C)C1=O] | (3R)-3-Methyl-1-(1-methylethyl)-4-({1-[4-(trifluoromethyl)phenyl]-1H-tetrazol-5-yl}methyl)-2-piperazinone | MS ES + ve m/z 383 (M + H) |

The following compounds were prepared in a similar manner to that described for Compound 45, using the appropriate substituted piperazine intermediate and alkylating agent:

| Compound No | Structure | Name | Analytical data |
|---|---|---|---|
| 91 | 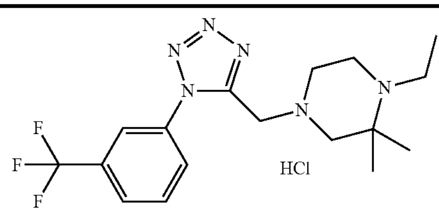 | 1-Ethyl-2,2-dimethyl-4-({1-[3-(trifluoromethyl)phenyl]-1H-tetrazol-5-yl}methyl)piperazine hydrochloride | MS ES + ve m/z 369 (M + H) |
| 92 | 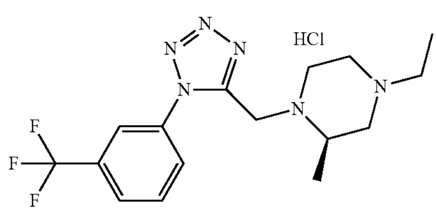 [SMILES: CCN1CCN(Cc2nnnn2-c2cccc(C(F)(F)F)c2)[C@H](C)C1 ; Cl] | (2R)-4-Ethyl-2-methyl-1-({1-[3-(trifluoromethyl)phenyl]-1H-tetrazol-5-yl}methyl)piperazine hydrochloride | MS ES + ve m/z 355 (M + H) |
| 93 | 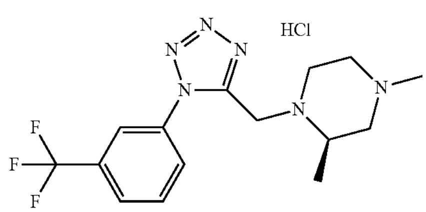 [SMILES: C[C@@H]1CN(C)CCN1Cc1nnnn1-c1cccc(C(F)(F)F)c1 ; Cl] | (2R)-2,4-Dimethyl-1-({1-[3-(trifluoromethyl)phenyl]-1H-tetrazol-5-yl}methyl)piperazine hydrochloride | MS ES + ve m/z 341 (M + H) |
| 94 | 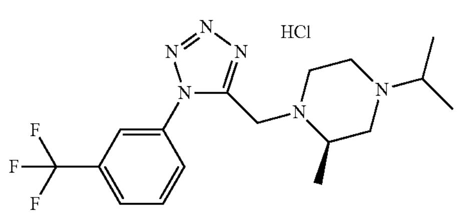 [SMILES: CC(C)N1CCN(Cc2nnnn2-c2cccc(C(F)(F)F)c2)[C@H](C)C1 ; Cl] | (2R)-2-Methyl-4-(1-methylethyl)-1-({1-[3-(trifluoromethyl)phenyl]-1H-tetrazol-5-yl}methyl)piperazine hydrochloride | MS ES + ve m/z 369 (M + H) |

-continued

| Compound No | Structure | Name | Analytical data |
|---|---|---|---|
| 95 | 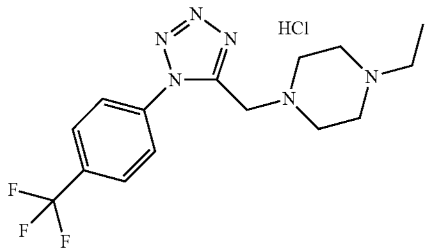 [SMILES: CCN1CCN(Cc2nnnn2-c2ccc(C(F)(F)F)cc2)CC1 ; Cl] | 1-Ethyl-4-({1-[4-(trifluoromethyl)phenyl]-1H-tetrazol-5-yl}methyl)piperazine hydrochloride | MS ES + ve m/z 341 (M + H) |
| 96 | 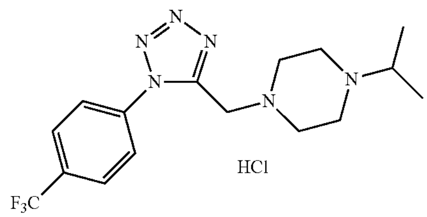 [SMILES: CC(C)N1CCN(Cc2nnnn2-c2ccc(C(F)(F)F)cc2)CC1 ; Cl] | 1-(1-Methylethyl)-4-({1-[4-(trifluoromethyl)phenyl]-1H-tetrazol-5-yl}methyl)piperazine | MS ES + ve m/z 355 (M + H) |
| 97 | 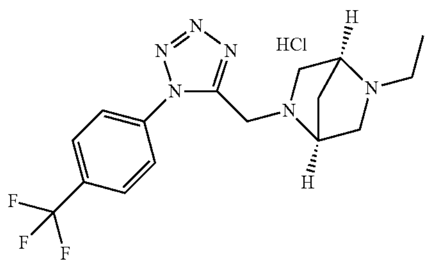 [SMILES: CCN1C[C@@H]2C[C@H]1CN2Cc1nnnn1-c1ccc(C(F)(F)F)cc1 ; Cl] | (1S,4S)-2-Ethyl-5-({1-[4-(trifluoromethyl)phenyl]-1H-tetrazol-5-yl}methyl)-2,5-diazabicyclo[2.2.1]heptane hydrochloride | MS ES + ve m/z 353 (M + H) |
| 98 | 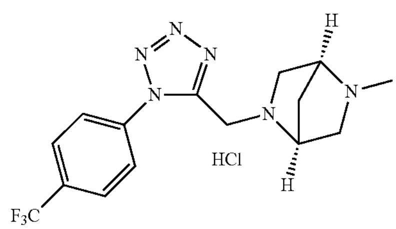 [SMILES: CN1C[C@@H]2C[C@H]1CN2Cc1nnnn1-c1ccc(C(F)(F)F)cc1 ; Cl] | (1S,4S)-2-Methyl-5-({1-[4-(trifluoromethyl)phenyl]-1H-tetrazol-5-yl}methyl)-2,5-diazabicyclo[2.2.1]heptane hydrochloride | MS ES + ve m/z 339 (M + H) |

The following compounds were prepared in a similar manner to that described for Compound 46 using the appropriate protected piperazine intermediate:

| Compound No. | Structure | Name | Analytical data |
|---|---|---|---|
| 99 | 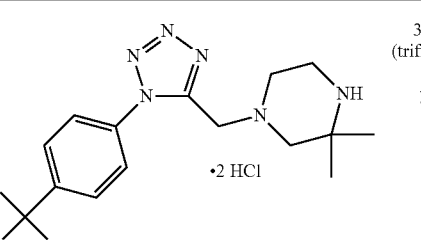 | 3,3-Dimethyl-1-({1-[4-(trifluoromethyl)phenyl]-1H-tetrazol-5-yl}methyl)piperazine dihydrochloride | MS ES + ve m/z 341 (M + H) |

| Compound No. | Structure | Name | Analytical data |
|---|---|---|---|
| 100 | 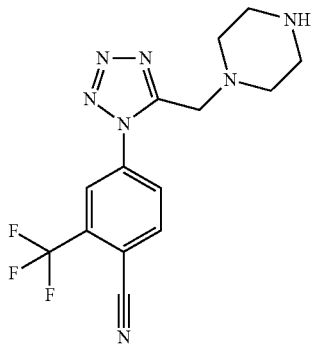 [SMILES: N#Cc1ccc(-n2nnnc2CN2CCNCC2)cc1C(F)(F)F] | 3-Methyl-1-({1-[4-(trifluoromethyl)phenyl]-1H-tetrazol-5-yl}methyl)piperazine dihydrochloride | MS ES + ve m/z 327 (M + H) |

Example 101

4-[5-(1-piperazinylmethyl)-1H-tetrazol-1-yl]-2-(trifluoromethyl)benzonitrile To a solution of 1,1-dimethylethyl 4-({1-[4-cyano-3-(trifluoromethyl)phenyl]-1H-tetrazol-5-yl}methyl)-1-piperazinecarboxylate (Intermediate 25, 532 mg, 1.22 mmol) in methanol (8 mL) was added hydrochloric acid in dioxane (5 mL, 20.0 mmol). The reaction mixture was stirred at room temperature for 1 h. The mixture was concentrated, the white solid was dissolved in methanol and poured onto a 5 g SCX cartridge, washed with methanol (2 CV) and eluted with 10% ammonia) in methanol (2 CV). The ammonia in methanol fraction was concentrated under vacuum to leave a white solid, 4-[5-(1-piperazinylmethyl)-1H-tetrazol-1-yl]-2-(trifluoromethyl)benzonitrile (402 mg).

MS ES+ve m/z 338 (M+H)

$^1$H NMR (400 MHz, CHLOROFORM-d) δ ppm 2.57 (m, 4H), 2.88 (t, J=4.7 Hz, 4H), 3.82 (s, 2H), 8.10 (d, J=8.4 Hz, 1H), 8.31 (dd, J=8.4, 1.9 Hz, 1H), 8.84 (d, J=1.9 Hz, 1H).

Example 102

4-{5-[(4-acetyl-1-piperazinyl)methyl]-1H-tetrazol-1-yl}-2-(trifluoromethyl)benzonitrile

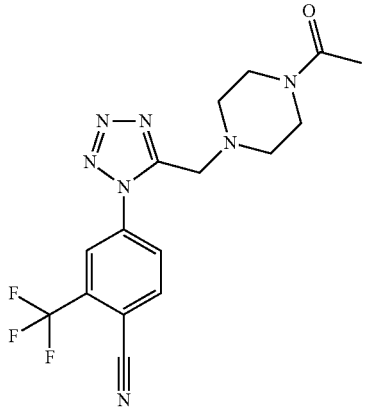 [SMILES: CC(=O)N1CCN(Cc2nnnn2-c2ccc(C#N)c(C(F)(F)F)c2)CC1]

To a solution of 4-[5-(1-piperazinylmethyl)-1H-tetrazol-1-yl]-2-(trifluoromethyl)benzonitrile (Example 101, 67 mg, 0.199 mmol) in DCM (2 mL) was added triethylamine (55 μL, 0.395 mmol) and then acetyl chloride (21 μL, 0.295 mmol). The reaction mixture was stirred at room temperature for 30 minutes under argon atmosphere. Water (2 mL) was added, and the mixture poured onto a hydrophobic cartridge. The heavier organic phase was concentrated under vacuum to leave white crystals. Purification by MDAP left a white solid, 4-{5-[(4-acetyl-1-piperazinyl)methyl]-1H-tetrazol-1-yl}-2-(trifluoromethyl)benzonitrile (48 mg).

MS ES+ve m/z 380 (M+H)

$^1$H NMR (400 MHz, CHLOROFORM-d) δ ppm 2.12 (s, 3H), 2.60 (t, J=5.0 Hz, 2H), 2.64 (t, J=5.0 Hz, 2H), 3.49 (t, J=4.8 Hz, 2H), 3.65 (t, J=4.8 Hz, 2H), 3.87 (s, 2H), 8.12 (d, J=8.3 Hz, 1H), 8.28 (dd, J=8.3, 2.0 Hz, 1H), 8.78 (d, J=2.0 Hz, 1H).

Example 103

4-[5-(3-oxa-8-azabicyclo[3.2.1]oct-8-ylmethyl)-1H-tetrazol-1-yl]-2-(trifluoromethyl)benzonitrile hydrochloride

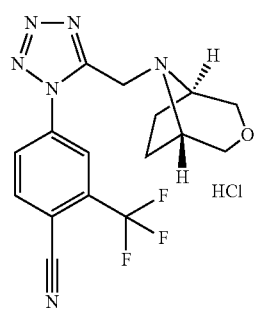 [SMILES: N#Cc1ccc(-n2nnnc2CN2[C@@H]3CC[C@H]2COC3)cc1C(F)(F)F ; Cl]

To a solution of 4-[5-(chloromethyl)-1H-tetrazol-1-yl]-2-(trifluoromethyl)benzonitrile (Intermediate 24, 1.70 g, 5.91 mmol) and 3-oxa-8-azabicyclo[3.2.1]octane hydrochloride (Intermediate 27, 0.884 g, 5.91 mmol) in acetonitrile (25 mL) was added di-isopropylethylamine (2.06 mL, 11.8 mmol). The reaction was heated to 85° C. and stirred for 6 hours. The reaction was cooled and the solvent removed under vacuum. The residue was partitioned between DCM (100 mL) and water (50 mL). The aqueous layer was separated and extracted with DCM (50 mL). The DCM layers were combined and the solvent removed. The residue was purified by silica chromatography (Biotage SP4, eluting a gradient of ethyl acetate in iso-hexane) to yield a colourless gum. The product was dissolved in a minimum of DCM before the addition of 1N HCl in diethyl ether (10 mL). The solvent was removed from the resulting suspension. The solid obtained was triturated with diethyl ether (5 mL), the ether decanted and the solid dried under vacuum at 40° C. for 18 hours to yield the title compound as a white solid (1.43 g).

MS ES+ve m/z 365 (M+H)

$^1$H NMR (400 MHz, Methanol-$d_4$) δ ppm 2.33 (s, 4H) 3.86 (d, J=12.3 Hz, 2H) 4.07 (d, J=12.9 Hz, 2H) 4.26-4.37 (m, 2H) 4.77-4.86 (m, 2H) 8.21 (dd, J=8.2, 2.1 Hz, 1H) 8.33-8.38 (m, 2H)

Example 104

3-{5-[(1S,4S)-2-oxa-5-azabicyclo[2.2.1]hept-5-ylmethyl]-1H-tetrazol-1-yl}-5-(trifluoromethyl)benzonitrile

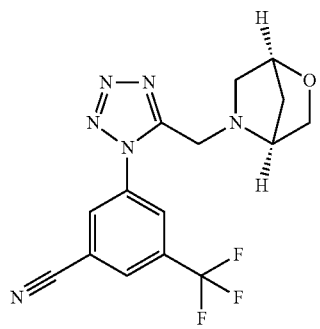 [SMILES: N#Cc1cc(-n2nnnc2CN2C[C@@H]3C[C@H]2CO3)cc(C(F)(F)F)c1]

To a solution of 3-{5-[(1S,4S)-2-oxa-5-azabicyclo[2.2.1]hept-5-ylmethyl]-1H-tetrazol-1-yl}-5-(trifluoromethyl)benzamide (Intermediate 32, 100 mg, 0.272 mmol) and triethylamine (0.076 ml, 0.543 mmol) in dichloromethane (5 ml) was added trifluoroacetic anhydride (0.038 ml, 0.272 mmol). The reaction was stirred at room temperature for 4 hours before the addition of trifluoroacetic anhydride (0.038 ml, 0.272 mmol). The reaction was stirred at room temperature for a further three hours. The reaction was partitioned between DCM (5 mL) and water (5 mL). The organic layer was collected via a hydrophobic frit and the solvent removed. The residue was purified by silica chromatography (Biotage SP4, eluting a gradient from 20-80% EtOAc in iso-hexane). The compound was further purified by high pH MDAP to yield the title compound as a white solid (36 mg)

MS ES+ve m/z 351 (M+H)

$^1$H NMR (400 MHz, METHANOL-$d_4$) δ ppm 1.75 (d, 1H) 1.78-1.83 (m, 1H) 2.64 (d, J=10.3 Hz, 1H) 2.81 (dd, J=10.2, 1.6 Hz, 1H) 3.49 (s, 1H) 3.63 (dd, J=7.9, 1.8 Hz, 1H) 3.92 (d, J=7.9 Hz, 1H) 4.13 (d, J=14.3 Hz, 1H) 4.22 (d, J=14.3 Hz, 1H) 4.43 (s, 1H) 8.40 (s, 1H) 8.60 (s, 1H) 8.68 (s, 1H)

Example 105

4-[5-(2,8-diazaspiro[4.5]dec-8-ylmethyl)-1H-tetrazol-1-yl]-2-(trifluoromethyl)benzonitrile

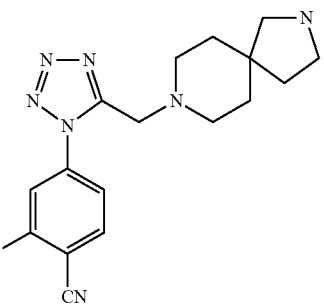

1,1-dimethylethyl 8-({1-[(4-cyano-3-(trifluoromethyl)phenyl]-1H-tetrazol-5-yl}methyl)-2,8-diazaspiro[4.5]decane-2-carboxylate (Intermediate 35, 680 mg, 1.38 mmol) was treated with 4M HCl in dioxane (8 mL, 1.38 mmol) and solution was stirred at 25° C. for 1 hour.

Solvent was removed to afford a yellow solid which was dissolved in MeOH and loaded onto an SCX cartridge, washed with MeOH and eluted with 2M methanolic ammonia. Relevant fractions were concentrated to afford a pale yellow oil. This oil was dried over two days in a vacuum oven at 45° C. to afford 350 mg of the titled compound as a pale yellow solid.

MS ES+ve m/z 392 (M+H)

$^1$H NMR (400 MHz, METHANOL-$d_4$) δ ppm 1.49 (t, 4H) 1.63 (t, J=7.23 Hz, 2H) 2.42-2.56 (m, 4H) 2.68 (s, 2H) 2.95 (t, J=7.13 Hz, 2H) 3.91 (s, 2H) 8.26-8.36 (m, 2H) 8.71 (s, 1H)

Example 106

4-(5-{[4-(Propylsulfonyl)-1-piperazinyl]methyl}-1H-tetrazol-1-yl)-2-(trifluoromethyl)benzonitrile

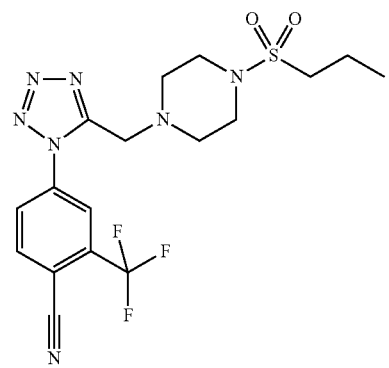 [SMILES: CCCS(=O)(=O)N1CCN(Cc2nnnn2-c2ccc(C#N)c(C(F)(F)F)c2)CC1]

4-[5-(1-piperazinylmethyl)-1H-tetrazol-1-yl]-2-(trifluoromethyl)benzonitrile (Example 101, 50 mg, 0.15 mmol) was dissolved in DCM and treated with triethylamine (41 µL, 0.29 mmol) followed by 1-propanesulfonyl chloride (20 µL, 0.18 mmol). The mixture was stirred at ambient temperature under argon for 2.5 hours. The reaction mixture was partitioned between water and DCM (5 mL each) and the layers were separated using a hydrophobic frit. The aqueous layer was extracted with further DCM (2×5 mL). The combined DCM extracts were concentrated in vacuo to give the title compound as a pale cream solid (62 mg).

MS ES+ve m/z 444 (M+H).

$^1$H NMR (400 MHz, Chloroform-d) δ ppm 1.08 (t, J=7.5 Hz, 3H), 1.80-1.92 (m, 2H), 2.72 (t, J=9.5 Hz, 4H), 2.87-2.93 (m, 2H), 3.28-3.36 (m, 4H), 3.89 (s, 2H), 8.12 (d, J=8 Hz, 1H), 8.25 (dd, J=8, 2 Hz, 1H), 8.70 (d, J=2 Hz, 1H).

Example 107

4-(5-{[cis-2,6-Dimethyl-4-(methylsulfonyl)-1-piperazinyl]methyl}-1H-tetrazol-1-yl)-2-(trifluoromethyl)benzonitrile

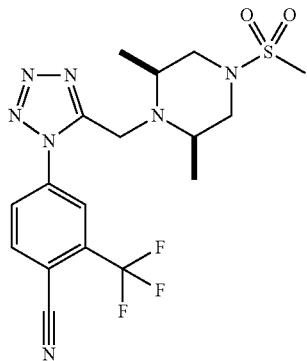 [SMILES: C[C@@H]1CN(S(C)(=O)=O)C[C@H](C)N1Cc1nnnn1-c1ccc(C#N)c(C(F)(F)F)c1]

4-[5-(Chloromethyl)-1H-tetrazol-1-yl]-2-(trifluoromethyl)benzonitrile (Intermediate 24, 86 mg, 0.3 mmol) and 3,5-dimethyl-1-(methylsulfonyl)piperazine (Intermediate 36, 78 mg, 0.41 mmol) were weighed into a vial and suspended in acetonitrile (1.2 mL). Triethylamine (84 μL, 0.60 mmol) was added, and the mixture was heated at 140° C. in a microwave with stirring for 3 h. The reaction mixture was applied to a 10 g SCX cartridge, pre-washed with MeOH (50 mL). This was eluted with MeOH (100 mL) and 10% aq NH3 in MeOH (100 mL). The basic fractions were concentrated to give an off-white solid (137 mg). This was purified by MDAP to give the title compound as a colourless solid (38 mg), confirmed by NMR to be the pure cis-isomer.

MS ES+ve m/z 444 (M+H).

$^1$H NMR (400 MHz, Chloroform-d) δ ppm 1.03 (d, J=7 Hz, 6H), 2.71 (dd, J=12, 9 Hz, 2H), 2.78 (s, 3H), 2.99-3.09 (m, 2H), 3.40 (dd, J=12, 2 Hz, 2H), 4.25 (s, 2H), 7.96 (dd, J=8, 2 Hz, 1H), 8.13 (d, J=8 Hz, 1H), 8.17 (d, J=2 Hz, 1H).

Example 108

1-{[1-(4-chlorophenyl)-1H-tetrazol-5-yl]methyl}-4-(ethylsulfonyl)piperazine

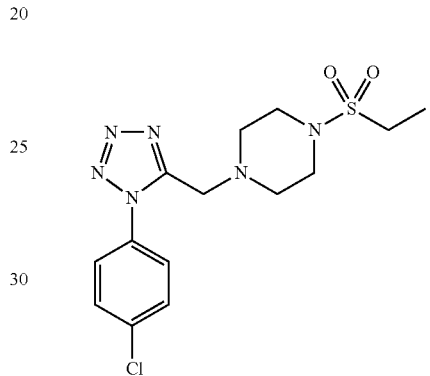

Commercially available, for example from Ambinter Screening Collection, Paris, France.

The following compounds were prepared in a similar manner to that described for Compound 28, using the appropriate amine and aryl iso-cyanide:

| Compound No. | Structure | Name | Analytical data |
|---|---|---|---|
| 109 | 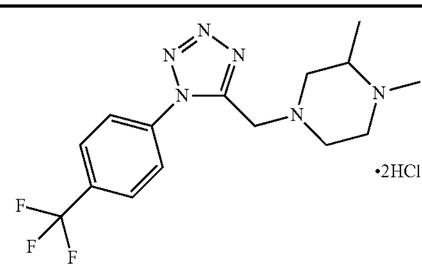 | 1,2-dimethyl-4-({1-[4-(trifluoromethyl)phenyl]-1H-tetrazol-5-yl}methyl)piperazine dihydrochloride | MS ES + ve m/z 341 (M + H) |
| 110 | 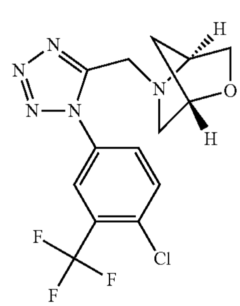 [SMILES: FC(F)(F)c1cc(-n2nnnc2CN2C[C@@H]3C[C@H]2CO3)ccc1Cl] | (1S,4S)-5-({1-[4-chloro-3-(trifluoromethyl)phenyl]-1H-tetrazol-5-yl}methyl)-2-oxa-5-azabicyclo[2.2.1]heptane hydrochloride | MS ES + ve m/z 360 (M + H) |

-continued

| Compound No. | Structure | Name | Analytical data |
|---|---|---|---|
| 111 | 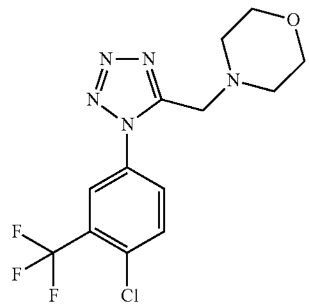 [SMILES: FC(F)(F)c1cc(-n2nnnc2CN2CCOCC2)ccc1Cl] | 4-({1-[4-chloro-3-(trifluoromethyl)phenyl]-1H-tetrazol-5-yl}methyl)morpholine | MS ES + ve m/z 348 (M + H) |
| 112 | 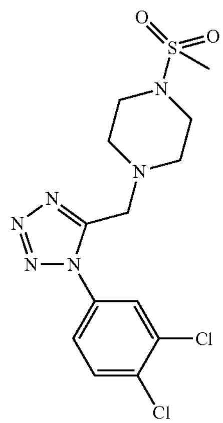 [SMILES: CS(=O)(=O)N1CCN(Cc2nnnn2-c2ccc(Cl)c(Cl)c2)CC1] | 1-{[1-(3,4-dichlorophenyl)-1H-tetrazol-5-yl]methyl}-4-(methylsulfonyl)piperazine | MS ES + ve m/z 391 (M + H) |
| 113 | 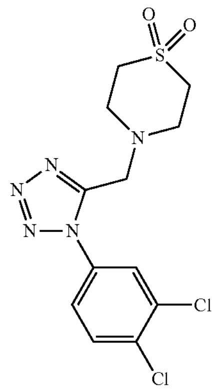 [SMILES: O=S1(=O)CCN(Cc2nnnn2-c2ccc(Cl)c(Cl)c2)CC1] | 4-{[1-(3,4-dichlorophenyl)-1H-tetrazol-5-yl]methyl}thiomorpholine 1,1-dioxide | MS ES + ve m/z 362 (M + H) |
| 114 | 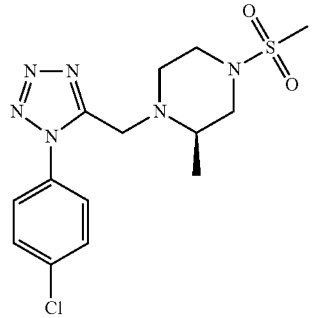 [SMILES: C[C@@H]1CN(S(C)(=O)=O)CCN1Cc1nnnn1-c1ccc(Cl)cc1] | (2R)-1-{[1-(4-chlorophenyl)-1H-tetrazol-5-yl]methyl}-2-methyl-4-(methylsulfonyl)piperazine | MS ES + ve m/z 371 (M + H) |

-continued

| Compound No. | Structure | Name | Analytical data |
|---|---|---|---|
| 115 | 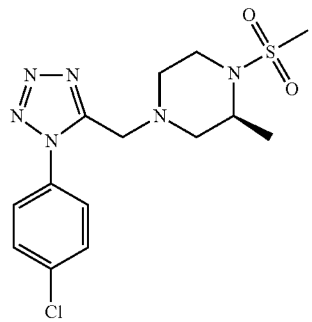 [SMILES: C[C@H]1CN(Cc2nnnn2-c2ccc(Cl)cc2)CCN1S(C)(=O)=O] | (2S)-4-{[1-(4-chlorophenyl)-1H-tetrazol-5-yl]methyl}-2-methyl-1-(methylsulfonyl)piperazine | MS ES + ve m/z 371 (M + H) |

The following compounds were prepared in a similar manner to that described for Compound 25, using the appropriate alkylating agent and amine:

| Compound No. | Structure | Name | Analytical data |
|---|---|---|---|
| 116 | 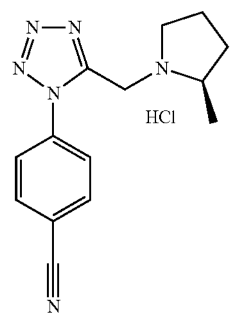 [SMILES: C[C@@H]1CCCN1Cc1nnnn1-c1ccc(C#N)cc1 ; Cl] | 4-(5-{[(2R)-2-methyl-1-pyrrolidinyl]methyl}-1H-tetrazol-1-yl)benzonitrile hydrochloride | MS ES + ve m/z 269 (M + H) |
| 117 | 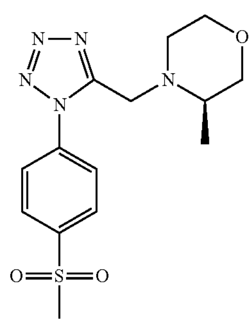 [SMILES: C[C@@H]1COCCN1Cc1nnnn1-c1ccc(S(C)(=O)=O)cc1] | (3R)-3-methyl-4-({1-[4-(methylsulfonyl)phenyl]-1H-tetrazol-5-yl}methyl)morpholine | MS ES + ve m/z 338 (M + H) |
| 118 | 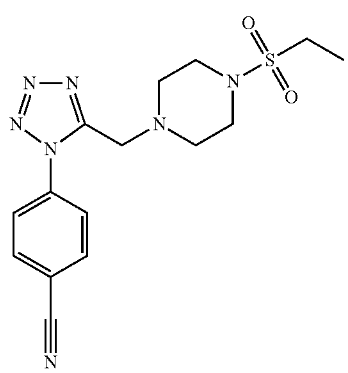 [SMILES: CCS(=O)(=O)N1CCN(Cc2nnnn2-c2ccc(C#N)cc2)CC1] | 4-(5-{[4-(ethylsulfonyl)-1-piperazinyl]methyl}-1H-tetrazol-1-yl)benzonitrile | MS ES + ve m/z 362 (M + H) |

-continued

| Compound No. | Structure | Name | Analytical data |
|---|---|---|---|
| 119 | 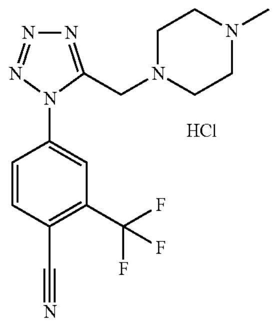 [SMILES: CN1CCN(Cc2nnnn2-c2ccc(C#N)c(C(F)(F)F)c2)CC1 ; Cl] | 4-{5-[(4-methyl-1-piperazinyl)methyl]-1H-tetrazol-1-yl}-2-(trifluoromethyl)benzonitrile | MS ES + ve m/z 352 (M + H) |
| 120 | 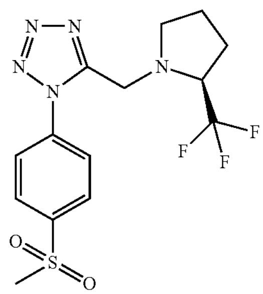 [SMILES: CS(=O)(=O)c1ccc(-n2nnnc2CN2CCC[C@H]2C(F)(F)F)cc1] | 1-[4-(methylsulfonyl)phenyl]-5-{[(2S)-2-(trifluoromethyl)-1-pyrrolidinyl]methyl}-1H-tetrazole | MS ES − ve m/z 374 (M − H) |
| 121 | 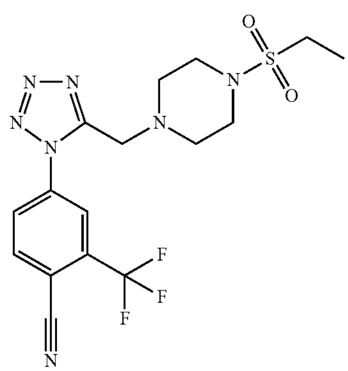 [SMILES: CCS(=O)(=O)N1CCN(Cc2nnnn2-c2ccc(C#N)c(C(F)(F)F)c2)CC1] | 4-(5-{[4-(ethylsulfonyl)-1-piperazinyl]methyl}-1H-tetrazol-1-yl)-2-(trifluoromethyl)benzonitrile | MS ES + ve m/z 430 (M + H) |
| 122 | 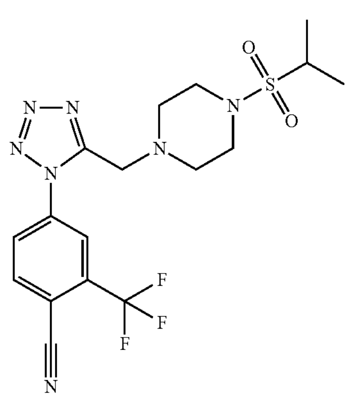 [SMILES: CC(C)S(=O)(=O)N1CCN(Cc2nnnn2-c2ccc(C#N)c(C(F)(F)F)c2)CC1] | 4-[5-({4-[(1-methylethyl)sulfonyl]-1-piperazinyl}methyl)-1H-tetrazol-1-yl]-2-(trifluoromethyl)benzonitrile | MS ES + ve m/z 444 (M + H) |

-continued

| Compound No. | Structure | Name | Analytical data |
|---|---|---|---|
| 123 | 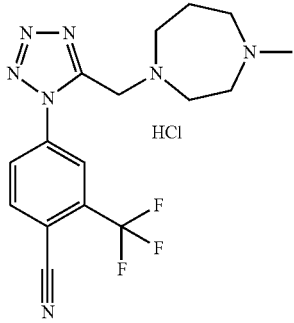 [SMILES: CN1CCCN(Cc2nnnn2-c2ccc(C#N)c(C(F)(F)F)c2)CC1 ; Cl] | 4-{5-[(4-methylhexahydro-1H-1,4-diazepin-1-yl)methyl]-1H-tetrazol-1-yl}-2-(trifluoromethyl)benzonitrile hydrochloride | MS ES + ve m/z 366 (M + H) |
| 124 | 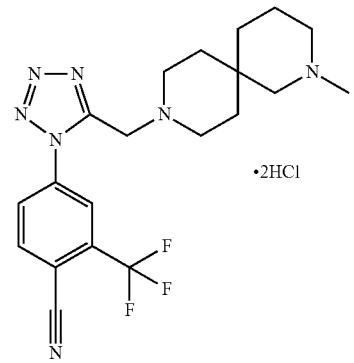 [SMILES: CN1CCCC2(CCN(Cc3nnnn3-c3ccc(C#N)c(C(F)(F)F)c3)CC2)C1 ; "·2HCl"] | 4-{5-[(2-methyl-2,9-diazaspiro[5.5]undec-9-yl)methyl]-1H-tetrazol-1-yl}-2-(trifluoromethyl)benzonitrile hydrochloride | MS ES + ve m/z 420 (M + H) |
| 125 | 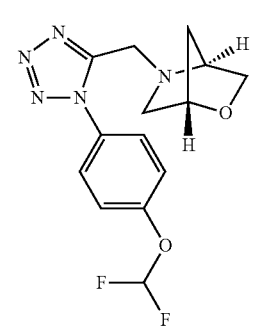 [SMILES: FC(F)Oc1ccc(-n2nnnc2CN2C[C@@H]3C[C@H]2CO3)cc1] | (1S,4S)-5-[(1-{4-[(difluoromethyl)oxy]phenyl}-1H-tetrazol-5-yl)methyl]-2-oxa-5-azabicyclo[2.2.1]heptane hydrochloride | MS ES + ve m/z 324 (M + H) |
| 126 | 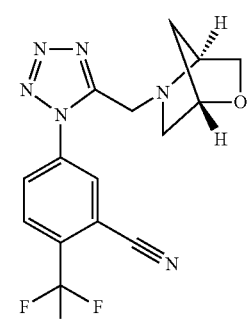 | 5-{5-[(1S,4S)-2-oxa-5-azabicyclo[2.2.1]hept-5-ylmethyl]-1H-tetrazol-1-yl}-2-(trifluoromethyl)benzonitrile | MS ES + ve m/z 351 (M + H) |

-continued

| Compound No. | Structure | Name | Analytical data |
|---|---|---|---|
| 127 | 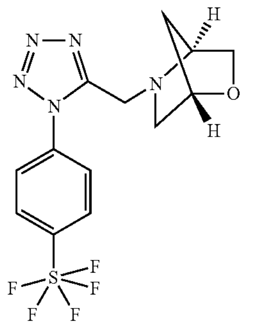 [SMILES: FS(F)(F)(F)(F)c1ccc(-n2nnnc2CN2C[C@@H]3C[C@H]2CO3)cc1] | (1S,4S)-5-({1-[4-(pentafluoro-λ⁶-sulfanyl)phenyl]-1H-tetrazol-5-yl}methyl)-2-oxa-5-azabicyclo[2.2.1]heptane | MS ES + ve m/z 384 (M + H) |
| 128 | 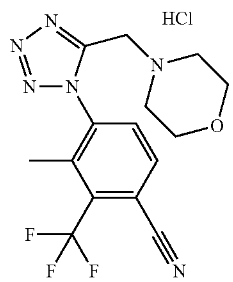 [SMILES: Cl ; Cc1c(-n2nnnc2CN2CCOCC2)ccc(C#N)c1C(F)(F)F] | 3-methyl-4-[5-(4-morpholinylmethyl)-1H-tetrazol-1-yl]-2-(trifluoromethyl)benzonitrile hydrochloride | MS ES + ve m/z 353 (M + H) |
| 129 | 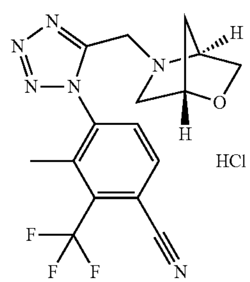 [SMILES: Cc1c(-n2nnnc2CN2C[C@@H]3C[C@H]2CO3)ccc(C#N)c1C(F)(F)F ; Cl] | 3-methyl-4-{5-[(1S,4S)-2-oxa-5-azabicyclo[2.2.1]hept-5-ylmethyl]-1H-tetrazol-1-yl}-2-(trifluoromethyl)benzonitrile hydrochloride | MS ES + ve m/z 365 (M + H) |
| 130 | 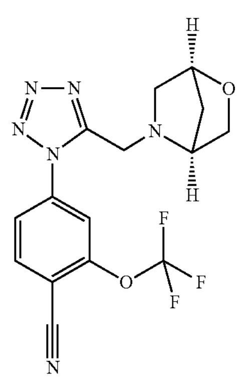 [SMILES: N#Cc1ccc(-n2nnnc2CN2C[C@@H]3C[C@H]2CO3)cc1OC(F)(F)F] | 4-{5-[(1S,4S)-2-oxa-5-azabicyclo[2.2.1]hept-5-ylmethyl]-1H-tetrazol-1-yl}-2-[(trifluoromethyl)oxy]benzonitrile | MS ES + ve m/z 367 (M + H) |

| Compound No. | Structure | Name | Analytical data |
|---|---|---|---|
| 131 | 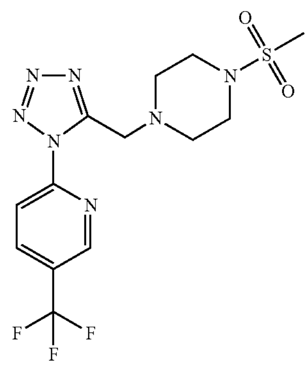 [SMILES: CS(=O)(=O)N1CCN(Cc2nnnn2-c2ccc(C(F)(F)F)cn2)CC1] | 1-(methylsulfonyl)-4-({1-[5-(trifluoromethyl)-2-pyridinyl]-1H-tetrazol-5-yl}methyl)piperazine | MS ES + ve m/z 392 (M + H) |
| 132 | 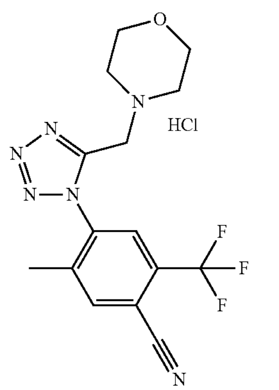 [SMILES: Cc1cc(C#N)c(C(F)(F)F)cc1-n1nnnc1CN1CCOCC1 ; Cl] | 5-methyl-4-[5-(4-morpholinylmethyl)-1H-tetrazol-1-yl]-2-(trifluoromethyl) benzonitrile hydrochloride | MS ES + ve m/z 353 (M + H) |
| 133 | 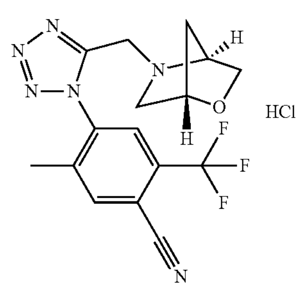 [SMILES: Cc1cc(C#N)c(C(F)(F)F)cc1-n1nnnc1CN1C[C@@H]2C[C@H]1CO2 ; Cl] | 5-methyl-4-{5-[(1S,4S)-2-oxa-5-azabicyclo[2.2.1]hept-5-ylmethyl]-1H-tetrazol-1-yl}-2-(trifluoromethyl) benzonitrile hydrochloride | MS ES + ve m/z 365 (M + H) |
| 134 | 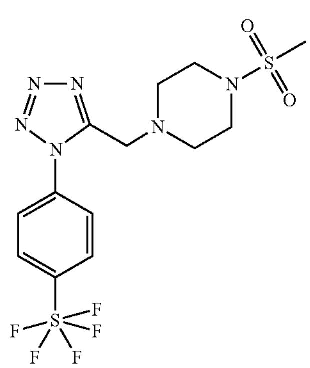 [SMILES: CS(=O)(=O)N1CCN(Cc2nnnn2-c2ccc(S(F)(F)(F)(F)F)cc2)CC1] | 1-(methylsulfonyl)-4-({1-[4-(pentafluoro-$\lambda^6$-sulfanyl)phenyl]-1H-tetrazol-5-yl}methyl)piperazine | MS ES + ve m/z 449 (M + H) |

-continued

| Compound No. | Structure | Name | Analytical data |
|---|---|---|---|
| 135 | 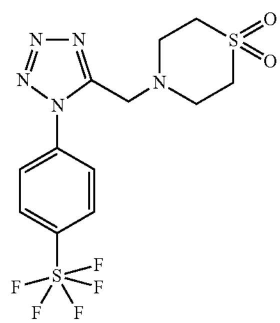 [SMILES: O=S1(=O)CCN(Cc2nnnn2-c2ccc(S(F)(F)(F)(F)F)cc2)CC1] | 4-({1-[4-(pentafluoro-λ⁶-sulfanyl)phenyl]-1H-tetrazol-5-yl}methyl)thiomorpholine 1,1-dioxide | MS ES + ve m/z 420 (M + H) |
| 136 | 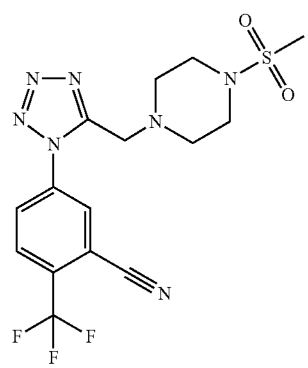 [SMILES: CS(=O)(=O)N1CCN(Cc2nnnn2-c2ccc(C(F)(F)F)c(C#N)c2)CC1] | 5-(5-{[4-(methylsulfonyl)-1-piperazinyl]methyl}-1H-tetrazol-1-yl)-2-(trifluoromethyl)benzonitrile | MS ES + ve m/z 416 (M + H) |
| 137 | 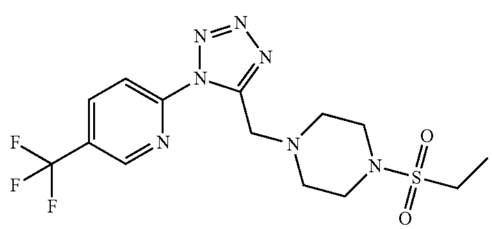 [SMILES: CCS(=O)(=O)N1CCN(Cc2nnnn2-c2ccc(C(F)(F)F)cn2)CC1] | 1-(ethylsulfonyl)-4-({1-[5-(trifluoromethyl)-2-pyridinyl]-1H-tetrazol-5-yl}methyl)piperazine | MS ES + ve m/z 406 (M + H) |
| 138 | 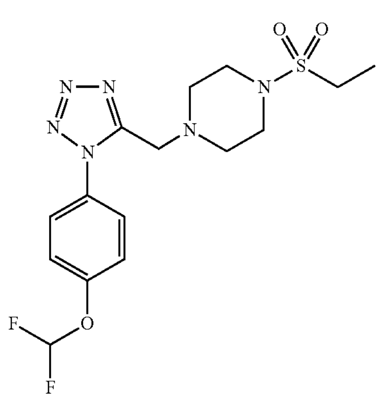 [SMILES: CCS(=O)(=O)N1CCN(Cc2nnnn2-c2ccc(OC(F)F)cc2)CC1] | 1-[(1-{4-[(difluoromethyl)oxy]phenyl}-1H-tetrazol-5-yl)methyl]-4-(ethylsulfonyl)piperazine | MS ES + ve m/z 403 (M + H) |

| Compound No. | Structure | Name | Analytical data |
|---|---|---|---|
| 139 | 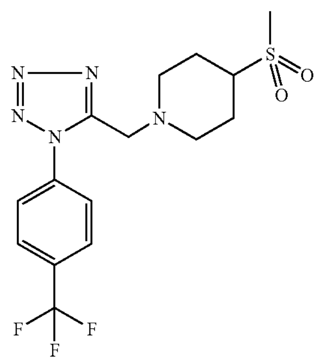 [SMILES: CS(=O)(=O)C1CCN(Cc2nnnn2-c2ccc(C(F)(F)F)cc2)CC1] | 4-(methylsulfonyl)-1-({1-[4-(trifluoromethyl)phenyl]-1H-tetrazol-5-yl}methyl)piperidine | MS ES + ve m/z 390 (M + H) |
| 140 | 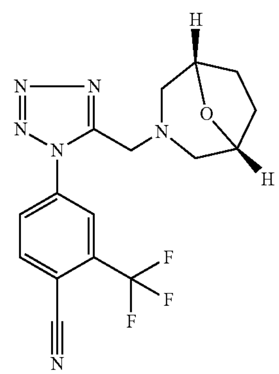 [SMILES: N#Cc1ccc(-n2nnnc2CN2C[C@H]3CC[C@@H](C2)O3)cc1C(F)(F)F] | 4-{5-[8-oxa-3-azabicyclo[3.2.1]oct-3-ylmethyl]-1H-tetrazol-1-yl}-2-(trifluoromethyl)benzonitrile | MS ES + ve m/z 365 (M + H) |
| 141 | 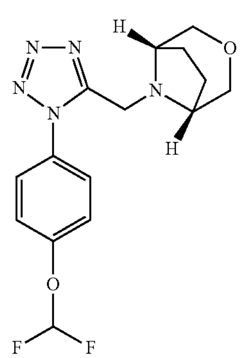 [SMILES: FC(F)Oc1ccc(-n2nnnc2CN2[C@@H]3CC[C@H]2COC3)cc1] | (1R,5S)-8-[(1-{4-[(difluoromethyl)oxy]phenyl}-1H-tetrazol-5-yl)methyl]-3-oxa-8-azabicyclo[3.2.1]octane | MS ES + ve m/z 338 (M + H) |

5-(chloromethyl)-1-[4-(methylsulfonyl)phenyl]-1H-tetrazole used in the preparation of examples 117 and 120 is commercially available from UkrOrgSynthesis, Kiev, Ukraine.

5-(chloromethyl)-1-{4-[(difluoromethyl)oxy]phenyl}-1H-tetrazole used in the preparation of examples 125, 138 and 141 is commercially available from UkrOrgSynthesis, Kiev, Ukraine.

The starting amine for Example 124 is commercially available, for example from ASW Med Chem, New Brunswick, USA.

The starting amine for Example 139 is commercially available, for example from Pharmablock R&D, Carrboro, N.C., USA.

The starting amine for Example 140 is commercially available, for example from FluoroChem, Old Glossop, UK.

The following compounds were prepared in a similar manner to that described for Compound 33, using the appropriate substituted piperazinone intermediate and alkylating agent:

| Compound No. | Structure | Name | Analytical data |
| --- | --- | --- | --- |
| 142 | 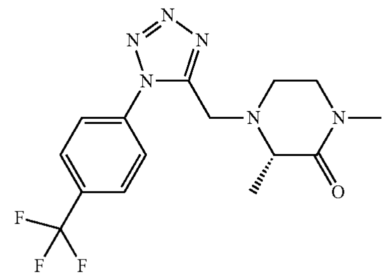 [SMILES: C[C@H]1C(=O)N(C)CCN1Cc1nnnn1-c1ccc(C(F)(F)F)cc1] | (3S)-1,3-dimethyl-4-({1-[4-(trifluoromethyl)phenyl]-1H-tetrazol-5-yl}methyl)-2-piperazinone | MS ES + ve m/z 355 (M + H) |
| 143 | 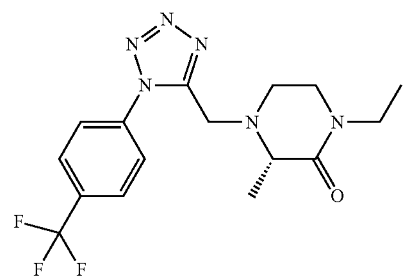 [SMILES: CCN1CCN(Cc2nnnn2-c2ccc(C(F)(F)F)cc2)[C@@H](C)C1=O] | (3S)-1-ethyl-3-methyl-4-({1-[4-(trifluoromethyl)phenyl]-1H-tetrazol-5-yl}methyl)-2-piperazinone | MS ES + ve m/z 369 (M + H) |

The following compounds were prepared in a similar manner to that described for Compound 45, using the appropriate substituted piperazine intermediate and alkylating agent:

| Compound No. | Structure | Name | Analytical data |
| --- | --- | --- | --- |
| 144 | •2 HCl | 4-{5-[(2-methyl-2,8-diazaspiro[4.5]dec-8-yl)methyl]-1H-tetrazol-1-yl}-2-(trifluoromethyl)benzonitrile dihydrochloride | MS ES + ve m/z 406 (M + H) |

The following compounds were prepared in a similar manner to that described for Example 102, using the appropriate piperazine intermediate and acid chloride.

| Compound No. | Structure | Name | Analytical data |
|---|---|---|---|
| 145 | 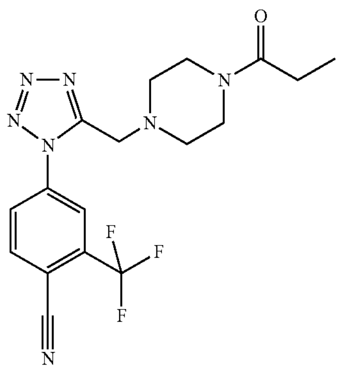 [SMILES: CCC(=O)N1CCN(Cc2nnnn2-c2ccc(C#N)c(C(F)(F)F)c2)CC1] | 4-{5-[(4-propanoyl-1-piperazinyl)methyl]-1H-tetrazol-1-yl}-2-(trifluoromethyl)benzonitrile | MS ES + ve m/z 394 (M + H) |
| 146 | 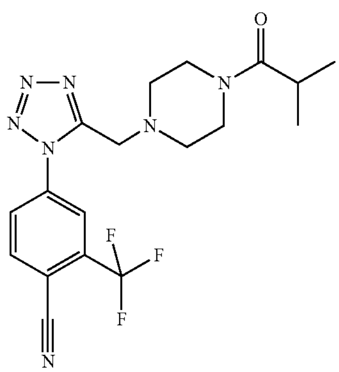 [SMILES: CC(C)C(=O)N1CCN(Cc2nnnn2-c2ccc(C#N)c(C(F)(F)F)c2)CC1] | 4-(5-{[4-(2-methylpropanoyl)-1-piperazinyl]methyl}-1H-tetrazol-1-yl)-2-(trifluoromethyl)benzonitrile | MS ES + ve m/z 408 (M + H) |

The following compounds were prepared in a similar manner to that described for Compound 51, using the appropriate amine intermediate and aldehyde or ketone.

| Compound No. | Structure | Name | Analytical data |
|---|---|---|---|
| 147 | ·2HCl | 4-(5-{[2-(1-methylethyl)-2,8-diazaspiro[4.5]dec-8-yl]methyl}-1H-tetrazol-1-yl)-2-(trifluoromethyl)benzonitrile dihydrochloride | MS ES + ve m/z 434 (M + H) |

Where a compound is given as a hydrochloride salt, the exact ratio between the compound and hydrochloride has not been determined. Hence, as a skilled chemist will appreciate, the ratio may be anywhere between 1:1 and 1:2.

Equipment:

$^1$H NMR Spectra

Chemical shifts are expressed in parts per million (ppm, units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Mass-Directed Automated HPLC/Mass-Directed Automated Preparation (MDAP)

Where indicated in the above compounds, purification by mass-directed automated HPLC was carried out using the following apparatus and conditions:

Hardware

Waters 2525 Binary Gradient Module

Waters 515 Makeup Pump

Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector
Software
    Waters MassLynx version 4 SP2
Column
    The columns used are Waters Atlantis, the dimensions of which are 19 mm×100 mm (small scale) and 30 mm×100 mm (large scale). The stationary phase particle size is 5 µm.
Solvents
    A: Aqueous solvent=Water+0.1% Formic Acid
    B: Organic solvent=Acetonitrile+0.1% Formic Acid
    Make up solvent=Methanol:Water 80:20
    Needle rinse solvent=Methanol
Methods
    There are five methods used depending on the analytical retention time of the compound of interest. They have a 13.5-minute runtime, which comprises of a 10-minute gradient followed by a 3.5 minute column flush and re-equilibration step.
    Large/Small Scale 1.0-1.5=5-30% B
    Large/Small Scale 1.5-2.2=15-55% B
    Large/Small Scale 2.2-2.9=30-85% B
    Large/Small Scale 2.9-3.6=50-99% B
    Large/Small Scale 3.6-5.0=80-99% B (in 6 minutes followed by 7.5 minutes flush and re-equilibration)
Flow Rate
    All of the above methods have a flow rate of either 20 mls/min (Small Scale) or 40 mls/min (Large Scale).
High pH Focused Preparative Open Access LC/MS (High pH MDAP)
Column
    The columns used are Xbridge O18 column, the dimensions of which are 19 mm×100 mm (small scale) and 30 mm×150 mm (large scale). The stationary phase particle size is 5 µm.
Solvents
    A: Aqueous solvent=10 mM ammonium bicarbonate in water adjusted to pH10 with ammonia solution
    B: Organic solvent=Acetonitrile
Methods
    There are five methods used depending on the analytical retention time of the compound of interest. The user can select a 15 minute or 25 minute runtime.
    Large/Small Scale Method A: 99% A to 1% A in B
    Large/Small Scale Method B=85% A to 1% A in B
    Large/Small Scale Method C=70% A to 1% A in B
    Large/Small Scale Method D=50% A to 1% A in B
    Large/Small Scale Method E=20% A to 1% A in B
Flow Rate
    All of the above methods have a flow rate of either 20 mls/min (Small Scale) or 40 mls/min (Large Scale).
UV Detection
    The UV detection was an averaged signal from wavelength of 210 nm to 350 nm and mass spectra were recorded on a mass spectrometer using alternate-scan positive and negative mode electrospray ionization.
Liquid Chromatography/Mass Spectrometry
    Analysis of the above compounds by Liquid Chromatography/Mass Spectrometry (LC/MS) was carried out using the following apparatus and conditions:
Hardware
    Waters Acquity Binary Solvent Manager
    Waters Acquity Sample Manager
    Waters Acquity PDA
    Waters ZQ Mass Spectrometer
    Sedere Sedex 75
Software
    Waters MassLynx version 4.1
Column
    The column used is a Waters Acquity BEH UPLC C18, the dimensions of which are 2.1 mm×50 mm. The stationary phase particle size is 1.7 µm.
Solvents
    A: Aqueous solvent=Water+0.05% Formic Acid
    B: Organic solvent=Acetonitrile+0.05% Formic Acid
    Weak Wash=1:1 Methanol Water
    Strong Wash=Water
Method
    The generic method used has a 2 minute runtime.

| Time/min | % B |
| --- | --- |
| 0 | 3 |
| 0.1 | 3 |
| 1.5 | 97 |
| 1.9 | 97 |
| 2.0 | 3 |

The above method has a flow rate of 1 ml/min.
    The injection volume for the generic method is 0.5 ul
    The column temperature is 40° C.
    The UV detection range is from 220 to 330 nm
High pH Liquid Chromatography/Mass Spectroscopy
    The analysis was conducted on an Acquity UPLC BEH C18 column (2.1 mm×50 mm i.d. 1.7 um packing diameter) at 40 degrees centigrade.
    The solvents employed were:
    A=10 mM Ammonium Bicarbonate in water adjusted to pH 10 with ammonia solution
    B=Acetonitrile
    The gradient employed was from 1-100% B in A over a period of 2 minutes
    The UV detection was an averaged signal from wavelength of 220 nm to 350 nm and mass spectra were recorded on a mass spectrometer using alternate-scan positive and negative mode electrospray ionization
    Alternatively, the analysis was conducted on an XBridge C18 column (4.6 mm×50 mm i.d. 3.5 um packing diameter) at 30 degrees centigrade.
    The solvents employed were:
    A=10 mM Ammonium Bicarbonate in water adjusted to pH 10 with ammonia solution
    B=Acetonitrile
    The gradient employed was from 1-97% B in A over a period of 5 minutes
    The UV detection was an averaged signal from wavelength of 220 nm to 350 nm and mass spectra were recorded on a mass spectrometer using alternate-scan positive and negative mode electrospray ionization
Biotage SP4®
    Biotage-SP4® is an automated purification system. It uses preloaded silica gel columns. The user applies their material to the top of the column and chooses solvents, gradients, flow rates, column size, collection method and eluting volumes.
    The Biotage SP4® may also be used in reverse phase mode using a C18 column. The user applies their material to the top of the column and runs a standard gradient from 0-100% (0.1% formic acid in acetonitrile) in (0.1% formic acid in water). The user chooses the flow rate, column size, collection method and eluting volumes.

Phase Separators (Hydrophobic Frit)

Phase separators are a range of ISOLUTE® columns fitted with an optimized frit material that easily separates aqueous phase from chlorinated solvents under gravity.

SCX—Strong Cation Exchange Cartridge

Where indicated in the compounds, an SCX cartridge was used as part of the compound purification process. Typically an ISOLUTE SCX-2 cartridge was used. ISOLUTE SCX-2 is a silica-based sorbent with a chemically bonded propylsulfonic acid functional group.

ISOLUTE SCX-2 Chemical Data
Base Material Silica, 50 μm
Functional Group Propylsulfonic acid
Capacity: 0.6 meq/g
Counter Ion: Proton SAX—Strong Anion Exchange Cartridge Where indicated in the compounds, an SAX cartridge was used as part of the compound purification process. Typically an ISOLUTE SAX cartridge was used. ISOLUTE SAX is a silica-based sorbent with a chemically bonded quaternary trimethylaminopropyl chloride functional group.

$NH_2$—Aminopropyl Ion Exchange Cartridge

Where indicated in the compounds, an $NH_2$ cartridge was used as part of the compound purification process. Typically an ISOLUTE $NH_2$ cartridge was used. ISOLUTE $NH_2$ is a silica-based sorbent with a chemically bonded aminopropyl functional group.

Description: Aminopropyl functionalized silica. Manufactured using trifunctional silane. pK 9.8. Non end-capped.

Average Particle Size: 50 μm
Nominal Porosity: 60 Å
Exchange Capacity: 0.6 meq/g
Comments: Weak anion exchange sorbent for extraction of strongly ionized acidic drugs, particularly for ease of elution.

Pharmacological Data

Compounds as defined in the first or second aspect may be tested for in vitro biological activity in the $hCa_v2.2$ assay in accordance with the following studies:

Methods

Cell Biology

Stable cell lines expressing the human $Ca_v2.2$ α ($α1_B$) subunit, along with the human β3 and α2δ1 auxiliary subunits were created following sequential transfection and selection of human embryonic kidney (HEK293) cells. HEK293 cells were cultured in Dulbecco's modified Eagles media/F12 media (Invitrogen, Cat #041-95750V) containing 10% fetal bovine serum, with added L-glutamine (2 mM; Invitrogen, Cat #25030-024) and non-essential amino acids (5%; Invitrogen, Cat #11140-035). Initially HEK293 cells were transfected with two plasmid vectors for expression of the $hCa_v2.2$ α subunit (pCIN5-$hCa_v2.2$ which carries a neomycin resistance marker) and the $hCa_v$ β3 subunit (pCIH-$hCa_v$-β3 which carries a hygromycin resistance marker). Clonal cell lines were isolated following selection in media supplemented with 0.4 mg ml$^{-1}$ Geneticin G418 (Invitrogen, Cat #10131-027) and 0.1 mg ml$^{-1}$ hygromycin (Invitrogen, Cat #10687-010). These clonal cell lines were assessed for $Ca_v2.2$ α/β3-mediated current expression using the IonWorks planar array electrophysiology technology (described below). A clonal line was identified that gave a reasonable level of functional $Ca_v2.2$ α/β3 current expression. This cell line was transfected with a plasmid vector for expression of the human α2δ1 subunit (pCIP-α2δ1 which carries a puromycin resistance marker) and clonal cell lines isolated following selection in media containing 0.62 μg ml$^{-1}$ puromycin (Sigma, Cat # P-7255), in addition to 0.4 mg ml$^{-1}$ Geneticin G418 and 0.1 mg ml$^{-1}$ hygromycin. Several cell lines were identified that gave robust levels of $Ca_v2.2$ α/β3/α2δ1-mediated current expression and one of these was selected for compound profiling. Expression of all three subunits within this cell line was continuously maintained by the inclusion of G418 (0.4 mg ml$^{-1}$), hygromycin (0.1 mg ml$^{-1}$) and puromycin (0.62 μg ml$^{-1}$). Cells were maintained at 37° C. in a humidified environment containing 5% $CO_2$ in air. Cells were liberated from the T175 culture flasks for passage and harvesting using TrpLE (Invitrogen, Cat #12604-013).

Cell Preparation

Cells were grown to 30-60% confluence in T175 flasks and maintained at 30° C. for 24 hrs prior to recording. Cells were lifted by removing the growth media, washing with $Ca^{2+}$ free PBS (Invitrogen, Cat #14190-094) and incubating with 3 ml of warmed (37° C.) TrpLE (Invitrogen, Cat #12604-013) for 6 minutes. Lifted cells were suspended in 10 ml of extracellular buffer. Cell suspension was then placed into a 15 ml tube and centrifuged for 2 minutes at 700 rpm. After centrifugation, the supernatant was removed and the cell pellet was resuspended in 4.5 ml of extracellular solution.

Electrophysiology

Currents were recorded at room temperature (21-23° C.) using the IonWorks planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential ($V_H$) of −90 mV to +10 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 120, KCl 20 mM, $MgCl_2$ 5, EGTA 5, HEPES 10, adjusted to pH 7.3. Amphotericin was prepared as 30 mg/ml stock solution and diluted to a final working concentration of 0.2 mg ml$^{-1}$ in intracellular buffer solution. The extracellular solution contained the following (in mM): Na-gluconate 120, NaCl 20, $MgCl_2$ 1, HEPES 10, $BaCl_2$ 5, adjusted to pH 7.4.

Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using seal resistance (>40 MΩ), resistance reduction (>35%) and peak current amplitude (>200 pA) in the absence of compound to eliminate unsuitable cells from further analysis. Paired comparisons between pre-compound and post-compound additions were used to determine the inhibitory effect of each compound. The concentrations of compounds required to inhibit current elicited by the $1^{st}$ depolarising pulse by 50% (tonic pIC50) were determined by fitting of the Hill equation to the concentration response data. In addition the use-dependent inhibitory properties of the compounds were determined by assessing the effect of compounds on the $10^{th}$ versus $1^{st}$ depolarising pulse. The ratio of the $10^{th}$ over $1^{st}$ pulse was determined in the absence and presence of drug and the % use-dependent inhibition calculated. The data was fitted using the same equation as for the tonic $pIC_{50}$ and the concentration producing 30% inhibition (use-dependent $pUD_{30}$) determined.

The compounds 1 to 111, 116 t6 129 and 142 t6 147 were tested in the $hCa_v2.2$ assay.

Compounds 1 to 80, 84 to 107, 109 to 111, 116 to 129 and 142 to 147 showed activity in the above assay.

For compounds 102, 106, 121, 122, 145, 147, no $pUD_{30}$ value was determined.

The compounds 1 to 17, 19, 19a, 20 to 31, 33, 34, 35, 37 to 45, 47 to 59, 61 to 80, 84 to 96, 101, 103 to 105, 107, 109 to 111, 116 to 120, 124 to 129, 142 to 144 and 146 exhibited a $pUD_{30}$ value of 4.5 or more than 4.5. The compounds 1 to 14, 19, 19a, 21 to 26, 28 to 31, 33 to 35, 37 to 45, 47 to 49, 51 to 55, 57, 63 to 68, 70 to 74, 76 to 80, 84 to 96, 101, 104, 107, 109 to 111, 116, 120, 125 to 129, 142, 143 and 146 exhibited a $pUD_{30}$ value of 5.0 or more than 5.0. The compounds 1 to 7, 19a, 21 to 26, 28 to 30, 37, 39 to 44, 47 to 49, 52 to 54, 57, 63, 64 67, 72, 77, 80, 90, 92 to 94, 96, 103, 109 to 111, 116, 120, 127, 128, 129, 143 and 146 exhibited a $pUD_{30}$ value of 5.5 or more than 5.5. Compound 33 exhibited a $pUD_{30}$ value of 5.3.

The compounds 3, 9, 13, 19, 21, 23 to 25, 28 to 30, 34, 39, 41, 42, 45, 47, 48, 52, 54, 57, 64, 65, 70 to 74, 77 to 79, 89, 90, 92, 94, 96, 98, 101 to 103, 106, 107, 110, 111, 118, 121, 122, 127, 129, 145 to 147 exhibited a $pIC_{50}$ value of 4.5 or more than 4.5. The compounds 21, 25, 28 to 30, 39, 41, 47, 48, 71, 72, 74, 89, 90, 101 to 103, 106, 107, 110, 111, 121, 122, 145 to 147 exhibited a $pIC_{50}$ value of 5.0 or more than 5.0. The compounds 25, 28, 41, 48, 71, 102, 106, 107, 111, 121, 122, 145 to 147 exhibited a $pIC_{50}$ value of 5.5 or more than 5.5. Compound 33 exhibited a $pIC_{50}$ value of 4.2.

The invention claimed is:

1. A compound of formula (I), or a salt thereof:

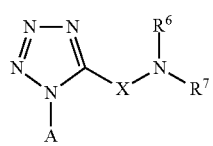

(I)

wherein
A is

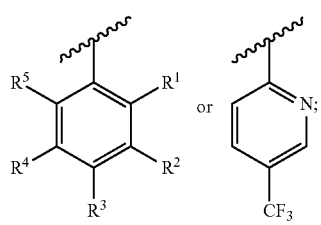

$R^1$ is hydrogen, methyl or chloro;
$R^2$ is hydrogen, trifluoromethyl, trifluoromethoxy, chloro or cyano;
$R^3$ is hydrogen, cyano, trifluoromethyl, trifluoromethoxy, difluoromethoxy, chloro, bromo, —S—$CH_3$, —$SO_2$—$C_{1-3}$alkyl or —$SF_5$;
$R^4$ is hydrogen, trifluoromethyl, trifluoromethoxy, chloro or cyano;
$R^5$ is hydrogen, methyl or chloro;

wherein at least one of $R^1$, $R^2$, $R^3$, $R^4$ or $R^5$ is a group other than hydrogen;
X is —$CH_2$—, —$CH_2$—$CH_2$— or —$CH(CH_3)$—;
wherein when $R^1$ is methyl, $R^5$ is hydrogen or chloro, and when $R^5$ is methyl, $R^1$ is hydrogen or chloro;
wherein when $R^2$ is chloro, $R^4$ is hydrogen, trifluoromethyl, trifluoromethoxy or cyano, and when $R^4$ is chloro, $R^2$ is hydrogen, trifluoromethyl, trifluoromethoxy or cyano;
$R^6$ is hydrogen and $R^7$ is $C_{1-5}$ alkyl or $C_{3-6}$cycloalkyl; or $R^6$ and $R^7$ together with the nitrogen atom to which they are attached form a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, $C_{1-3}$ alkyl, cyano, —$SO_2$—$C_{1-3}$ alkyl, $C_{1-3}$ haloalkyl and —CO—$C_{1-3}$alkyl;
with the proviso that the compound is not 4-({1-[3-(trifluoromethyl)phenyl]-1H-tetrazol-5-yl}methyl)morpholine hydrochloride, 4-({1-[3-(trifluoromethyl)phenyl]-1H-tetrazol-5-yl}methyl)morpholine, 4-{[1-(3,4-dichlorophenyl)-1H-tetrazol-5-yl]methyl}morpholine, 1-{[1-(4-chlorophenyl)-1H-tetrazol-5-yl]methyl}-4-(methylsulfonyl)piperazine, 1-{[1-(4-chlorophenyl)-1H-tetrazol-5-yl]methyl}-4-(propylsulfonyl)piperazine; 1-{[1-(3,4-dichlorophenyl)-1H-tetrazol-5-yl]methyl}piperidine; 4-{[1-(4-chlorophenyl)-1H-tetrazol-5-yl]methyl}morpholine; 1-{[1-(4-chlorophenyl)-1H-tetrazol-5-yl]methyl}-4-methylpiperidine; 1-{[1-(4-chlorophenyl)-1H-tetrazol-5-yl]methyl}piperidine; 1-{[1-(4-chlorophenyl)-1H-tetrazol-5-yl]methyl}-4-(ethylsulfonyl)piperazine; 1-{[1-(4-chlorophenyl)-1H-tetrazol-5-yl]methyl}-2-methylpiperidine; 1-{[1-(4-chlorophenyl)-1H-tetrazol-5-yl]methyl}piperazine; 1-(4-chlorophenyl)-5-(1-pyrrolidinylmethyl)-1H-tetrazole; 1-{[1-(4-chlorophenyl)-1H-tetrazol-5-yl]methyl}-4-methylpiperazine or 1-{[1-(4-chlorophenyl)-1H-tetrazol-5-yl]methyl}hexahydro-1H-azepine.

2. A compound or salt according to claim 1 of formula (Ia)

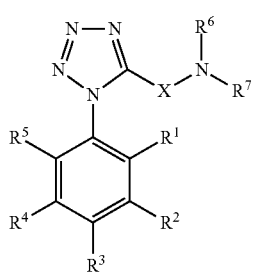

(Ia)

wherein
$R^1$ is hydrogen, methyl or chloro;
$R^2$ is hydrogen or trifluoromethyl;
$R^3$ is hydrogen, cyano, trifluoromethyl, trifluoromethoxy or chloro;
$R^4$ is hydrogen or trifluoromethyl;
$R^5$ is hydrogen, methyl or chloro;

X is —CH₂— or —CH₂—CH₂—;
wherein when R¹ is methyl, R⁵ is hydrogen or chloro, and when R⁵ is methyl, R¹ is hydrogen or chloro;
R⁶ is hydrogen and R⁷ is C_{1-3}alkyl; or R⁶ and R⁷ together with the nitrogen atom to which they are attached form a 5 to 6 membered heterocyclyl ring or 2,8-diazaspiro[4.5]decan-1-one group either of which is unsubstituted or substituted with 1 or 2 substituents independently selected from halogen, oxo and C_{1-3}alkyl; with the proviso that the compound is not 4-{[1-(4-chlorophenyl)-1H-tetrazol-5-yl]methyl}morpholine, 4-({1-[3-(trifluoromethyl)phenyl]-1H-tetrazol-5-yl}methyl)morpholine hydrochloride or 4-({1-[3-(trifluoromethyl)phenyl]-1H-tetrazol-5-yl}methyl)morpholine.

3. A compound or salt according to claim 1, wherein R⁶ is hydrogen and R⁷ is C_{1-5}alkyl or C_{3-6}cycloalkyl; or R⁶ and R⁷ together with the nitrogen atom to which they are attached forms a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered Spiro ring system; which ring system B is unsubstituted or substituted with 1 to 3 substituents independently selected from halogen, oxo, C_{1-3}alkyl, cyano, —SO₂—C_{1-3}alkyl and C_{1-3}haloalkyl;
with the proviso that the compound is not
4-{5-[(3,4-dimethyl-1-piperazinyl)methyl]-1H-tetrazol-1-yl}benzonitrile dihydrochloride;
4-(5-{[4-(1-methylethyl)-1-piperazinyl]methyl}-1H-tetrazol-1-yl)benzonitrile dihydrochloride; or
4-{5-[(4-methyl-1-piperazinyl)methyl]-1H-tetrazol-1-yl}benzonitrile dihydrochloride.

4. A compound or salt according to claim 1, wherein R⁶ and R⁷ together with the nitrogen atom to which they are attached forms a saturated ring system B, where B is selected from
a) a 4 to 7 membered monocyclic heterocyclic ring,
b) a 5 to 10 membered fused bicyclic ring system;
c) a bridged 4 to 7 membered monocyclic heterocyclic ring system; and
d) a 7 to 11 membered spiro ring system;
which ring system B is unsubstituted or substituted with 1 to 3 substituents independently selected from halogen, oxo, C_{1-3} alkyl, cyano, —SO₂—C_{1-3} alkyl and C_{1-3}haloalkyl.

5. A compound or salt according to claim 1, wherein R⁶ and R⁷ together with the nitrogen atom to which they are attached form a saturated ring system B, where B is selected from
a) a 4 to 7 membered monocyclic heterocyclic ring,
b) a 5 to 10 membered fused bicyclic ring system; and
c) a bridged 4 to 7 membered monocyclic heterocyclic ring system;
which ring system B is unsubstituted or substituted with 1 to 3 substituents independently selected from halogen, oxo, C_{1-3} alkyl, cyano, —SO₂—C_{1-3} alkyl and C_{1-3} haloalkyl.

6. A compound or salt according to claim 1, wherein R⁶ and R⁷ together with the nitrogen atom to which they are attached form a saturated ring system B, where B is selected from
a) a 4 to 7 membered monocyclic heterocyclic ring selected from
pyrrolidine ring,
morpholine ring,
thiomorpholine ring,
piperazine ring, and
azetidine ring,
b) a 5 to 10 membered fused bicyclic ring system selected from
octahydropyrrolo[1,2-a]pyrazine group,
hexahydro-2H-isothiazolo[2,3-a]pyrazine group, and
octahydro-pyrido[1,2-a]pyrazine group,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from halogen, oxo, C_{1-3} alkyl, cyano, —SO₂—C_{1-3} alkyl and C_{1-3} haloalkyl.

7. A compound or salt according to claim 1, wherein R⁶ and R⁷ together with the nitrogen atom to which they are attached form a saturated ring system B, where B is selected from
a) a 4 to 7 membered monocyclic heterocyclic ring selected from
pyrrolidine ring,
morpholine ring, and
piperazine ring,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents
independently selected from halogen, oxo, C_{1-3} alkyl, cyano, —SO₂—C_{1-3} alkyl and C_{1-3} haloalkyl.

8. A compound or salt according to claim 1, wherein R⁶ and R⁷ together with the nitrogen atom to which they are attached form a saturated ring system B, where B is selected from
a) a 4 to 7 membered monocyclic heterocyclic ring selected from
pyrrolidine ring,
morphonline ring, and
piperazine ring,
c) a bridged 4 to 7 membered monocyclic heterocyclic ring system selected from
2-oxa-5-azabicyclo[2.2.1]heptane group, and
2,5-diazabicyclo[2.2.1]heptane group;
which ring system B is unsubstituted or substituted with 1 to 3 substituents independently selected from fluoro, oxo, methyl, ethyl, propyl, cyano, —SO₂—CH₃, —SO₂—(CH₂)CH₃, —SO₂—(CH₂)₂CH₃ and trifluoromethyl.

9. A compound or salt according to claim 1, wherein R¹ is hydrogen or methyl.

10. A compound or salt according to claim 1, wherein R² is hydrogen, trifluoromethyl or chloro.

11. A compound or salt according to claim 1 wherein R³ is hydrogen, trifluoromethyl or cyano.

12. A compound or salt according to claim 1 wherein R⁵ is hydrogen or methyl.

13. A compound or salt according to claim 1 wherein R³ is trifluoromethyl and R¹, R², R⁴ and R⁵ are hydrogen.

14. A compound or salt according to claim 1 wherein R² is trifluoromethyl and R¹, R³, R⁴ and R⁵ are hydrogen.

15. A compound or salt according to claim 1 wherein R³ is cyano and R¹, R², R⁴ and R⁵ are hydrogen.

16. A compound or salt according to claim 1, wherein X is —CH₂—.

17. A compound or salt according to claim 1, wherein the compound or the salt is selected from 1. 5-[(3,3-Difluoro-1-pyrrolidinyl)methyl]-1-[4-(trifluoromethyl)phenyl]-1H-tetrazole
2. (cis)-2,6-Dimethyl-4-({1-[4-(trifluoromethyl)phenyl]-1H-tetrazol-5-yl}methyl)morpholine
3. (cis)-2,6-Dimethyl-4-({1-[3-(trifluoromethyl)phenyl]-1H-tetrazol-5-yl}methyl)morpholine
4. 4-({1-[4-(Trifluoromethyl)phenyl]-1H-tetrazol-5-yl}methyl)morpholine
5. 4-({1-[2-Chloro-4-(trifluoromethyl)phenyl]-1H-tetrazol-5-yl}methyl)morpholine
6. 5-[2-(3,3-Difluoro-1-pyrrolidinyl)ethyl]-1-[4-(trifluoromethyl)phenyl]-1H-tetrazole
7. 5-(1-Pyrrolidinylmethyl)-1-[4-(trifluoromethyl)phenyl]-1H-tetrazole
8. N-({1-[4-(Trifluoromethyl)phenyl]-1H-tetrazol-5-yl}methyl)-2-propanamine
9. 4-(2-{1-[4-(Trifluoromethyl)phenyl]-1H-tetrazol-5-yl}ethyl)morpholine hydrochloride
10. 4-{[1-(2,4-Dichlorophenyl)-1H-tetrazol-5-yl]methyl}morpholine
11. (cis)-4-(5-{[2,6-Dimethyl-4-morpholinyl]methyl}-1H-tetrazol-1-yl)benzonitrile
12. 8({1-[3-(Trifluoromethyl)phenyl]-1H-tetrazol-5-yl}methyl)-2,8-diazaspiro[4.5]decan-1-one
13. (cis)-4-{[1-(4-Chlorophenyl)-1H-tetrazol-5-yl]methyl}-2,6-dimethylmorpholine
14. 4-[(1-{4-[(Trifluoromethyl)oxy]phenyl}-1H-tetrazol-5-yl)methyl]morpholine
15. 4-({1-[3-(Trifluoromethyl)phenyl]-1H-tetrazol-5-yl}methyl)thiomorpholine 1,1-dioxide
16. (cis)-2,6-Dimethyl-4-(2-{1-[4-(trifluoromethyl)phenyl]-1H-tetrazol-5-yl}ethyl)morpholine
17. 4-{5-[(3,3-Difluoro-1-pyrrolidinyl)methyl]-1H-tetrazol-1-yl)}benzonitrile
18. 1-(4-Chlorophenyl)-5-[(3,3-difluoro-1-pyrrolidinyl)methyl]-1H-tetrazole
24. 1-({1-[3-(Trifluoromethyl)phenyl]-1H-tetrazol-5-yl}methyl)-3-pyrrolidinecarbonitrile hydrochloride
25. (3R)-3-Methyl-4-({1-[3-(trifluoromethyl)phenyl]-1H-tetrazol-5-yl}methyl)morpholine hydrochloride
26. (cis)-2,6-Dimethyl-4-({1-[4-(methylthio)phenyl]-1H-tetrazol-5-yl}methyl)morpholine
27. 4-(5-{[cis-2,6-Dimethyl-4-morpholinyl]methyl}-1H-tetrazol-1-yl)-3-methylbenzonitrile hydrochloride
28. (3R)-3-Methyl-4-({1-[4-(trifluoromethyl)phenyl]-1H-tetrazol-5-yl}methyl)morpholine hydrochloride
29. 3,3-Dimethyl-4-({1-[3-(trifluoromethyl)phenyl]-1H-tetrazol-5-yl}methyl)morpholine
30. 4-(5-{[cis-2,6-Dimethyl-4-morpholinyl]methyl}-1H-tetrazol-1-yl)-2-(trifluoromethyl)benzonitrile
31. 1-Methyl-4-({1-[4-(trifluoromethyl)phenyl]-1H-tetrazol-5-yl}methyl)piperazine dihydrochloride
32. 3-Methyl-4-({1-[3-(trifluoromethyl)phenyl]-1H-tetrazol-5-yl}methyl)-2-piperazinone
33. 1,3-Dimethyl-4-({1-[3-(trifluoromethyl)phenyl]-1H-tetrazol-5-yl}methyl)-2-piperazinone
34. 4-[5-(4-Morpholinylmethyl)-1H-tetrazol-1-yl]-2-(trifluoromethyl)benzonitrile hydrochloride
35. 3-Methyl-1-(1-methylethyl)-4-({1-[3-(trifluoromethyl)phenyl]-1H-tetrazol-5-yl}methyl)-2-piperazinone
36. 4-({1-[3-(Trifluoromethyl)phenyl]-1H-tetrazol-5-yl}methyl)-2-piperazinone
37. 4-(5-{[(cis)-2,5-Dimethyl-1-pyrrolidinyl]methyl}-1H-tetrazol-1-yl)benzonitrile
38. 4-({1-[5-(Trifluoromethyl)-2-pyridinyl]-1H-tetrazol-5-yl}methyl)morpholine
39. (3S)-3-Methyl-4-({1-[4-(trifluoromethyl)phenyl]-1H-tetrazol-5-yl}methyl)morpholine hydrochloride
40. 4-(1-{1-[4-(Trifluoromethyl)phenyl]-1H-tetrazol-5-yl}ethyl)morpholine
41. 4-(5-{[(3R)-3-Methyl-4-morpholinyl]methyl}-1H-tetrazol-1-yl)-2-(trifluoromethyl)benzonitrile
42. (3R)-3-Methyl-4-({1-[5-(trifluoromethyl)-2-pyridinyl]-1H-tetrazol-5-yl}methyl)morpholine
43. (1S,4S)-5-({1-[4-(Trifluoromethyl)phenyl]-1H-tetrazol-5-yl}methyl)-2-oxa-5-azabicyclo[2.2.1]heptane hydrochloride
44. 4-{5-[(1S,4S)-2-Oxa-5-azabicyclo[2.2.1]hept-5-ylmethyl]-1H-tetrazol-1-yl}-2-(trifluoromethyl)benzonitrile
45. 1,2,2-Trimethyl-4-({1-[3-(trifluoromethyl)phenyl]-1H-tetrazol-5-yl}methyl)piperazine hydrochloride
46. 1-({1-[4-(Trifluoromethyl)phenyl]-1H-tetrazol-5-yl}methyl)piperazine
47. 1-(Ethylsulfonyl)-4-({1-[4-(trifluoromethyl)phenyl]-1H-tetrazol-5-yl}methyl)piperazine
48. 1-(Ethylsulfonyl)-4-({1-[3-(trifluoromethyl)phenyl]-1H-tetrazol-5-yl}methyl)piperazine
49. 4-(5-{[(2S)-2-(Trifluoromethyl)-1-pyrrolidinyl]methyl}-1H-tetrazol-1-yl)benzonitrile
50. (1S,4S)-2-({1-[4-(Trifluoromethyl)phenyl]-1H-tetrazol-5-yl}methyl)-2,5-diazabicyclo[2.2.1]heptane
51. (1S,4S)-2-(1-Methylethyl)-5-({1-[4-(trifluoromethyl)phenyl]-1H-tetrazol-5-yl}methyl)-2,5-diazabicyclo[2.2.1]heptane hydrochloride
52. (3R)-1-Ethyl-3-methyl-4-({1-[4-(trifluoromethyl)phenyl]-1H-tetrazol-5-yl}methyl)-2-piperazinone
53. 4-{5-[(3,3-Dimethyl-4-morpholinyl)methyl]-1H-tetrazol-1-yl}benzonitrile
54. (3R)-4-[(1-{4-[(Difluoromethyl)oxy]phenyl}-1H-tetrazol-5-yl)methyl]-3-methylmorpholine hydrochloride
55. (cis)-4-{[1-(4-Bromo-2-methylphenyl)-1H-tetrazol-5-yl]methyl}-2,6-dimethylmorpholine hydrochloride
56. 4-[5-(1-Pyrrolidinylmethyl)-1H-tetrazol-1-yl)benzonitrile hydrochloride
57. cis-4-{[1-(4-Bromo-2-chlorophenyl)-1H-tetrazol-5-yl]methyl}-2,6-dimethylmorpholine hydrochloride
58. (1S,4S)-5-({1-[5-(Trifluoromethyl)-2-pyridinyl]-1H-tetrazol-5-yl}methyl)-2-oxa-5-azabicyclo[2.2.1]heptane hydrochloride
59. 3-5-{[(cis)-2,6-Dimethyl-4-morpholinyl]methyl}-1H-tetrazol-1H-yl)benzonitrile hydrochloride
60. 4-{5-[(Cyclohexylamino)methyl]1H-tetrazol-1-yl}benzonitrile hydrochloride
61. 4-(5-{1[(1-Ethylpropyl)amino]methyl}-1H-tetrazol-1-yl)benzonitrile hydrochloride
62. N-({1-[3-(Trifluoromethyl)phenyl]-1H-tetrazol-5-yl}methyl)cyclopentanamine hydrochloride
63. N-({1-[3-(Trifluoromethyl)phenyl]-1H-tetrazol-5-yl}methyl)-3-pentanamine hydrochloride
64. (cis)-3,5-dimethyl-4-({1-[3-(Trifluoromethyl)phenyl]-1H-tetrazol-5-yl}methyl)morpholine hydrochloride
65. N-({1-[3-(Trifluoromethyl)phenyl]-1H-tetrazol-5-yl}methyl)cyclohexanamine hydrochloride
66. cis-1,2,6-Trimethyl-4-({1-[3-(trifluoromethyl)phenyl]-1H-tetrazol-5-yl}methyl)piperazine formate salt
67. 1,2-Dimethyl-4-({1-[3-(trifluoromethyl)phenyl]-1H-tetrazol-5-yl}methyl)piperazine dihydrochloride
68. 5-(1-Azetidinylmethyl)-1-[4-(trifluoromethyl)phenyl]-1H-tetrazole hydrochloride 69 4-(5-{[(2S)-2-Methyl-1-pyrrolidinyl]methyl}-1H-tetrazol-1-yl)benzonitrile
70 2-({1-[4-(Trifluoromethyl)phenyl]-1H-tetrazol-5-yl}methyl)octahydropyrrolo[1,2-a]pyrazine dihydrochloride
71 1-(Methylsulfonyl)-4-({1-[4-(trifluoromethyl)phenyl]-1H-tetrazol-5-yl}methyl)piperazine
72 1-(Methylsulfonyl)-4-({1-[3-(trifluoromethyl)phenyl]-1H-tetrazol-5-yl}methyl)piperazine
73 4-(5-{[(2R)-2-(Trifluoromethyl)-1-pyrrolidinyl]methyl}-1H-tetrazol-1-yl)benzonitrile
74 2({1-[4-(Trifluoromethyl)phenyl]-1H-tetrazol-5-yl}methyl)hexahydropyrrolo[1,2-a]pyrazin-6(2H)-one
75 5-(1-Azetidinylmethyl)-1-[3-(trifluoromethyl)phenyl]-1H-tetrazole
76 (8aR)-2-({1-[4-(Trifluoromethyl)phenyl]-1H-tetrazol-5-yl}methyl)octahydropyrrolo[1,2-a]pyrazine
77 8a-(Fluoromethyl)-2-({1-[4-(trifluoromethyl)phenyl]-1H-tetrazol-5-yl}methyl)octahydropyrrolo[1,2-a]pyrazine
78 5-({1-[4-(Trifluoromethyl)phenyl]-1H-tetrazol-5-yl}methyl)hexahydro-2H-isothiazolo[2,3-a]pyrazine 1,1-dioxide
79 5-({1-[3-(Trifluoromethyl)phenyl]-1H-tetrazol-5-yl}methyl)hexahydro-2H-isothiazolo[2,3-a]pyrazine 1.1-dioxide
80 2-({1-[4-(Trifluoromethyl)phenyl]-1-H-tetrazol-5-yl}methyl)octahydro-2H-pyrido[1,2-a]pyrazine
81 4-{5-[(3,4-Dimethyl-1-piperazinyl)methyl]-1H-tetrazol-1-yl}benzonitrile dihydrochloride
82 4(5-{[4-(1-Methylethyl)-1-piperazinyl]methyl}-1H-tetrazol-1-yl)benzonitrile dihydrochloride
83 4-{(5-[(4-Methyl-1-piperazinyl)methyl]-1H-tetrazol-1-yl}benzonitrile hydrochloride
84 1-Ethyl-3-methyl-4-({1-[3-(trifluoromethyl)phenyl]-1H-tetrazol-5-yl}methyl)-2-piperazinone
85 1-Methyl-4-({1-[3-(trifluoromethyl)phenyl]-1H-tetrazol-5-yl}methyl)-2-piperazinone
86 1-Ethyl-4-({1-[3-(trifluoromethyl)phenyl]-1H-tetrazol-5-yl}methyl)-2-piperazinone
87 1-(1-Methylethyl)-4-({1-[3-(trifluoromethyl)phenyl]-1H-tetrazol-5-yl}methyl)-2-piperazinone
88 (3 S)-3-Methyl-1-(1-methylethyl)-4-({1-[4-(trifluoromethyl)phenyl]-1H-tetrazol-5-yl}methyl)-2-piperazinone
89 (3R)-1,3-Dimethyl-4-({1-[4-(trifluoromethyl)phenyl]-1H-tetrazol-5-yl}methyl)-2-piperazinone
90 (3R)-3-Methyl-1-(1-methylethyl)-4-({1-[4-(trifluoromethyl)phenyl]-1H-tetrazol-5-yl}methyl)-2-piperazinone
91 1-Ethyl-2,2-dimethyl-4-({1-[3-(trifluoromethyl)phenyl]-1H-tetrazol-5-yl}methyl)piperazine hydrochloride
92 (2R)-4-Ethyl-2-methyl-1-({1-[3-4 trifluoromethyl)phenyl]-1H-tetrazol-5-yl}methyl)piperazine hydrochloride
93 (2R)-2,4-Dimethyl-1-({1-[3-(trifluoromethyl)phenyl]-1H-tetrazol-5-yl}methyl)piperazine hydrochloride
94 (2R)-2-Methyl-4-(1-methylethyl)-1-({1-[3-(trifluoromethyl)phenyl]-1H-tetrazol-5-yl}methyl)piperazine hydrochloride
95 1-Ethyl-4-({1-[4-(trifluoromethyl)phenyl]-1H-tetrazol-5-yl}methyl)piperazine hydrochloride
96 1-(1-Methylethyl)-4-({1-[4-(trifluoromethyl)phenyl]-1H-tetrazol-5-yl}methyl)piperazine
97 (1S,4S)-2-Ethyl-5-({1-[4-(trifluoromethyl)phenyl]-1H-tetrazol-5-yl}methyl)-2,5-diazabicyclo[2.2.1]heptane hydrochloride
98 (1S,4S)-2-Methyl-5-({1-[4-(trifluoromethyl)phenyl]-1H-tetrazol-5-yl}methyl)-2,5-diazabicyclo[2.2.1]heptane hydrochloride
99 3,3-Dimethyl-1-({1-[4-(trifluoromethyl)phenyl]-1H-tetrazol-5-yl}methyl)piperazine dihydrochloride
100 3-Methyl-1-({1-[4-(trifluoromethyl)phenyl]-1H-tetrazol-5-yl}methyl)piperazine dihydrochloride
and a salt thereof.

18. A compound or salt according to claim 1, wherein the salt is pharmaceutically acceptable.

19. A pharmaceutical composition comprising (a) a compound or pharmaceutically acceptable salt according to claim 18 and (b) a pharmaceutically acceptable excipient.

* * * * *